US005834592A

United States Patent [19]
Reed et al.

[11] Patent Number: 5,834,592
[45] Date of Patent: Nov. 10, 1998

[54] LEISHMANIA ANTIGENS FOR USE IN THE THERAPY AND DIAGNOSIS OF LEISHMANIASIS

[75] Inventors: Steven G. Reed; Antonio Campos-Neto; John R. Webb; Davin C. Dillon; Yasir A. W. Skeiky, all of King, Wash.

[73] Assignee: Corixa Corporation, Seattle, Wash.

[21] Appl. No.: 533,669

[22] Filed: Sep. 22, 1995

[51] Int. Cl.$^6$ .............................. C07K 1/00; C07K 14/00; C07K 17/00; A61K 39/002
[52] U.S. Cl. ......................... 530/350; 530/364; 530/806; 424/269.1; 424/184.1; 930/210
[58] Field of Search .......................... 930/210; 424/269.1; 530/350, 364, 806

[56] References Cited

PUBLICATIONS

Bixler et al, ©1987, In: Synthetic Vaccines Ed. Arnon. pp. 39–71.

Houghten 1986 Vaccines 86, pp. 21–25.

Bowie et al, 1990. Science, 247:1306–1310.

Skeiky et al., "A Recombinant *Leishmania* Antigen that Stimulates Human Peripheral Blood Mononuclear Cells to Express a Th1-Type Cytokine Profile and to Produce Interleukin 12," *Journal of Experimental Medicine* 181(4): 1527–1537, 1995.

Skeiky et al., "Proliferative and Cytokine Responses of Human PBMC to Cloned *Leishmania Braziliensis* Heat shock and Ribosomal Antigens,", *Journal of Immunology* 150(8 pt. 2): 93A, Abstract #517, 1993.

Shapira and Pedraza, "Sequence analysis and transcriptional activation of heat shock protein 83 of *Leishmania mexicana amazonensis*," *Molecular and Biochemical Parasitology* 42(2): 247–255, 1990.

De Andrade et al., "Recombinant *Leishmania* Hs90 and Hsp70 Are Recognized by Sera from Visceral Leishmaniasis Patients but Not Chagas' Disease Patients," *Journal of Clinical Microbiology* 30(2): 330–5, 1992.

Mougneau et al., "Expression Cloning of a Protective *Leishmania* Antigen, " *Science* 268: 563–566, 1995.

Campos–Neto et al, "Cloning and Expression of a *Leishmania donovani* Gene Instructed by a Peptide Isolated from Major Histocompatibility Complex Class II Molecules of Infected Macrophages," *Journal of Experimental Medicine* 182(5): 1423–1433, 1995.

EMBL Database Entry LDP23CSPR, Accession No. X86551, "L. donovani mRNA for 23 kDa cell surface protein," Apr. 26, 1995.

Pir2 Database, Accession No. S54162, "Leishmania donovani," Jul. 8, 1995.

Frommel et al., "Vaccine–Induced Immunity against Cutaneous Leishmaniasis in BALB/c Mice,"*Infection and Immunity* 56(4): 843–848, 1988.

Dillon et al., "Characterization of a *Leishmania tropica* antigen that detects immune reponses in Desert Storm viscerotropic leishmaniasis patients," *Proc. Natl. Acad. Sci. USA* 92: 7981–7985, 1995.

*Primary Examiner*—Nita Minnifield
*Attorney, Agent, or Firm*—Seed and Berry LLP

[57] ABSTRACT

Compositions and methods for preventing, treating and detecting leishmaniasis and stimulating immune responses in patients are disclosed. The compounds provided include polypeptides that contain at least an immunogenic portion of one or more Leishmania antigens, or a variant thereof. Vaccines and pharmaceutical compositions comprising such polypeptides are also provided and may be used, for example, for the prevention and therapy of leishmaniasis, as well as for the detection of Leishmania infection.

2 Claims, 19 Drawing Sheets

```
                                                  ----------------------------------------------------SLTDPAVLGEETHLRVRVVPDKANKTLTVEDNGIGMTK  85
                    MTETFAFQAEINQLMSLIINTFYSNKEIFLRDVISNASDACDKIRYQ.........DA.R.C........E..............  85
                    .............................................EL.....NQ....D.S...I.............T......  85
MPEETQTQDQPMEEEEV..........A.....................EL...S...L.....E.....SK.DSGKE.HINLI.N.QDRA..IV.T......  100

P                                    P
ADLVNNLGTIARSGTKAFMEALEAGGDMSMIGQFGVGFYSAYLVADRVTVVSKNNSDEAY-WESSAGGTFTITSVQESDMKRGTSTTLHLKEDQQEYLEE  184
.............................A................T......V.V.............AP.....LPARI........L....A  185
.E...........................................................D....T..........V.PTPDC.L....RIV............  185
...I........K.........Q..A.I...........EK...IT.H.D..Q.A.......S..VRTDTGEP.G...KVI.......T.....  200

RRVKELIKKHSEFIGYDIELMVEKTAEKEVTDE----DEEEDESKKKSCGDEGEPKVEEVTEGG-ED-KKKKTKKVKEVKKT-YEVK---NKHKPLWTRD  274
..L.......................T.......----...---A..ADE.GE..........-E..-........T.E-...Q---.........  272
..L.D................AT......----..D.--AAATKNEEGE..........KDDAE.GE..........TQE-FV.Q---.........  275
..I..IV....Q....P.T.F...ERD...S.DEAEEK.DKE.E.E.EEKESEDKPEI.DVGSDE..E..DGD..K.KKI.EK.ID.EEL..T..I...N  300

┌—Lbhsp83b
TKDVTKEEYAAFYKAISNDWEDTAATKHFSVEGQLEFRAIAFVPKRAPFDMFEPNKKRNNIKLYVRRVFIMDNCEDLCPDWLGFVKGVVDSEDLPLNISR  374
P.............................PP.............M.............L....................................  372
P...........................EPLS.............L.............S.....................E..A..R........  375
PD.I.N...GE...SLT.....HL.V............LL..R.....L..NR..K................E.I.EY.N.IR............  400

ENLQQNKILKVIRKNIVKKCLELFEEIAENKEDYKQFYEQFGKNIKLGIHEDTANRKKLMELLRFYSTESGEEMTTLKDYVTRMKPEQKSIYYITGDSKK  474
............................M..V..........................V....................A..N..........  472
............A..........K......V.......S..........H.S....D...........EG..C...V......  475
.M..S........L........T.L..D..N..K.....S..........SQ.....S....Y.TSA..D..VS....C....EN..H......ET.D  500

KLESSPFIEKARRCGLEVLFMTEPIDEYVMQQVKDFEDKKFACLTKEGVHFEESEEEKKQREEKKAACEKLCKTMKEVLGDKVEKVTVSERLLTSPCILV  574
.........Q.K.R.F..........Y..........................................E..T...............S.......  572
...T.....Q..R.F..........I............................T.......E.T.Y.R...A.D.........V....A.....  575
QVAN.A.V.RL.KH....IY.I......CV..L.E..G.TLVSV....LELP.D.....KQ....TKF.N...I..DI.EK.....V..N..V....C..  600

P
TSEFGWSAHMEQIMRNQALRDSSMAQYMVSKKTMEVNPDHPIIKELRRRVEADENDKAVKDLVFLLFDTSLLTSGFQLDDPTGYAERINRMIKLGLSLDE  674
................M.............M....L.K.............................................E...-........  671
..............SA.M........I..A...V...K...............Y....A......T....S.....H..........D  675
..TY..T..N..R..KA.....N.TMG..AA..HL.I....S..ET..QKA...K...S.....I..YE.A..S...S.E..QTH.N..Y.......GI..  700

EE--EEVA-EAPPAEAAPAEVTAGTSSMEQVD  703   Lbhsp83
..E--.E.V..AV..T............L..  701   Lahsp83
.D---NGNE..E..A.V....PV.........  704   Tchsp83
DDPTADDTSA.VTE.MP.L.GDDD..R..E..  734   Huhsp89
```

*Fig. 19*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 3134 base pairs
        ( B ) TYPE: nucleic acid
        ( C ) STRANDEDNESS: single
        ( D ) TOPOLOGY: linear ( i x ) FEATURE:
        ( A ) NAME/KEY: CDS ( B ) LOCATION: 421..2058

( x i ) SEQUENCE DESCRIPTION: SKEQ ID NO:1:

| | | |
|---|---|---|
| CAAGTGTCGA AGGACAGTGT TCNCCGTGTG AGATCGCCGG CTGTGCGTGT GAAGGCGGTG | 6 |
| CCATCGGANA AACAACACCG GTGGANCCGC AGGAAACCAT CTTTCTCCGC AGGTCTCTTT | 12 |
| TTGTTGTCGA TTGAGAGTGC NCCAAACCCT GCTGGTGCCC TTCTCACATA TCATGTTTTT | 18 |
| CGTTGTGCGC TCGCTTTGCC TTTCCTCTCC TTTCCCTCTC TTCCGTGGTG CCGTGTATAC | 24 |
| TTCTGGCACC CGCTACGTCA CTTCGCTGGT TTGAACAGAA CCACTGTGAA CACCCACGGG | 30 |
| CGATCGCACA CATACACATC CCTCACTCAC ACACACAGCT ACATCTATCC TACATAAAGC | 36 |
| TGAAAAAAAA GTCTACGAAC AATTTGTTT TTACAGTGCG TTGCCGCACA TTTCTCCGTA | 42 |

```
ATG  GAC  GCA  ACT  GAG  CTG  AAG  AAC  AAG  GGG  AAC  GAA  GAG  TTC  TCC  GCC       46
Met  Asp  Ala  Thr  Glu  Leu  Lys  Asn  Lys  Gly  Asn  Glu  Glu  Phe  Ser  Ala
 1                   5                        10                       15

GGC  CGC  TAT  GTG  GAG  GCG  GTG  AAC  TAC  TTC  TCA  AAG  GCG  ATC  CAG  TTG       51
Gly  Arg  Tyr  Val  Glu  Ala  Val  Asn  Tyr  Phe  Ser  Lys  Ala  Ile  Gln  Leu
                    20                        25                       30

GAT  GAG  CAG  AAC  AGT  GTC  CTC  TAC  AGC  AAC  CGC  TCC  GCC  TGT  TTT  GCA       56
Asp  Glu  Gln  Asn  Ser  Val  Leu  Tyr  Ser  Asn  Arg  Ser  Ala  Cys  Phe  Ala
                    35                        40                       45

GCC  ATG  CAG  AAA  TAC  AAG  GAC  GCG  CTG  GAC  GAC  GCC  GAC  AAG  TGC  ATC       61
Ala  Met  Gln  Lys  Tyr  Lys  Asp  Ala  Leu  Asp  Asp  Ala  Asp  Lys  Cys  Ile
             50                        55                       60

TCG  ATC  AAG  CCG  AAT  TGG  GCC  AAG  GGC  TAC  GTG  CGC  CGA  GGA  GCA  GCT       66
Ser  Ile  Lys  Pro  Asn  Trp  Ala  Lys  Gly  Tyr  Val  Arg  Arg  Gly  Ala  Ala
 65                       70                        75                       80

CTC  CAT  GGC  ATG  CGC  CGC  TAC  GAC  GAT  GCC  ATT  GCC  GCG  TAT  GAA  AAG       70
Leu  His  Gly  Met  Arg  Arg  Tyr  Asp  Asp  Ala  Ile  Ala  Ala  Tyr  Glu  Lys
                    85                        90                       95

GGG  CTC  AAG  GTG  GAC  CCT  TCC  AAC  AGC  GGC  TGC  GCG  CAG  GGC  GTG  AAG       75
Gly  Leu  Lys  Val  Asp  Pro  Ser  Asn  Ser  Gly  Cys  Ala  Gln  Gly  Val  Lys
                   100                       105                      110

GAC  GTG  CAG  GTA  GCC  AAG  GCC  CGC  GAA  GCA  CGT  GAC  CCC  ATC  GCT  CGC       80
Asp  Val  Gln  Val  Ala  Lys  Ala  Arg  Glu  Ala  Arg  Asp  Pro  Ile  Ala  Arg
             115                       120                      125

GTC  TTC  ACC  CCG  GAG  GCG  TTC  CGC  AAG  ATC  CAA  GAG  AAT  CCC  AAG  CTG       85
Val  Phe  Thr  Pro  Glu  Ala  Phe  Arg  Lys  Ile  Gln  Glu  Asn  Pro  Lys  Leu
             130                       135                      140

TCT  CTA  CTT  ATG  CTG  CAG  CCG  GAC  TAC  GTG  AAG  ATG  GTA  GAC  ACC  GTC       90
Ser  Leu  Leu  Met  Leu  Gln  Pro  Asp  Tyr  Val  Lys  Met  Val  Asp  Thr  Val
145                       150                      155                      160

ATC  CGC  GAC  CCT  TCG  CAG  GGC  CGG  CTG  TAC  ATG  GAA  GAC  CAG  CGC  TTT       94
Ile  Arg  Asp  Pro  Ser  Gln  Gly  Arg  Leu  Tyr  Met  Glu  Asp  Gln  Arg  Phe
                   165                       170                      175

GCC  CTG  ACG  CTC  ATG  TAC  CTG  AGC  GGA  ATG  AAG  ATT  CCC  AAC  GAT  GGT       99
Ala  Leu  Thr  Leu  Met  Tyr  Leu  Ser  Gly  Met  Lys  Ile  Pro  Asn  Asp  Gly
                   180                       185                      190

GAT  GGC  GAG  GAG  GAG  GAA  CGT  CCG  TCT  GCG  AAG  GCG  GCA  GAG  ACA  GCG       104
Asp  Gly  Glu  Glu  Glu  Glu  Arg  Pro  Ser  Ala  Lys  Ala  Ala  Glu  Thr  Ala
             195                       200                      205

AAG  CCA  AAA  GAG  GAG  AAG  CCT  CTC  ACC  GAC  AAC  GAG  AAG  GAG  GCC  CTG       109
Lys  Pro  Lys  Glu  Glu  Lys  Pro  Leu  Thr  Asp  Asn  Glu  Lys  Glu  Ala  Leu
210                       215                      220

GCG  CTC  AAG  GAG  GAG  GGC  AAC  AAG  CTG  TAC  CTC  TCG  AAG  AAG  TTT  GAG       114
Ala  Leu  Lys  Glu  Glu  Gly  Asn  Lys  Leu  Tyr  Leu  Ser  Lys  Lys  Phe  Glu
225                       230                      235                      240

GAG  GCG  CTG  ACC  AAG  TAC  CAA  GAG  GCG  CAG  GTG  AAA  GAC  CCC  AAC  AAC       118
Glu  Ala  Leu  Thr  Lys  Tyr  Gln  Glu  Ala  Gln  Val  Lys  Asp  Pro  Asn  Asn
```

```
                        245                              250                              255
ACT  TTA  TAC  ATT  CTG  AAC  GTG  TCG  GCC  GTG  TAC  TTC  GAG  CAG  GGT  GAC        123
Thr  Leu  Tyr  Ile  Leu  Asn  Val  Ser  Ala  Val  Tyr  Phe  Glu  Gln  Gly  Asp
          260                         265                         270

TAC  GAC  AAG  TGC  ATC  GCC  GAG  TGC  GAG  CAC  GGT  ATC  GAG  CAC  GGT  CGC        128
Tyr  Asp  Lys  Cys  Ile  Ala  Glu  Cys  Glu  His  Gly  Ile  Glu  His  Gly  Arg
               275                         280                         285

GAG  AAC  CAC  TGC  GAC  TAC  ACA  ATC  ATT  GCG  AAG  CTC  ATG  ACC  CGG  AAC        133
Glu  Asn  His  Cys  Asp  Tyr  Thr  Ile  Ile  Ala  Lys  Leu  Met  Thr  Arg  Asn
     290                         295                         300

GCC  TTG  TGC  CTC  CAG  AGG  CAG  AGG  AAG  TAC  GAG  GCT  GCT  ATC  GAC  CTT        138
Ala  Leu  Cys  Leu  Gln  Arg  Gln  Arg  Lys  Tyr  Glu  Ala  Ala  Ile  Asp  Leu
305                      310                         315                      320

TAC  AAG  CGC  GCC  CTT  GTC  GAG  TGG  CGT  AAC  CCT  GAC  ACC  CTC  AAG  AAG        142
Tyr  Lys  Arg  Ala  Leu  Val  Glu  Trp  Arg  Asn  Pro  Asp  Thr  Leu  Lys  Lys
                         325                         330                         335

CTG  ACG  GAG  TGC  GAG  AAG  GAG  CAC  CAA  AAG  GCG  GTG  GAG  GAA  GCC  TAC        147
Leu  Thr  Glu  Cys  Glu  Lys  Glu  His  Gln  Lys  Ala  Val  Glu  Glu  Ala  Tyr
               340                         345                         350

ATC  GAT  CCT  GAG  ATC  GCG  AAG  CAG  AAG  AAA  GAC  GAA  GGT  AAC  CAG  TAC        152
Ile  Asp  Pro  Glu  Ile  Ala  Lys  Gln  Lys  Lys  Asp  Glu  Gly  Asn  Gln  Tyr
          355                         360                         365

TTC  AAG  GAG  GAT  AAG  TTC  CCC  GAG  GCC  GTG  GCA  GCG  TAC  ACG  GAG  GCC        157
Phe  Lys  Glu  Asp  Lys  Phe  Pro  Glu  Ala  Val  Ala  Ala  Tyr  Thr  Glu  Ala
     370                         375                         380

ATC  AAG  CGC  AAC  CCT  GCC  GAG  CAC  ACC  TCC  TAC  AGC  AAT  CGC  GCG  GCC        162
Ile  Lys  Arg  Asn  Pro  Ala  Glu  His  Thr  Ser  Tyr  Ser  Asn  Arg  Ala  Ala
385                      390                         395                      400

GCG  TAC  ATC  AAG  CTT  GGA  GCC  TTC  AAC  GAC  GCC  CTC  AAG  GAC  GCG  GAG        166
Ala  Tyr  Ile  Lys  Leu  Gly  Ala  Phe  Asn  Asp  Ala  Leu  Lys  Asp  Ala  Glu
                         405                         410                         415

AAG  TGC  ATT  GAG  CTG  AAG  CCC  GAC  TTT  GTT  AAG  GGC  TAC  GCG  CGC  AAG        171
Lys  Cys  Ile  Glu  Leu  Lys  Pro  Asp  Phe  Val  Lys  Gly  Tyr  Ala  Arg  Lys
               420                         425                         430

GGT  CAT  GCT  TAC  TTT  TGG  ACC  AAG  CAG  TAC  AAC  CGC  GCG  CTG  CAG  GCG        176
Gly  His  Ala  Tyr  Phe  Trp  Thr  Lys  Gln  Tyr  Asn  Arg  Ala  Leu  Gln  Ala
          435                         440                         445

TAC  GAT  GAG  GGC  CTC  AAG  GTG  GAC  CCG  AGC  AAT  GCG  GAC  TGC  AAG  GAT        181
Tyr  Asp  Glu  Gly  Leu  Lys  Val  Asp  Pro  Ser  Asn  Ala  Asp  Cys  Lys  Asp
     450                         455                         460

GGG  CGG  TAT  CGC  ACA  ATC  ATG  AAG  ATT  CAG  GAG  ATG  GCA  TCT  GGC  CAA        186
Gly  Arg  Tyr  Arg  Thr  Ile  Met  Lys  Ile  Gln  Glu  Met  Ala  Ser  Gly  Gln
465                      470                         475                      480

TCC  GCG  GAT  GGC  GAC  GAG  GCG  GCG  CGC  CGG  GCC  ATG  GAC  GAT  CCT  GAA        190
Ser  Ala  Asp  Gly  Asp  Glu  Ala  Ala  Arg  Arg  Ala  Met  Asp  Asp  Pro  Glu
                         485                         490                         495

ATC  GCG  GCA  ATC  ATG  CAA  GAT  AGC  TAC  ATG  CAA  CTA  GTG  TTG  AAG  GAG        195
Ile  Ala  Ala  Ile  Met  Gln  Asp  Ser  Tyr  Met  Gln  Leu  Val  Leu  Lys  Glu
               500                         505                         510

ATG  CAG  AAC  GAT  CCC  ACG  CGC  ATT  CAG  GAG  TAC  ATG  AAG  GAC  TCC  GGG        200
Met  Gln  Asn  Asp  Pro  Thr  Arg  Ile  Gln  Glu  Tyr  Met  Lys  Asp  Ser  Gly
          515                         520                         525

ATC  TCA  TCG  AAG  ATC  AAC  AAG  CTG  ATT  TCA  GCT  GGC  ATC  ATT  CGT  TTT        205
Ile  Ser  Ser  Lys  Ile  Asn  Lys  Leu  Ile  Ser  Ala  Gly  Ile  Ile  Arg  Phe
     530                         535                         540

GGT  CAG  TAGACTTCTA  CGCTGCCTCA  TCTTTTCCGT  GTCTTTGCGT  CGGCGGGTAT              210
Gly  Gln
545

CGTAAAGCAC  AATAAAGCAG  CGATTCACAT  GCACGAGTAA  AGTGCTGCGC  CTCTCAAACA              216
```

```
CGACGTCGAG  GCTGTGGTGC  AGATGCGCGT  CCTGCATGAA  GGTAGTGAAG  AGGAAAGTAA      2 2 2

GGGATGTTGT  TTGTGGGCCT  TCGTGGCTGC  GCACACACCT  CTTATCTCCT  TCGCTTGGTA      2 2 8

CCTTCTCCCT  TTTTCGTCTT  CACCCCCCTT  TCTCTTCTCA  CGCTCTCCCT  GGCGCGGTGG      2 3 4

TGCAACGATT  TCGTTTTATT  TACGTCTGTG  TAGCTCCTCT  ATTCAACGGT  GCGATGACGC      2 4 0

TAACGAAGCT  GGCCTGTATT  CGGCTAAGGC  GAAGGCAAAA  GACTAGGAGG  GGGGGGGGAA      2 4 6

GGAGACGGCG  TGACCATCAC  TGCGAAGAAA  CAAGCCGAAG  AAAAGGCCCC  GAACGCCTGC      2 5 2

ATTTCCGCGC  GCCCTCGCCC  GCCTTCCTTC  CTTCCTTCGC  TCTCTCTCTC  TCTCTCTCTC      2 5 8

GCTATCTTCT  CAACGGAGAC  ATGAAAGGCG  TTTGTTAGGA  AAAGAGGGGG  GGGGGAAGAG      2 6 4

TGGGACGACG  CGCTGCGTCT  TTTGGGCACT  GGTCACGTGC  GTCACCCTCT  TTTTTTATCT      2 7 0

CTATTGGCAC  TGTCTTGTTT  CTTTTCCCTT  TCCTATCATA  CGCGTCTCGC  AAACGACTCC      2 7 6

GCGCTGAGCA  GCCATGTGCT  GCGGCGTGGA  GGAAGTACAC  AGACATCACG  GATGCATATG      2 8 2

TGCGCGTCCG  TGTACGCGCT  TGTATGGGGC  TTCTAACAGC  GCCTGTGTGT  GTTTGTGTGT      2 8 8

GTGTGTGTGT  GTGTGTCTGT  GTATTTCGAG  CGTCTGTATG  CTATTCTATT  AAGCACCGAA      2 9 4

GAAGAGACAC  ACACGACAGC  GAAGGAGATG  GTGTCGGCTT  TTCGGCTAAT  CACTCCCTTC      3 0 0

CATAGCTTCT  CTGAAGGAGG  CTCTCTTCCA  GAGGAATAGA  CTGCAGATGG  GGTCCACGTT      3 0 6

TATCTGAGGA  GTCAACGGAA  AAAAAAAAA   AAAAAAAAA   AAAAAAAAA   AAAAAAAAA       3 1 2

CTCGAG                                                                      3 1 3
```

( 2 ) INFORMATION FOR SEQ ID NO:2:

( i ) SEQUENCE CHARACTERISTICS:
        ( A ) LENGTH: 546 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Ala  Thr  Glu  Leu  Lys  Asn  Lys  Gly  Asn  Glu  Glu  Phe  Ser  Ala
 1              5                        10                       15

Gly  Arg  Tyr  Val  Glu  Ala  Val  Asn  Tyr  Phe  Ser  Lys  Ala  Ile  Gln  Leu
              20                       25                       30

Asp  Glu  Gln  Asn  Ser  Val  Leu  Tyr  Ser  Asn  Arg  Ser  Ala  Cys  Phe  Ala
         35                       40                       45

Ala  Met  Gln  Lys  Tyr  Lys  Asp  Ala  Leu  Asp  Asp  Ala  Asp  Lys  Cys  Ile
    50                       55                       60

Ser  Ile  Lys  Pro  Asn  Trp  Ala  Lys  Gly  Tyr  Val  Arg  Arg  Gly  Ala  Ala
 65                       70                       75                       80

Leu  His  Gly  Met  Arg  Arg  Tyr  Asp  Asp  Ala  Ile  Ala  Ala  Tyr  Glu  Lys
                  85                       90                       95

Gly  Leu  Lys  Val  Asp  Pro  Ser  Asn  Ser  Gly  Cys  Ala  Gln  Gly  Val  Lys
                 100                      105                      110

Asp  Val  Gln  Val  Ala  Lys  Ala  Arg  Glu  Ala  Arg  Asp  Pro  Ile  Ala  Arg
             115                      120                      125

Val  Phe  Thr  Pro  Glu  Ala  Phe  Arg  Lys  Ile  Gln  Glu  Asn  Pro  Lys  Leu
         130                      135                      140

Ser  Leu  Leu  Met  Leu  Gln  Pro  Asp  Tyr  Val  Lys  Met  Val  Asp  Thr  Val
145                      150                      155                      160

Ile  Arg  Asp  Pro  Ser  Gln  Gly  Arg  Leu  Tyr  Met  Glu  Asp  Gln  Arg  Phe
                 165                      170                      175

Ala  Leu  Thr  Leu  Met  Tyr  Leu  Ser  Gly  Met  Lys  Ile  Pro  Asn  Asp  Gly
```

|   |   |   |   |   | 180 |   |   |   |   | 185 |   |   |   |   | 190 |   |
|---|---|---|---|---|---|---|---|---|---|---|---|---|---|---|---|---|

Asp Gly Glu Glu Glu Arg Pro Ser Ala Lys Ala Ala Glu Thr Ala
     195              200             205

Lys Pro Lys Glu Glu Lys Pro Leu Thr Asp Asn Glu Lys Glu Ala Leu
210               215            220

Ala Leu Lys Glu Glu Gly Asn Lys Leu Tyr Leu Ser Lys Lys Phe Glu
225               230          235           240

Glu Ala Leu Thr Lys Tyr Gln Glu Ala Gln Val Lys Asp Pro Asn Asn
            245          250           255

Thr Leu Tyr Ile Leu Asn Val Ser Ala Val Tyr Phe Glu Gln Gly Asp
      260           265           270

Tyr Asp Lys Cys Ile Ala Glu Cys Glu His Gly Ile Glu His Gly Arg
     275          280           285

Glu Asn His Cys Asp Tyr Thr Ile Ile Ala Lys Leu Met Thr Arg Asn
    290           295           300

Ala Leu Cys Leu Gln Arg Gln Arg Lys Tyr Glu Ala Ala Ile Asp Leu
305             310          315          320

Tyr Lys Arg Ala Leu Val Glu Trp Arg Asn Pro Asp Thr Leu Lys Lys
          325         330           335

Leu Thr Glu Cys Glu Lys Glu His Gln Lys Ala Val Glu Glu Ala Tyr
        340         345         350

Ile Asp Pro Glu Ile Ala Lys Gln Lys Lys Asp Glu Gly Asn Gln Tyr
      355          360         365

Phe Lys Glu Asp Lys Phe Pro Glu Ala Val Ala Ala Tyr Thr Glu Ala
   370          375           380

Ile Lys Arg Asn Pro Ala Glu His Thr Ser Tyr Ser Asn Arg Ala Ala
385             390          395          400

Ala Tyr Ile Lys Leu Gly Ala Phe Asn Asp Ala Leu Lys Asp Ala Glu
          405         410           415

Lys Cys Ile Glu Leu Lys Pro Asp Phe Val Lys Gly Tyr Ala Arg Lys
        420         425         430

Gly His Ala Tyr Phe Trp Thr Lys Gln Tyr Asn Arg Ala Leu Gln Ala
      435         440          445

Tyr Asp Glu Gly Leu Lys Val Asp Pro Ser Asn Ala Asp Cys Lys Asp
450              455          460

Gly Arg Tyr Arg Thr Ile Met Lys Ile Gln Glu Met Ala Ser Gly Gln
465             470          475        480

Ser Ala Asp Gly Asp Glu Ala Ala Arg Ala Met Asp Asp Pro Glu
            485         490           495

Ile Ala Ala Ile Met Gln Asp Ser Tyr Met Gln Leu Val Leu Lys Glu
        500         505          510

Met Gln Asn Asp Pro Thr Arg Ile Gln Glu Tyr Met Lys Asp Ser Gly
    515           520          525

Ile Ser Ser Lys Ile Asn Lys Leu Ile Ser Ala Gly Ile Ile Arg Phe
   530          535          540

Gly Gln
545

( 2 ) INFORMATION FOR SEQ ID NO:3:

( i ) SEQUENCE CHARACTERISTICS:
        ( A ) LENGTH: 676 base pairs
        ( B ) TYPE: nucleic acid
        ( C ) STRANDEDNESS: single
        ( D ) TOPOLOGY: linear ( i x ) FEATURE:
  ( A ) NAME/KEY: CDS
  ( B ) LOCATION: 26..550

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| AATTCGGCAC | GAGGCATTGT | GCATA | ATG | GTC | AAG | TCC | CAC | TAC | ATC | TGC | GCG | | | | | 52 |
| | | | Met | Val | Lys | Ser | His | Tyr | Ile | Cys | Ala | | | | | |
| | | | | | | 550 | | | | | 555 | | | | | |

| GGC | CGC | CTG | GTG | CGC | ATC | CTG | CGT | GGC | CCC | CGC | CAG | GAC | CGC | GTT | GGT | 100 |
|---|---|---|---|---|---|---|---|---|---|---|---|---|---|---|---|---|
| Gly | Arg | Leu | Val | Arg | Ile | Leu | Arg | Gly | Pro | Arg | Gln | Asp | Arg | Val | Gly | |
| | | | | 560 | | | | | 565 | | | | | 570 | | |

| GTG | ATC | GTC | GAC | ATT | GTC | GAC | GCG | AAC | CGC | GTG | CTG | GTG | GAG | AAC | CCG | 148 |
|---|---|---|---|---|---|---|---|---|---|---|---|---|---|---|---|---|
| Val | Ile | Val | Asp | Ile | Val | Asp | Ala | Asn | Arg | Val | Leu | Val | Glu | Asn | Pro | |
| | | | 575 | | | | | 580 | | | | | 585 | | | |

| GAG | GAC | GCG | AAG | ATG | TGG | CGC | CAC | GTG | CAG | AAC | CTG | AAG | AAC | GTG | GAG | 196 |
|---|---|---|---|---|---|---|---|---|---|---|---|---|---|---|---|---|
| Glu | Asp | Ala | Lys | Met | Trp | Arg | His | Val | Gln | Asn | Leu | Lys | Asn | Val | Glu | |
| | | | 590 | | | | | 595 | | | | | 600 | | | |

| CCG | CTG | AAG | TAC | TGC | GTG | AGC | GTC | AGC | CGC | AAC | TGC | AGC | GCG | AAG | GCG | 244 |
|---|---|---|---|---|---|---|---|---|---|---|---|---|---|---|---|---|
| Pro | Leu | Lys | Tyr | Cys | Val | Ser | Val | Ser | Arg | Asn | Cys | Ser | Ala | Lys | Ala | |
| | | 605 | | | | | 610 | | | | | 615 | | | | |

| CTG | AAG | GAT | GCG | CTG | GCC | TCG | TCG | AAG | GCG | CTG | GAG | AAG | TAC | GCG | AAG | 292 |
|---|---|---|---|---|---|---|---|---|---|---|---|---|---|---|---|---|
| Leu | Lys | Asp | Ala | Leu | Ala | Ser | Ser | Lys | Ala | Leu | Glu | Lys | Tyr | Ala | Lys | |
| 620 | | | | | 625 | | | | | 630 | | | | | 635 | |

| ACG | CGC | ACT | GCT | GCG | CGC | GTG | GAG | GCG | AAG | AAG | GCG | TGC | GCC | GCG | TCG | 340 |
|---|---|---|---|---|---|---|---|---|---|---|---|---|---|---|---|---|
| Thr | Arg | Thr | Ala | Ala | Arg | Val | Glu | Ala | Lys | Lys | Ala | Cys | Ala | Ala | Ser | |
| | | | | 640 | | | | | 645 | | | | | 650 | | |

| ACG | GAC | TTC | GAG | CGC | TAC | CAG | CTG | CGC | GTT | GCG | CGC | CGT | TCT | CGC | GCG | 388 |
|---|---|---|---|---|---|---|---|---|---|---|---|---|---|---|---|---|
| Thr | Asp | Phe | Glu | Arg | Tyr | Gln | Leu | Arg | Val | Ala | Arg | Arg | Ser | Arg | Ala | |
| | | | 655 | | | | | 660 | | | | | 665 | | | |

| CAC | TGG | GCG | CGC | AAG | GTG | TTC | GAC | GAG | AAG | GAC | GCG | AAG | ACG | CCC | GTG | 436 |
|---|---|---|---|---|---|---|---|---|---|---|---|---|---|---|---|---|
| His | Trp | Ala | Arg | Lys | Val | Phe | Asp | Glu | Lys | Asp | Ala | Lys | Thr | Pro | Val | |
| | | 670 | | | | | 675 | | | | | 680 | | | | |

| TCG | TGG | CAC | AAG | GTT | GCG | CTG | AAG | AAG | ATG | CAG | AAG | AAG | GCC | GCA | AAG | 484 |
|---|---|---|---|---|---|---|---|---|---|---|---|---|---|---|---|---|
| Ser | Trp | His | Lys | Val | Ala | Leu | Lys | Lys | Met | Gln | Lys | Lys | Ala | Ala | Lys | |
| | 685 | | | | | 690 | | | | | 695 | | | | | |

| ATG | GAC | TCG | ACC | GAG | GGC | GCT | AAG | AGG | CGC | ATG | CAG | AAG | GCG | ATC | GCT | 532 |
|---|---|---|---|---|---|---|---|---|---|---|---|---|---|---|---|---|
| Met | Asp | Ser | Thr | Glu | Gly | Ala | Lys | Arg | Arg | Met | Gln | Lys | Ala | Ile | Ala | |
| 700 | | | | | 705 | | | | | 710 | | | | | 715 | |

| GCC | CGC | AAG | GCG | AAA | AAG | TAAGGCCATA | CCCTCACTTC | GCTTGTTTCG | 580 |
|---|---|---|---|---|---|---|---|---|---|
| Ala | Arg | Lys | Ala | Lys | Lys | | | | |
| | | | | 720 | | | | | |

TGATTTTTCG TGGGAGTCGG TGGCCCTACC AGCGGTCTTT CATTGGCTTA TTTCTATCCG    640

GTCTGAAAGA GGTACAAAAA AAAAAAAAAA AAAAAA    676

( 2 ) INFORMATION FOR SEQ ID NO:4:

( i ) SEQUENCE CHARACTERISTICS:
    ( A ) LENGTH: 175 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met | Val | Lys | Ser | His | Tyr | Ile | Cys | Ala | Gly | Arg | Leu | Val | Arg | Ile | Leu |
|---|---|---|---|---|---|---|---|---|---|---|---|---|---|---|---|
| 1 | | | | 5 | | | | | 10 | | | | | 15 | |

| Arg | Gly | Pro | Arg | Gln | Asp | Arg | Val | Gly | Val | Ile | Val | Asp | Ile | Val | Asp |
|---|---|---|---|---|---|---|---|---|---|---|---|---|---|---|---|
| | | | 20 | | | | | 25 | | | | | 30 | | |

| Ala | Asn | Arg | Val | Leu | Val | Glu | Asn | Pro | Glu | Asp | Ala | Lys | Met | Trp | Arg |
|---|---|---|---|---|---|---|---|---|---|---|---|---|---|---|---|
| | | 35 | | | | | 40 | | | | | 45 | | | |

| His | Val | Gln | Asn | Leu | Lys | Asn | Val | Glu | Pro | Leu | Lys | Tyr | Cys | Val | Ser |
|---|---|---|---|---|---|---|---|---|---|---|---|---|---|---|---|

```
              50                        55                         60
Val Ser Arg Asn Cys Ser Ala Lys Ala Leu Lys Asp Ala Leu Ala Ser
 65              70                      75                      80

Ser Lys Ala Leu Glu Lys Tyr Ala Lys Thr Arg Thr Ala Ala Arg Val
                 85                      90                      95

Glu Ala Lys Lys Ala Cys Ala Ala Ser Thr Asp Phe Glu Arg Tyr Gln
                100                     105                     110

Leu Arg Val Ala Arg Arg Ser Arg Ala His Trp Ala Arg Lys Val Phe
            115                     120                     125

Asp Glu Lys Asp Ala Lys Thr Pro Val Ser Trp His Lys Val Ala Leu
        130                     135                     140

Lys Lys Met Gln Lys Lys Ala Ala Lys Met Asp Ser Thr Glu Gly Ala
145                 150                     155                     160

Lys Arg Arg Met Gln Lys Ala Ile Ala Ala Arg Lys Ala Lys Lys
                165                     170                     175
```

( 2 ) INFORMATION FOR SEQ ID NO:5:

( i ) SEQUENCE CHARACTERISTICS:
        ( A ) LENGTH: 2040 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 62..2029

( x i ) SEQUENCE DESCRIPTION: SEQ ID NO:5:

```
CGCGGTGGCG GCCGCTCTAG AACTAGTGGA TCCCCCGGGC TGCAGGAATT CGGCACGAGA         60

G AGC CTG ACG GAC CCG GCG GTG CTG GGC GAG GAG ACT CAC CTG CGC           106
  Ser Leu Thr Asp Pro Ala Val Leu Gly Glu Glu Thr His Leu Arg
                 180                     185                     190

GTC CGC GTG GTG CCG GAC AAG GCG AAC AAG ACG CTG ACG GTG GAG GAT         154
Val Arg Val Val Pro Asp Lys Ala Asn Lys Thr Leu Thr Val Glu Asp
                195                     200                     205

AAC GGC ATC GGC ATG ACC AAG GCG GAC CTC GTG AAC AAT CTG GGC ACG         202
Asn Gly Ile Gly Met Thr Lys Ala Asp Leu Val Asn Asn Leu Gly Thr
            210                     215                     220

ATC GCG CGC TCC GGC ACG AAG GCT TTC ATG GAG GCA CTG GAG GCC GGC         250
Ile Ala Arg Ser Gly Thr Lys Ala Phe Met Glu Ala Leu Glu Ala Gly
        225                     230                     235

GGC GAC ATG AGC ATG ATC GGC CAG TTC GGT GTC GGC TTC TAC TCC GCG         298
Gly Asp Met Ser Met Ile Gly Gln Phe Gly Val Gly Phe Tyr Ser Ala
240                     245                     250

TAC CTT GTG GCG GAC CGC GTG ACG GTG GTG TCG AAG AAC AAC TCG GAC         346
Tyr Leu Val Ala Asp Arg Val Thr Val Val Ser Lys Asn Asn Ser Asp
255                     260                     265                     270

GAG GCG TAC TGG GAA TCG TCT GCG GGG GGC ACG TTC ACC ATC ACG AGC         394
Glu Ala Tyr Trp Glu Ser Ser Ala Gly Gly Thr Phe Thr Ile Thr Ser
                275                     280                     285

GTG CAG GAG TCG GAC ATG AAG CGC GGC ACG AGT ACA ACG CTG CAC CTA         442
Val Gln Glu Ser Asp Met Lys Arg Gly Thr Ser Thr Thr Leu His Leu
            290                     295                     300

AAG GAG GAC CAG CAG GAG TAC CTG GAG GAG CGC CGG GTG AAG GAG CTG         490
Lys Glu Asp Gln Gln Glu Tyr Leu Glu Glu Arg Arg Val Lys Glu Leu
        305                     310                     315

ATC AAG AAG CAC TCC GAG TTC ATC GGC TAC GAC ATC GAG CTG ATG GTG         538
Ile Lys Lys His Ser Glu Phe Ile Gly Tyr Asp Ile Glu Leu Met Val
320                     325                     330
```

| | | | | | | | | | | | | | | | | |
|---|---|---|---|---|---|---|---|---|---|---|---|---|---|---|---|---|
| GAG | AAG | ACG | GCG | GAG | AAG | GAG | GTG | ACG | GAC | GAG | GAC | GAG | GAG | GAG | GAC | 586 |
| Glu | Lys | Thr | Ala | Glu | Lys | Glu | Val | Thr | Asp | Glu | Asp | Glu | Glu | Glu | Asp | |
| 335 | | | | 340 | | | | | 345 | | | | | | 350 | |
| GAG | TCG | AAG | AAG | AAG | TCC | TGC | GGG | GAC | GAG | GGC | GAG | CCG | AAG | GTG | GAG | 634 |
| Glu | Ser | Lys | Lys | Lys | Ser | Cys | Gly | Asp | Glu | Gly | Glu | Pro | Lys | Val | Glu | |
| | | | | 355 | | | | | 360 | | | | | 365 | | |
| GAG | GTG | ACG | GAG | GGC | GGC | GAG | GAC | AAG | AAG | AAG | ACG | AAG | AAG | GTG | | 682 |
| Glu | Val | Thr | Glu | Gly | Gly | Glu | Asp | Lys | Lys | Lys | Thr | Lys | Lys | Val | | |
| | | | 370 | | | | | 375 | | | | | 380 | | | |
| AAG | GAG | GTG | AAG | AAG | ACG | TAC | GAG | GTC | AAG | AAC | AAG | CAC | AAG | CCG | CTC | 730 |
| Lys | Glu | Val | Lys | Lys | Thr | Tyr | Glu | Val | Lys | Asn | Lys | His | Lys | Pro | Leu | |
| | | 385 | | | | | 390 | | | | | 395 | | | | |
| TGG | ACG | CGC | GAC | ACG | AAG | GAC | GTG | ACG | AAG | GAG | GAG | TAC | GCG | GCC | TTC | 778 |
| Trp | Thr | Arg | Asp | Thr | Lys | Asp | Val | Thr | Lys | Glu | Glu | Tyr | Ala | Ala | Phe | |
| | 400 | | | | | 405 | | | | | 410 | | | | | |
| TAC | AAG | GCC | ATC | TCC | AAC | GAC | TGG | GAG | GAC | ACG | GCG | GCG | ACG | AAG | CAC | 826 |
| Tyr | Lys | Ala | Ile | Ser | Asn | Asp | Trp | Glu | Asp | Thr | Ala | Ala | Thr | Lys | His | |
| 415 | | | | | 420 | | | | | 425 | | | | | 430 | |
| TTC | TCG | GTG | GAG | GGC | CAG | CTG | GAG | TTC | CGC | GCG | ATC | GCG | TTC | GTG | CCG | 874 |
| Phe | Ser | Val | Glu | Gly | Gln | Leu | Glu | Phe | Arg | Ala | Ile | Ala | Phe | Val | Pro | |
| | | | | 435 | | | | | 440 | | | | | 445 | | |
| AAG | CGC | GCG | CCG | TTC | GAC | ATG | TTC | GAG | CCG | AAC | AAG | AAG | CGC | AAC | AAC | 922 |
| Lys | Arg | Ala | Pro | Phe | Asp | Met | Phe | Glu | Pro | Asn | Lys | Lys | Arg | Asn | Asn | |
| | | | 450 | | | | | 455 | | | | | 460 | | | |
| ATC | AAG | CTG | TAC | GTG | CGC | CGC | GTG | TTC | ATC | ATG | GAC | AAC | TGC | GAG | GAC | 970 |
| Ile | Lys | Leu | Tyr | Val | Arg | Arg | Val | Phe | Ile | Met | Asp | Asn | Cys | Glu | Asp | |
| | | 465 | | | | | 470 | | | | | 475 | | | | |
| CTG | TGC | CCG | GAC | TGG | CTC | GGC | TTC | GTG | AAG | GGC | GTC | GTG | GAC | AGC | GAG | 1018 |
| Leu | Cys | Pro | Asp | Trp | Leu | Gly | Phe | Val | Lys | Gly | Val | Val | Asp | Ser | Glu | |
| | 480 | | | | | 485 | | | | | 490 | | | | | |
| GAC | CTG | CCG | CTG | AAC | ATC | TCG | CGC | GAG | AAC | CTG | CAG | CAG | AAC | AAG | ATC | 1066 |
| Asp | Leu | Pro | Leu | Asn | Ile | Ser | Arg | Glu | Asn | Leu | Gln | Gln | Asn | Lys | Ile | |
| 495 | | | | | 500 | | | | | 505 | | | | | 510 | |
| CTG | AAG | GTG | ATC | CGC | AAG | AAC | ATC | GTG | AAG | AAG | TGC | CTG | GAG | CTG | TTC | 1114 |
| Leu | Lys | Val | Ile | Arg | Lys | Asn | Ile | Val | Lys | Lys | Cys | Leu | Glu | Leu | Phe | |
| | | | | 515 | | | | | 520 | | | | | 525 | | |
| GAA | GAG | ATA | GCG | GAG | AAC | AAG | GAG | GAC | TAC | AAG | CAG | TTC | TAC | GAG | CAG | 1162 |
| Glu | Glu | Ile | Ala | Glu | Asn | Lys | Glu | Asp | Tyr | Lys | Gln | Phe | Tyr | Glu | Gln | |
| | | | 530 | | | | | 535 | | | | | 540 | | | |
| TTC | GGC | AAG | AAC | ATC | AAG | CTG | GGC | ATC | CAC | GAG | GAC | ACG | GCG | AAC | CGC | 1210 |
| Phe | Gly | Lys | Asn | Ile | Lys | Leu | Gly | Ile | His | Glu | Asp | Thr | Ala | Asn | Arg | |
| | | 545 | | | | | 550 | | | | | 555 | | | | |
| AAG | AAG | CTG | ATG | GAG | TTG | CTG | CGC | TTC | TAC | AGC | ACC | GAG | TCG | GGG | GAG | 1258 |
| Lys | Lys | Leu | Met | Glu | Leu | Leu | Arg | Phe | Tyr | Ser | Thr | Glu | Ser | Gly | Glu | |
| | 560 | | | | | 565 | | | | | 570 | | | | | |
| GAG | ATG | ACG | ACA | CTG | AAG | GAC | TAC | GTG | ACG | CGC | ATG | AAG | CCG | GAG | CAG | 1306 |
| Glu | Met | Thr | Thr | Leu | Lys | Asp | Tyr | Val | Thr | Arg | Met | Lys | Pro | Glu | Gln | |
| 575 | | | | | 580 | | | | | 585 | | | | | 590 | |
| AAG | TCG | ATC | TAC | TAC | ATC | ACT | GGC | GAC | AGC | AAG | AAG | AAG | CTG | GAG | TCG | 1354 |
| Lys | Ser | Ile | Tyr | Tyr | Ile | Thr | Gly | Asp | Ser | Lys | Lys | Lys | Leu | Glu | Ser | |
| | | | | 595 | | | | | 600 | | | | | 605 | | |
| TCG | CCG | TTC | ATC | GAG | AAG | GCG | AGA | CGC | TGC | GGG | CTC | GAG | GTG | CTG | TTC | 1402 |
| Ser | Pro | Phe | Ile | Glu | Lys | Ala | Arg | Arg | Cys | Gly | Leu | Glu | Val | Leu | Phe | |
| | | | 610 | | | | | 615 | | | | | 620 | | | |
| ATG | ACG | GAG | CCG | ATC | GAC | GAG | TAC | GTG | ATG | CAG | CAG | GTG | AAG | GAC | TTC | 1450 |
| Met | Thr | Glu | Pro | Ile | Asp | Glu | Tyr | Val | Met | Gln | Gln | Val | Lys | Asp | Phe | |
| | | | 625 | | | | | 630 | | | | | 635 | | | |
| GAG | GAC | AAG | AAG | TTC | GCG | TGC | CTG | ACG | AAG | GAA | GGC | GTG | CAC | TTC | GAG | 1498 |
| Glu | Asp | Lys | Lys | Phe | Ala | Cys | Leu | Thr | Lys | Glu | Gly | Val | His | Phe | Glu | |
| | | 640 | | | | | 645 | | | | | 650 | | | | |

| | | | | | | | | | | | | | | | | |
|---|---|---|---|---|---|---|---|---|---|---|---|---|---|---|---|---|
| GAG | TCC | GAG | GAG | GAG | AAG | AAG | CAG | CGC | GAG | GAG | AAG | AAG | GCG | GCG | TGC | 1546 |
| Glu | Ser | Glu | Glu | Glu | Lys | Lys | Gln | Arg | Glu | Glu | Lys | Lys | Ala | Ala | Cys | |
| 655 | | | | 660 | | | | | 665 | | | | | | 670 | |
| GAG | AAG | CTG | TGC | AAG | ACG | ATG | AAG | GAG | GTG | CTG | GGC | GAC | AAG | GTG | GAG | 1594 |
| Glu | Lys | Leu | Cys | Lys | Thr | Met | Lys | Glu | Val | Leu | Gly | Asp | Lys | Val | Glu | |
| | | | | 675 | | | | 680 | | | | | 685 | | | |
| AAG | GTG | ACC | GTG | TCG | GAG | CGC | CTG | TTG | ACG | TCG | CCG | TGC | ATC | CTG | GTG | 1642 |
| Lys | Val | Thr | Val | Ser | Glu | Arg | Leu | Leu | Thr | Ser | Pro | Cys | Ile | Leu | Val | |
| | | | 690 | | | | 695 | | | | | 700 | | | | |
| ACG | TCG | GAG | TTT | GGG | TGG | TCG | GCG | CAC | ATG | GAA | CAG | ATC | ATG | CGC | AAC | 1690 |
| Thr | Ser | Glu | Phe | Gly | Trp | Ser | Ala | His | Met | Glu | Gln | Ile | Met | Arg | Asn | |
| | | 705 | | | | | 710 | | | | | 715 | | | | |
| CAG | GCG | CTG | CGC | GAC | TCC | AGC | ATG | GCG | CAG | TAC | ATG | GTG | TCC | AAG | AAG | 1738 |
| Gln | Ala | Leu | Arg | Asp | Ser | Ser | Met | Ala | Gln | Tyr | Met | Val | Ser | Lys | Lys | |
| | 720 | | | | | 725 | | | | | 730 | | | | | |
| ACG | ATG | GAG | GTG | AAC | CCC | GAC | CAC | CCC | ATC | ATC | AAG | GAG | CTG | CGC | CGC | 1786 |
| Thr | Met | Glu | Val | Asn | Pro | Asp | His | Pro | Ile | Ile | Lys | Glu | Leu | Arg | Arg | |
| 735 | | | | | 740 | | | | | 745 | | | | | 750 | |
| CGC | GTG | GAG | GCG | GAC | GAG | AAC | GAC | AAG | GCC | GTG | AAG | GAC | CTC | GTC | TTC | 1834 |
| Arg | Val | Glu | Ala | Asp | Glu | Asn | Asp | Lys | Ala | Val | Lys | Asp | Leu | Val | Phe | |
| | | | | 755 | | | | | 760 | | | | | 765 | | |
| CTG | CTC | TTC | GAC | ACG | TCG | CTG | CTC | ACG | TCC | GGC | TTC | CAG | CTG | GAT | GAC | 1882 |
| Leu | Leu | Phe | Asp | Thr | Ser | Leu | Leu | Thr | Ser | Gly | Phe | Gln | Leu | Asp | Asp | |
| | | | 770 | | | | | 775 | | | | | 780 | | | |
| CCC | ACC | GGC | TAC | GCC | GAG | CGC | ATC | AAC | CGC | ATG | ATC | AAG | CTC | GGC | CTG | 1930 |
| Pro | Thr | Gly | Tyr | Ala | Glu | Arg | Ile | Asn | Arg | Met | Ile | Lys | Leu | Gly | Leu | |
| | | 785 | | | | | 790 | | | | | 795 | | | | |
| TCG | CTC | GAC | GAG | GAG | GAG | GAG | GAG | GTC | GCC | GAG | GCG | CCG | CCG | GCC | GAG | 1978 |
| Ser | Leu | Asp | Glu | Glu | Glu | Glu | Glu | Val | Ala | Glu | Ala | Pro | Pro | Ala | Glu | |
| | 800 | | | | | 805 | | | | | 810 | | | | | |
| GCA | GCC | CCC | GCG | GAG | GTC | ACC | GCC | GGC | ACC | TCC | AGC | ATG | GAG | CAG | GTG | 2026 |
| Ala | Ala | Pro | Ala | Glu | Val | Thr | Ala | Gly | Thr | Ser | Ser | Met | Glu | Gln | Val | |
| 815 | | | | | 820 | | | | | 825 | | | | | 830 | |
| GAC | TGAGCCGGTA | A | | | | | | | | | | | | | | 2040 |
| Asp | | | | | | | | | | | | | | | | |

( 2 ) INFORMATION FOR SEQ ID NO:6:

( i ) SEQUENCE CHARACTERISTICS:
        ( A ) LENGTH: 656 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Ser | Leu | Thr | Asp | Pro | Ala | Val | Leu | Gly | Glu | Glu | Thr | His | Leu | Arg | Val |
| 1 | | | | 5 | | | | | 10 | | | | | 15 | |
| Arg | Val | Val | Pro | Asp | Lys | Ala | Asn | Lys | Thr | Leu | Thr | Val | Glu | Asp | Asn |
| | | | 20 | | | | | 25 | | | | | 30 | | |
| Gly | Ile | Gly | Met | Thr | Lys | Ala | Asp | Leu | Val | Asn | Asn | Leu | Gly | Thr | Ile |
| | | 35 | | | | | 40 | | | | | 45 | | | |
| Ala | Arg | Ser | Gly | Thr | Lys | Ala | Phe | Met | Glu | Ala | Leu | Glu | Ala | Gly | Gly |
| | 50 | | | | | 55 | | | | | 60 | | | | |
| Asp | Met | Ser | Met | Ile | Gly | Gln | Phe | Gly | Val | Gly | Phe | Tyr | Ser | Ala | Tyr |
| 65 | | | | 70 | | | | | 75 | | | | | 80 | |
| Leu | Val | Ala | Asp | Arg | Val | Thr | Val | Val | Ser | Lys | Asn | Asn | Ser | Asp | Glu |
| | | | 85 | | | | | 90 | | | | | 95 | | |
| Ala | Tyr | Trp | Glu | Ser | Ser | Ala | Gly | Gly | Thr | Phe | Thr | Ile | Thr | Ser | Val |
| | | | 100 | | | | | 105 | | | | | 110 | | |

| | | | | | | | | | | | | | |
|---|---|---|---|---|---|---|---|---|---|---|---|---|---|
| Gln | Glu | Ser | Asp | Met | Lys | Arg | Gly | Thr | Ser | Thr | Leu | His | Leu | Lys |
| | | 115 | | | | 120 | | | | 125 | | | |
| Glu | Asp | Gln | Gln | Glu | Tyr | Leu | Glu | Arg | Arg | Val | Lys | Glu | Leu | Ile |
| 130 | | | | | 135 | | | | 140 | | | | |
| Lys | Lys | His | Ser | Glu | Phe | Ile | Gly | Tyr | Asp | Ile | Glu | Leu | Met | Val | Glu |
| 145 | | | | | 150 | | | | | 155 | | | | | 160 |
| Lys | Thr | Ala | Glu | Lys | Glu | Val | Thr | Asp | Glu | Asp | Glu | Glu | Glu | Asp | Glu |
| | | | | 165 | | | | | 170 | | | | | 175 | |
| Ser | Lys | Lys | Lys | Ser | Cys | Gly | Asp | Glu | Gly | Glu | Pro | Lys | Val | Glu | Glu |
| | | | 180 | | | | | 185 | | | | | 190 | | |
| Val | Thr | Glu | Gly | Gly | Glu | Asp | Lys | Lys | Lys | Thr | Lys | Lys | Val | Lys |
| | | 195 | | | | 200 | | | | 205 | | | | |
| Glu | Val | Lys | Lys | Thr | Tyr | Glu | Val | Lys | Asn | Lys | His | Lys | Pro | Leu | Trp |
| 210 | | | | | 215 | | | | | 220 | | | | | |
| Thr | Arg | Asp | Thr | Lys | Asp | Val | Thr | Lys | Glu | Glu | Tyr | Ala | Ala | Phe | Tyr |
| 225 | | | | 230 | | | | | 235 | | | | | | 240 |
| Lys | Ala | Ile | Ser | Asn | Asp | Trp | Glu | Asp | Thr | Ala | Ala | Thr | Lys | His | Phe |
| | | | | 245 | | | | | 250 | | | | | 255 | |
| Ser | Val | Glu | Gly | Gln | Leu | Glu | Phe | Arg | Ala | Ile | Ala | Phe | Val | Pro | Lys |
| | | | 260 | | | | | 265 | | | | | 270 | | |
| Arg | Ala | Pro | Phe | Asp | Met | Phe | Glu | Pro | Asn | Lys | Lys | Arg | Asn | Asn | Ile |
| | | 275 | | | | | 280 | | | | | 285 | | | |
| Lys | Leu | Tyr | Val | Arg | Arg | Val | Phe | Ile | Met | Asp | Asn | Cys | Glu | Asp | Leu |
| | 290 | | | | | 295 | | | | | 300 | | | | |
| Cys | Pro | Asp | Trp | Leu | Gly | Phe | Val | Lys | Gly | Val | Val | Asp | Ser | Glu | Asp |
| 305 | | | | | 310 | | | | | 315 | | | | | 320 |
| Leu | Pro | Leu | Asn | Ile | Ser | Arg | Glu | Asn | Leu | Gln | Gln | Asn | Lys | Ile | Leu |
| | | | | 325 | | | | | 330 | | | | | 335 | |
| Lys | Val | Ile | Arg | Lys | Asn | Ile | Val | Lys | Lys | Cys | Leu | Glu | Leu | Phe | Glu |
| | | | 340 | | | | | 345 | | | | | 350 | | |
| Glu | Ile | Ala | Glu | Asn | Lys | Glu | Asp | Tyr | Lys | Gln | Phe | Tyr | Glu | Gln | Phe |
| | | 355 | | | | | 360 | | | | | 365 | | | |
| Gly | Lys | Asn | Ile | Lys | Leu | Gly | Ile | His | Glu | Asp | Thr | Ala | Asn | Arg | Lys |
| | 370 | | | | | 375 | | | | | 380 | | | | |
| Lys | Leu | Met | Glu | Leu | Leu | Arg | Phe | Tyr | Ser | Thr | Glu | Ser | Gly | Glu | Glu |
| 385 | | | | | 390 | | | | | 395 | | | | | 400 |
| Met | Thr | Thr | Leu | Lys | Asp | Tyr | Val | Thr | Arg | Met | Lys | Pro | Glu | Gln | Lys |
| | | | | 405 | | | | | 410 | | | | | 415 | |
| Ser | Ile | Tyr | Tyr | Ile | Thr | Gly | Asp | Ser | Lys | Lys | Lys | Leu | Glu | Ser | Ser |
| | | | 420 | | | | | 425 | | | | | 430 | | |
| Pro | Phe | Ile | Glu | Lys | Ala | Arg | Arg | Cys | Gly | Leu | Glu | Val | Leu | Phe | Met |
| | | 435 | | | | | 440 | | | | | 445 | | | |
| Thr | Glu | Pro | Ile | Asp | Glu | Tyr | Val | Met | Gln | Val | Lys | Asp | Phe | Glu |
| 450 | | | | | 455 | | | | | 460 | | | | |
| Asp | Lys | Lys | Phe | Ala | Cys | Leu | Thr | Lys | Glu | Gly | Val | His | Phe | Glu | Glu |
| 465 | | | | | 470 | | | | | 475 | | | | | 480 |
| Ser | Glu | Glu | Glu | Lys | Lys | Gln | Arg | Glu | Glu | Lys | Lys | Ala | Ala | Cys | Glu |
| | | | | 485 | | | | | 490 | | | | | 495 | |
| Lys | Leu | Cys | Lys | Thr | Met | Lys | Glu | Val | Leu | Gly | Asp | Lys | Val | Glu | Lys |
| | | | 500 | | | | | 505 | | | | | 510 | | |
| Val | Thr | Val | Ser | Glu | Arg | Leu | Leu | Thr | Ser | Pro | Cys | Ile | Leu | Val | Thr |
| | | 515 | | | | | 520 | | | | | 525 | | | |
| Ser | Glu | Phe | Gly | Trp | Ser | Ala | His | Met | Glu | Gln | Ile | Met | Arg | Asn | Gln |
| 530 | | | | | 535 | | | | | 540 | | | | | |

| Ala | Leu | Arg | Asp | Ser | Ser | Met | Ala | Gln | Tyr | Met | Val | Ser | Lys | Lys | Thr |
| 545 | | | | 550 | | | | | 555 | | | | | | 560 |

| Met | Glu | Val | Asn | Pro | Asp | His | Pro | Ile | Ile | Lys | Glu | Leu | Arg | Arg | Arg |
| | | | | 565 | | | | | 570 | | | | | 575 | |

| Val | Glu | Ala | Asp | Glu | Asn | Asp | Lys | Ala | Val | Lys | Asp | Leu | Val | Phe | Leu |
| | | | 580 | | | | | 585 | | | | | 590 | | |

| Leu | Phe | Asp | Thr | Ser | Leu | Leu | Thr | Ser | Gly | Phe | Gln | Leu | Asp | Asp | Pro |
| | | 595 | | | | | 600 | | | | | 605 | | | |

| Thr | Gly | Tyr | Ala | Glu | Arg | Ile | Asn | Arg | Met | Ile | Lys | Leu | Gly | Leu | Ser |
| | 610 | | | | | 615 | | | | | 620 | | | | |

| Leu | Asp | Glu | Glu | Glu | Glu | Glu | Val | Ala | Glu | Ala | Pro | Pro | Ala | Glu | Ala |
| 625 | | | | | 630 | | | | | 635 | | | | | 640 |

| Ala | Pro | Ala | Glu | Val | Thr | Ala | Gly | Thr | Ser | Ser | Met | Glu | Gln | Val | Asp |
| | | | | 645 | | | | | 650 | | | | | 655 | |

(2) INFORMATION FOR SEQ ID NO:7:

(i) SEQUENCE CHARACTERISTICS:
  (A) LENGTH: 1771 base pairs
  (B) TYPE: nucleic acid
  (C) STRANDEDNESS: single
  (D) TOPOLOGY: linear (ix) FEATURE:
  (A) NAME/KEY: CDS
  (B) LOCATION: 1..1698

(xi) SEQUENCE DESCRIPTION: SEQ ID NO:7:

| CAG | GCC | CGC | GTC | CAG | GCC | CTC | GAG | GAG | GCA | GCG | CGT | CTC | CGC | GCG | GAG | 48 |
| Gln | Ala | Arg | Val | Gln | Ala | Leu | Glu | Glu | Ala | Ala | Arg | Leu | Arg | Ala | Glu | |
| 1 | | | | 5 | | | | | 10 | | | | | 15 | | |

| CTG | GAG | GCG | GCC | GAG | GAG | GCG | GCC | CGC | CTG | GAT | GTC | ATG | CAT | GCG | GCC | 96 |
| Leu | Glu | Ala | Ala | Glu | Glu | Ala | Ala | Arg | Leu | Asp | Val | Met | His | Ala | Ala | |
| | | | 20 | | | | | 25 | | | | | 30 | | | |

| GAG | CAG | GCC | CGT | GTC | CAG | GCC | CTC | GAG | GAG | GCA | GCG | CGT | CTC | CGC | GCG | 144 |
| Glu | Gln | Ala | Arg | Val | Gln | Ala | Leu | Glu | Glu | Ala | Ala | Arg | Leu | Arg | Ala | |
| | | 35 | | | | | 40 | | | | | 45 | | | | |

| GAG | CTG | GAG | GAG | GCC | GAG | GAG | GCG | GCC | CGC | CTG | GAT | GTC | ATG | CAT | GCG | 192 |
| Glu | Leu | Glu | Glu | Ala | Glu | Glu | Ala | Ala | Arg | Leu | Asp | Val | Met | His | Ala | |
| | 50 | | | | | 55 | | | | | 60 | | | | | |

| GCC | GAG | CAG | GCC | CGC | GTC | CAG | GCC | CTC | GAG | GAG | GCA | GCG | CGT | CTC | CGC | 240 |
| Ala | Glu | Gln | Ala | Arg | Val | Gln | Ala | Leu | Glu | Glu | Ala | Ala | Arg | Leu | Arg | |
| 65 | | | | | 70 | | | | | 75 | | | | | 80 | |

| GCG | GAG | CTG | GAG | GCT | GCC | GAG | GAG | GCG | GCG | CGC | CTG | GAG | GCC | ATG | CAC | 288 |
| Ala | Glu | Leu | Glu | Ala | Ala | Glu | Glu | Ala | Ala | Arg | Leu | Glu | Ala | Met | His | |
| | | | | 85 | | | | | 90 | | | | | 95 | | |

| GAG | GCC | GAG | CAG | GCC | CGC | TCC | CAG | GCC | CTC | GAG | GAG | GCA | GCG | CGT | CTC | 336 |
| Glu | Ala | Glu | Gln | Ala | Arg | Ser | Gln | Ala | Leu | Glu | Glu | Ala | Ala | Arg | Leu | |
| | | | 100 | | | | | 105 | | | | | 110 | | | |

| CGC | GCG | GAG | CTG | GAG | GAA | GCC | GAG | GAG | GCG | GCC | CGC | CTG | GAT | GTC | ATG | 384 |
| Arg | Ala | Glu | Leu | Glu | Glu | Ala | Glu | Glu | Ala | Ala | Arg | Leu | Asp | Val | Met | |
| | | | 115 | | | | | 120 | | | | | 125 | | | |

| CAT | GCG | GCC | GAG | CAG | GCC | CGC | GTC | CAG | GCC | CTC | GAG | GAG | GCA | GCG | CGT | 432 |
| His | Ala | Ala | Glu | Gln | Ala | Arg | Val | Gln | Ala | Leu | Glu | Glu | Ala | Ala | Arg | |
| | | 130 | | | | | 135 | | | | | 140 | | | | |

| CTC | CGC | GCG | GAG | CTG | GAG | GAG | GCC | GAG | GAG | GCG | GCC | CGC | CTG | GAG | GCC | 480 |
| Leu | Arg | Ala | Glu | Leu | Glu | Glu | Ala | Glu | Glu | Ala | Ala | Arg | Leu | Glu | Ala | |
| 145 | | | | | 150 | | | | | 155 | | | | | 160 | |

| ATG | CAC | GAG | GCC | GAG | CAG | GCC | CGC | TCC | CAG | GCC | CTC | GAG | GAG | GCA | GCG | 528 |
| Met | His | Glu | Ala | Glu | Gln | Ala | Arg | Ser | Gln | Ala | Leu | Glu | Glu | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| CGT | CTC | CGC | GCG | GAG | CTG | GAG | GCG | GCC | GAG | GAG | GCG | GCC | CGC | CTG | GAT | 576 |
| Arg | Leu | Arg | Ala | Glu | Leu | Glu | Ala | Ala | Glu | Glu | Ala | Ala | Arg | Leu | Asp | |
| | | 180 | | | | | 185 | | | | | | 190 | | | |
| GTC | ATG | CAC | GAG | GCC | GAG | CAG | GCC | CGT | GTC | CAG | GCC | CTC | GAG | GAG | GCG | 624 |
| Val | Met | His | Glu | Ala | Glu | Gln | Ala | Arg | Val | Gln | Ala | Leu | Glu | Glu | Ala | |
| | | 195 | | | | | 200 | | | | | 205 | | | | |
| GCG | CGC | CTG | GAT | GTC | ATG | CAC | GAG | GCC | GAG | CAG | GCC | CGC | GTC | CAG | GCC | 672 |
| Ala | Arg | Leu | Asp | Val | Met | His | Glu | Ala | Glu | Gln | Ala | Arg | Val | Gln | Ala | |
| 210 | | | | | 215 | | | | | 220 | | | | | | |
| CTC | GAG | GAG | GCA | GCG | CGT | CTC | CGC | GCG | GAG | CTG | GAG | GCG | GCC | GAG | GAG | 720 |
| Leu | Glu | Glu | Ala | Ala | Arg | Leu | Arg | Ala | Glu | Leu | Glu | Ala | Ala | Glu | Glu | |
| 225 | | | | | 230 | | | | | 235 | | | | | 240 | |
| GCG | GCC | CGC | CTG | GAT | GTC | ATG | CAC | GAG | GCC | GAG | CAG | GCC | CGC | GTC | CAG | 768 |
| Ala | Ala | Arg | Leu | Asp | Val | Met | His | Glu | Ala | Glu | Gln | Ala | Arg | Val | Gln | |
| | | | | 245 | | | | | 250 | | | | | 255 | | |
| GCC | CTC | GAG | GAG | GCA | GCG | CGT | CTC | CGC | GCG | GAG | CTG | GAG | GCG | GCC | GAG | 816 |
| Ala | Leu | Glu | Glu | Ala | Ala | Arg | Leu | Arg | Ala | Glu | Leu | Glu | Ala | Ala | Glu | |
| | | | 260 | | | | | 265 | | | | | 270 | | | |
| GAG | GCG | GCC | CGC | CTG | GAT | GTC | ATG | CAC | GAG | GGC | GAG | CAG | GCC | CGT | GTC | 864 |
| Glu | Ala | Ala | Arg | Leu | Asp | Val | Met | His | Glu | Gly | Glu | Gln | Ala | Arg | Val | |
| | | 275 | | | | | 280 | | | | | 285 | | | | |
| CAG | GCC | CTC | GAG | GAG | GCG | GCC | CGC | CTG | GAG | GCC | ATG | CAC | GAG | GCC | GAG | 912 |
| Gln | Ala | Leu | Glu | Glu | Ala | Ala | Arg | Leu | Glu | Ala | Met | His | Glu | Ala | Glu | |
| | 290 | | | | | 295 | | | | | 300 | | | | | |
| CAG | GCC | CGC | TCC | CAG | GCC | CTC | GAG | GAG | GCA | GCG | CGT | CTC | TGC | GCG | GAG | 960 |
| Gln | Ala | Arg | Ser | Gln | Ala | Leu | Glu | Glu | Ala | Ala | Arg | Leu | Cys | Ala | Glu | |
| 305 | | | | | 310 | | | | | 315 | | | | | 320 | |
| CTG | GAG | GCT | GAG | GAG | GAG | GAA | AAA | GAT | GAG | CGG | CCG | GCG | ACG | TCG | AGC | 1008 |
| Leu | Glu | Ala | Glu | Glu | Glu | Glu | Lys | Asp | Glu | Arg | Pro | Ala | Thr | Ser | Ser | |
| | | | | 325 | | | | | 330 | | | | | 335 | | |
| TAC | AGC | GAG | GAG | TGC | AAA | GGG | CGA | CTG | CTA | TCG | AGG | GCG | CGG | CCG | GAT | 1056 |
| Tyr | Ser | Glu | Glu | Cys | Lys | Gly | Arg | Leu | Leu | Ser | Arg | Ala | Arg | Pro | Asp | |
| | | | 340 | | | | | 345 | | | | | 350 | | | |
| CCG | CGG | AGG | CCG | CTG | CCG | CGG | CCG | TTC | ATT | GGG | ATG | TCA | CTG | TTG | GAG | 1104 |
| Pro | Arg | Arg | Pro | Leu | Pro | Arg | Pro | Phe | Ile | Gly | Met | Ser | Leu | Leu | Glu | |
| | | 355 | | | | | 360 | | | | | 365 | | | | |
| GAT | GTG | GAG | AAG | AGT | ATT | CTC | ATT | GTG | GAC | GGG | CTC | TAC | AGG | GAT | GGG | 1152 |
| Asp | Val | Glu | Lys | Ser | Ile | Leu | Ile | Val | Asp | Gly | Leu | Tyr | Arg | Asp | Gly | |
| | 370 | | | | | 375 | | | | | 380 | | | | | |
| CCG | GCG | TAC | CAG | ACG | GGC | ATC | CGC | CTC | GGG | GAT | GTC | CTC | TTG | CGT | ATC | 1200 |
| Pro | Ala | Tyr | Gln | Thr | Gly | Ile | Arg | Leu | Gly | Asp | Val | Leu | Leu | Arg | Ile | |
| 385 | | | | | 390 | | | | | 395 | | | | | 400 | |
| GCG | GGG | GTT | TAC | GTG | GAT | TCA | ATA | GCG | AAG | GCG | AGG | CAG | GTG | GTC | GAT | 1248 |
| Ala | Gly | Val | Tyr | Val | Asp | Ser | Ile | Ala | Lys | Ala | Arg | Gln | Val | Val | Asp | |
| | | | | 405 | | | | | 410 | | | | | 415 | | |
| GCG | CGT | TGC | CGC | TGC | GGC | TGC | GTC | GTT | CCC | GTG | ACG | CTG | GCG | ACG | AAG | 1296 |
| Ala | Arg | Cys | Arg | Cys | Gly | Cys | Val | Val | Pro | Val | Thr | Leu | Ala | Thr | Lys | |
| | | | 420 | | | | | 425 | | | | | 430 | | | |
| ATG | AAC | CAG | CAG | TAC | AGC | GTG | GCT | CTG | TAT | ATC | ATG | ACG | GTG | GAT | CCG | 1344 |
| Met | Asn | Gln | Gln | Tyr | Ser | Val | Ala | Leu | Tyr | Ile | Met | Thr | Val | Asp | Pro | |
| | | 435 | | | | | 440 | | | | | 445 | | | | |
| CAG | CAC | AAC | GAC | AAG | CCC | TTT | TTT | TTT | GAT | GTG | CAC | ATC | CAC | CAC | CGC | 1392 |
| Gln | His | Asn | Asp | Lys | Pro | Phe | Phe | Phe | Asp | Val | His | Ile | His | His | Arg | |
| | 450 | | | | | 455 | | | | | 460 | | | | | |
| ATC | GAG | AGC | TCG | CAC | ATG | GGG | AAG | AAG | GCG | CAG | TGG | ATG | GAA | GTT | CTT | 1440 |
| Ile | Glu | Ser | Ser | His | Met | Gly | Lys | Lys | Ala | Gln | Trp | Met | Glu | Val | Leu | |
| 465 | | | | | 470 | | | | | 475 | | | | | 480 | |
| GAG | AGC | CCA | TCC | GTA | TCT | TCG | GCT | GCC | ACC | ACC | CCT | CTC | GTG | CCG | CTC | 1488 |
| Glu | Ser | Pro | Ser | Val | Ser | Ser | Ala | Ala | Thr | Thr | Pro | Leu | Val | Pro | Leu | |
| | | | | 485 | | | | | 490 | | | | | 495 | | |

```
TTG  CGT  GAG  CCG  ACG  CCG  CGT  AGG  GGC  TCA  GAG  CTG  CAG  TCA  AGT  GCT      1536
Leu  Arg  Glu  Pro  Thr  Pro  Arg  Arg  Gly  Ser  Glu  Leu  Gln  Ser  Ser  Ala
               500                      505                      510

CGT  TCC  GCC  TTC  GTT  GCC  ACG  TCT  TAC  TTC  TCG  AGC  GCG  CGC  AGG  TCG      1584
Arg  Ser  Ala  Phe  Val  Ala  Thr  Ser  Tyr  Phe  Ser  Ser  Ala  Arg  Arg  Ser
          515                      520                      525

GTC  AGC  TCA  GAA  AGT  GAG  CGA  CCG  CGC  GGG  TCC  TCT  AGC  GTG  GCT  ATG      1632
Val  Ser  Ser  Glu  Ser  Glu  Arg  Pro  Arg  Gly  Ser  Ser  Ser  Val  Ala  Met
     530                      535                      540

GCG  GAG  GAG  GCG  ATC  GCG  CTG  GCG  CCG  CAA  GGG  TAT  ACC  CCA  CCC  AAC      1680
Ala  Glu  Glu  Ala  Ile  Ala  Leu  Ala  Pro  Gln  Gly  Tyr  Thr  Pro  Pro  Asn
545                      550                      555                      560

CAA  GTG  CGC  GGC  CGT  AGT  TGACGTCTCT  GTGTGAGTGT  GTGTCGCTCC                    1728
Gln  Val  Arg  Gly  Arg  Ser
                    565

GTCTCCTTCC  TTTTCGTCA  TGTGTTTTAT  TCATTTCTTT  TTC                                  1771
```

( 2 ) INFORMATION FOR SEQ ID NO:8:

( i ) SEQUENCE CHARACTERISTICS:
        ( A ) LENGTH: 566 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Gln  Ala  Arg  Val  Gln  Ala  Leu  Glu  Glu  Ala  Ala  Arg  Leu  Arg  Ala  Glu
  1                 5                    10                       15

Leu  Glu  Ala  Ala  Glu  Glu  Ala  Ala  Arg  Leu  Asp  Val  Met  His  Ala  Ala
               20                      25                       30

Glu  Gln  Ala  Arg  Val  Gln  Ala  Leu  Glu  Glu  Ala  Ala  Arg  Leu  Arg  Ala
               35                      40                       45

Glu  Leu  Glu  Glu  Ala  Glu  Glu  Ala  Ala  Arg  Leu  Asp  Val  Met  His  Ala
          50                      55                       60

Ala  Glu  Gln  Ala  Arg  Val  Gln  Ala  Leu  Glu  Glu  Ala  Ala  Arg  Leu  Arg
 65                      70                      75                       80

Ala  Glu  Leu  Glu  Ala  Ala  Glu  Glu  Ala  Ala  Arg  Leu  Glu  Ala  Met  His
                    85                      90                       95

Glu  Ala  Glu  Gln  Ala  Arg  Ser  Gln  Ala  Leu  Glu  Glu  Ala  Ala  Arg  Leu
                   100                     105                      110

Arg  Ala  Glu  Leu  Glu  Glu  Ala  Glu  Ala  Ala  Arg  Leu  Asp  Val  Met
          115                     120                      125

His  Ala  Ala  Glu  Gln  Ala  Arg  Val  Gln  Ala  Leu  Glu  Glu  Ala  Ala  Arg
     130                     135                      140

Leu  Arg  Ala  Glu  Leu  Glu  Glu  Ala  Glu  Glu  Ala  Ala  Arg  Leu  Glu  Ala
145                      150                     155                      160

Met  His  Glu  Ala  Glu  Gln  Ala  Arg  Ser  Gln  Ala  Leu  Glu  Glu  Ala  Ala
                    165                     170                      175

Arg  Leu  Arg  Ala  Glu  Leu  Glu  Ala  Ala  Glu  Glu  Ala  Ala  Arg  Leu  Asp
               180                     185                      190

Val  Met  His  Glu  Ala  Glu  Gln  Ala  Arg  Val  Gln  Ala  Leu  Glu  Glu  Ala
          195                     200                      205

Ala  Arg  Leu  Asp  Val  Met  His  Glu  Ala  Glu  Gln  Ala  Arg  Val  Gln  Ala
     210                     215                      220

Leu  Glu  Glu  Ala  Ala  Arg  Leu  Arg  Ala  Glu  Leu  Glu  Ala  Ala  Glu  Glu
225                      230                     235                      240
```

Ala Ala Arg Leu Asp Val Met His Glu Ala Glu Gln Ala Arg Val Gln
            245                 250                 255

Ala Leu Glu Glu Ala Ala Arg Leu Arg Ala Glu Leu Glu Ala Ala Glu
        260                 265                 270

Glu Ala Ala Arg Leu Asp Val Met His Glu Gly Glu Gln Ala Arg Val
        275                 280                 285

Gln Ala Leu Glu Glu Ala Ala Arg Leu Glu Ala Met His Glu Ala Glu
        290                 295                 300

Gln Ala Arg Ser Gln Ala Leu Glu Glu Ala Ala Arg Leu Cys Ala Glu
305                 310                 315                 320

Leu Glu Ala Glu Glu Glu Glu Lys Asp Glu Arg Pro Ala Thr Ser Ser
                325                 330                 335

Tyr Ser Glu Glu Cys Lys Gly Arg Leu Leu Ser Arg Ala Arg Pro Asp
        340                 345                 350

Pro Arg Arg Pro Leu Pro Arg Pro Phe Ile Gly Met Ser Leu Leu Glu
        355                 360                 365

Asp Val Glu Lys Ser Ile Leu Ile Val Asp Gly Leu Tyr Arg Asp Gly
        370                 375                 380

Pro Ala Tyr Gln Thr Gly Ile Arg Leu Gly Asp Val Leu Leu Arg Ile
385                 390                 395                 400

Ala Gly Val Tyr Val Asp Ser Ile Ala Lys Ala Arg Gln Val Val Asp
                405                 410                 415

Ala Arg Cys Arg Cys Gly Cys Val Val Pro Val Thr Leu Ala Thr Lys
        420                 425                 430

Met Asn Gln Gln Tyr Ser Val Ala Leu Tyr Ile Met Thr Val Asp Pro
        435                 440                 445

Gln His Asn Asp Lys Pro Phe Phe Phe Asp Val His Ile His His Arg
    450                 455                 460

Ile Glu Ser Ser His Met Gly Lys Lys Ala Gln Trp Met Glu Val Leu
465                 470                 475                 480

Glu Ser Pro Ser Val Ser Ser Ala Ala Thr Thr Pro Leu Val Pro Leu
                485                 490                 495

Leu Arg Glu Pro Thr Pro Arg Arg Gly Ser Glu Leu Gln Ser Ser Ala
            500                 505                 510

Arg Ser Ala Phe Val Ala Thr Ser Tyr Phe Ser Ser Ala Arg Arg Ser
        515                 520                 525

Val Ser Ser Glu Ser Glu Arg Pro Arg Gly Ser Ser Ser Val Ala Met
    530                 535                 540

Ala Glu Glu Ala Ile Ala Leu Ala Pro Gln Gly Tyr Thr Pro Pro Asn
545                 550                 555                 560

Gln Val Arg Gly Arg Ser
            565

( 2 ) INFORMATION FOR SEQ ID NO:9:

( i ) SEQUENCE CHARACTERISTICS:
        ( A ) LENGTH: 1618 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..1323

( x i ) SEQUENCE DESCRIPTION: SEQ ID NO:9:

| | | | | | | | | | | | | | | |
|---|---|---|---|---|---|---|---|---|---|---|---|---|---|---|
| CCACTCTCTC | GGTCGTCTGT | CTCCCACGCG | CGCACGCAGT | TGATTTCCGC | CTTCTTAAAC | | | | | | | | | 60 |
| GCTCTCTTTT | TTTTTATTTT | TCACCTGACC | AACCGCACCA | CGTCGGCCTC | CATC | ATG Met 1 | | | | | | | | 117 |
| TCG Ser | CAG Gln | CAA Gln | GAC Asp 5 | CGA Arg | GTT Val | GCC Ala | CCA Pro | CAG Gln 10 | GAC Asp | CAG Gln | GAC Asp | TCG Ser 15 | TTC Phe | CTC Leu | GAC Asp | 165 |
| GAC Asp | CAG Gln | CCC Pro 20 | GGC Gly | GTC Val | CGC Arg | CCG Pro | ATC Ile 25 | CCG Pro | TCC Ser | TTC Phe | GAT Asp | GAC Asp 30 | ATG Met | CCG Pro | TTG Leu | 213 |
| CAC His | CAG Gln | AAC Asn 35 | CTT Leu | CTG Leu | CGC Arg | GGC Gly | ATC Ile 40 | TAC Tyr | TCG Ser | TAC Tyr | GGC Gly | TTC Phe 45 | GAG Glu | AAA Lys | CCG Pro | 261 |
| TCC Ser 50 | AGC Ser | ATC Ile | CAG Gln | CAG Gln | CGC Arg 55 | GCC Ala | ATC Ile | GCC Ala | CCC Pro | TTC Phe 60 | ACG Thr | CGC Arg | GGC Gly | GGC Gly | GAC Asp 65 | 309 |
| ATC Ile | ATC Ile | GCG Ala | CAG Gln | GCG Ala 70 | CAG Gln | TCC Ser | GGT Gly | ACC Thr | GGC Gly 75 | AAG Lys | ACG Thr | GGC Gly | GCC Ala | TTC Phe 80 | TCC Ser | 357 |
| ATC Ile | GGC Gly | CTG Leu | CTG Leu 85 | CAG Gln | CGC Arg | CTG Leu | GAC Asp | TTC Phe 90 | CGC Arg | CAC His | AAC Asn | CTG Leu | ATC Ile 95 | CAG Gln | GGC Gly | 405 |
| CTC Leu | GTG Val | CTC Leu 100 | TCC Ser | CCG Pro | ACC Thr | CGC Arg | GAG Glu 105 | CTG Leu | GCC Ala | CTG Leu | CAG Gln | ACG Thr 110 | GCG Ala | GAG Glu | GTG Val | 453 |
| ATC Ile | AGC Ser 115 | CGC Arg | ATC Ile | GGC Gly | GAG Glu 120 | TTC Phe | CTG Leu | TCG Ser | AAC Asn | AGC Ser 125 | GCG Ala | AAG Lys | TTC Phe | TGT Cys | GAG Glu | 501 |
| ACC Thr 130 | TTT Phe | GTG Val | GGT Gly | GGC Gly | ACG Thr 135 | CGC Arg | GTG Val | CAG Gln | GAT Asp | GAC Asp 140 | CTG Leu | CGC Arg | AAG Lys | CTG Leu | CAG Gln 145 | 549 |
| GCT Ala | GGC Gly | GTC Val | GTC Val | GTC Val 150 | GCC Ala | GTG Val | GGG Gly | ACG Thr | CCG Pro 155 | GGC Gly | CGC Arg | GTG Val | TCC Ser | GAC Asp 160 | GTG Val | 597 |
| ATC Ile | AAG Lys | CGC Arg | GGC Gly 165 | GCG Ala | CTG Leu | CGC Arg | ACC Thr | GAG Glu 170 | TCC Ser | CTG Leu | CGC Arg | GTG Val | CTG Leu 175 | GTG Val | CTC Leu | 645 |
| GAC Asp | GAG Glu | GCT Ala | GAT Asp | GAG Glu 180 | ATG Met | CTG Leu | TCT Ser | CAG Gln | GGC Gly 185 | TTC Phe | GCG Ala | GAT Asp | CAG Gln | ATT Ile 190 | TAC Tyr | 693 |
| GAG Glu | ATC Ile 195 | TTC Phe | CGC Arg | TTC Phe | CTG Leu | CCG Pro 200 | AAG Lys | GAC Asp | ATC Ile | CAG Gln | GTC Val 205 | GCG Ala | CTC Leu | TTC Phe | TCC Ser | 741 |
| GCC Ala 210 | ACG Thr | ATG Met | CCG Pro | GAG Glu | GAG Glu 215 | GTG Val | CTG Leu | GAG Glu | CTG Leu | ACA Thr 220 | AAG Lys | AAG Lys | TTC Phe | ATG Met | CGC Arg 225 | 789 |
| GAC Asp | CCC Pro | GTA Val | CGC Arg | ATT Ile 230 | CTC Leu | GTG Val | AAG Lys | CGC Arg | GAG Glu 235 | AGC Ser | CTG Leu | ACG Thr | CTG Leu | GAG Glu 240 | GGC Gly | 837 |
| ATC Ile | AAG Lys | CAG Gln | TTC Phe | TTC Phe 245 | ATC Ile | GCC Ala | GTC Val | GAG Glu | GAG Glu 250 | GAG Glu | CAC His | AAG Lys | CTG Leu | GAC Asp 255 | ACG Thr | 885 |
| CTG Leu | ATG Met | GAC Asp 260 | CTG Leu | TAC Tyr | GAG Glu | ACC Thr | GTG Val 265 | TCC Ser | ATC Ile | GCG Ala | CAG Gln | TCC Ser 270 | GTC Val | ATC Ile | TTC Phe | 933 |
| GCC Ala | AAC Asn | ACC Thr 275 | CGC Arg | CGC Arg | AAG Lys | GTC Val | GAC Asp 280 | TGG Trp | ATC Ile | GCC Ala | GAG Glu | AAG Lys 285 | CTG Leu | AAT Asn | CAG Gln | 981 |
| AGC Ser | AAC Asn | CAC His | ACC Thr | GTC Val | AGC Ser | AGC Ser | ATG Met | CAC His | GCC Ala | GAG Glu | ATG Met | CCC Pro | AAG Lys | AGC Ser | GAC Asp | 1029 |

-continued

```
                      290                       295                       300                            305
CGC  GAG  CGC  GTC  ATG  AAC  ACC  TTC  CGC  AGC  GGC  AGC  TCC  CGC  GTG  CTC    1077
Arg  Glu  Arg  Val  Met  Asn  Thr  Phe  Arg  Ser  Gly  Ser  Ser  Arg  Val  Leu
                    310                       315                            320

GTA  ACG  ACC  GAC  CTC  GTG  GCC  CGC  GGC  ATC  GAC  GTG  CAC  CAC  GTG  AAC    1125
Val  Thr  Thr  Asp  Leu  Val  Ala  Arg  Gly  Ile  Asp  Val  His  His  Val  Asn
               325                       330                       335

ATC  GTC  ATC  AAC  TTC  GAC  CTG  CCG  ACG  AAC  AAG  GAG  AAC  TAC  CTG  CAC    1173
Ile  Val  Ile  Asn  Phe  Asp  Leu  Pro  Thr  Asn  Lys  Glu  Asn  Tyr  Leu  His
               340                       345                       350

CGC  ATT  GGC  CGC  GGC  GGC  CGC  TAC  GGC  GTA  AAG  GGT  GTT  GCC  ATC  AAC    1221
Arg  Ile  Gly  Arg  Gly  Gly  Arg  Tyr  Gly  Val  Lys  Gly  Val  Ala  Ile  Asn
          355                       360                       365

TTC  GTG  ACG  GAG  AAA  GAC  GTG  GAG  CTG  CTG  CAC  GAG  ATC  GAG  GGG  CAC    1269
Phe  Val  Thr  Glu  Lys  Asp  Val  Glu  Leu  Leu  His  Glu  Ile  Glu  Gly  His
370                      375                       380                       385

TAC  CAC  ACG  CAG  ATC  GAT  GAG  CTC  CCG  GTG  GAC  TTT  GCC  GCC  TAC  CTC    1317
Tyr  His  Thr  Gln  Ile  Asp  Glu  Leu  Pro  Val  Asp  Phe  Ala  Ala  Tyr  Leu
                    390                       395                            400

GGC  GAG  TGA  GCGGGCCCCT  GCCCCCTTC  CCTGCCCCC  TCTCGCGACG                        1366
Gly  Glu

AGAGAACGCA  CATCGTAACA  CAGCCACGCG  AACGATAGTA  AGGGCGTGCG  GCGGCGTTCC            1426

CCTCCTCCTG  CCAGCGGCCC  CCCTCCGCAG  CGCTTCTCTT  TTGAGAGGGG  GGCAGGGGGA            1486

GGCGCTGCGC  CTGGCTGGAT  GTGTGCTTGA  GCTTGCATTC  CGTCAAGCAA  GTGCTTTGTT            1546

TTAATTATGC  GCGCCGTTTT  GTTGCTCGTC  CCTTTCGTTG  GTGTTTTTTC  GGCCGAAACG            1606

GCGTTTAAAG  CA                                                                    1618
```

( 2 ) INFORMATION FOR SEQ ID NO:10:

( i ) SEQUENCE CHARACTERISTICS:
     ( A ) LENGTH: 403 amino acids
     ( B ) TYPE: amino acid
     ( D ) TOPOLOGY: linear ( i i ) MOLECULE TYPE: protein ( x i ) SEQUENCE DESCRIPTION: SEQ ID NO:10:

```
Met  Ser  Gln  Gln  Asp  Arg  Val  Ala  Pro  Gln  Asp  Gln  Asp  Ser  Phe  Leu
  1                 5                      10                           15

Asp  Asp  Gln  Pro  Gly  Val  Arg  Pro  Ile  Pro  Ser  Phe  Asp  Asp  Met  Pro
                    20                          25                      30

Leu  His  Gln  Asn  Leu  Leu  Arg  Gly  Ile  Tyr  Ser  Tyr  Gly  Phe  Glu  Lys
               35                         40                 45

Pro  Ser  Ser  Ile  Gln  Gln  Arg  Ala  Ile  Ala  Pro  Phe  Thr  Arg  Gly  Gly
          50                        55                      60

Asp  Ile  Ile  Ala  Gln  Ala  Gln  Ser  Gly  Thr  Gly  Lys  Thr  Gly  Ala  Phe
 65                      70                      75                           80

Ser  Ile  Gly  Leu  Leu  Gln  Arg  Leu  Asp  Phe  Arg  His  Asn  Leu  Ile  Gln
                    85                      90                           95

Gly  Leu  Val  Leu  Ser  Pro  Thr  Arg  Glu  Ala  Leu  Gln  Thr  Ala  Glu
                    100                     105                     110

Val  Ile  Ser  Arg  Ile  Gly  Glu  Phe  Leu  Ser  Asn  Ser  Ala  Lys  Phe  Cys
               115                     120                     125

Glu  Thr  Phe  Val  Gly  Gly  Thr  Arg  Val  Gln  Asp  Asp  Leu  Arg  Lys  Leu
          130                     135                     140

Gln  Ala  Gly  Val  Val  Val  Ala  Val  Gly  Thr  Pro  Gly  Arg  Val  Ser  Asp
145                     150                     155                          160
```

```
Val  Ile  Lys  Arg  Gly  Ala  Leu  Arg  Thr  Glu  Ser  Leu  Arg  Val  Leu  Val
               165                      170                     175

Leu  Asp  Glu  Ala  Asp  Glu  Met  Leu  Ser  Gln  Gly  Phe  Ala  Asp  Gln  Ile
               180                      185                     190

Tyr  Glu  Ile  Phe  Arg  Phe  Leu  Pro  Lys  Asp  Ile  Gln  Val  Ala  Leu  Phe
               195                      200                     205

Ser  Ala  Thr  Met  Pro  Glu  Val  Leu  Glu  Leu  Thr  Lys  Lys  Phe  Met
     210                      215                     220

Arg  Asp  Pro  Val  Arg  Ile  Leu  Val  Lys  Arg  Glu  Ser  Leu  Thr  Leu  Glu
225                      230                     235                          240

Gly  Ile  Lys  Gln  Phe  Phe  Ile  Ala  Val  Glu  Glu  His  Lys  Leu  Asp
               245                      250                     255

Thr  Leu  Met  Asp  Leu  Tyr  Glu  Thr  Val  Ser  Ile  Ala  Gln  Ser  Val  Ile
               260                      265                     270

Phe  Ala  Asn  Thr  Arg  Arg  Lys  Val  Asp  Trp  Ile  Ala  Glu  Lys  Leu  Asn
               275                      280                     285

Gln  Ser  Asn  His  Thr  Val  Ser  Ser  Met  His  Ala  Glu  Met  Pro  Lys  Ser
               290                      295                     300

Asp  Arg  Glu  Arg  Val  Met  Asn  Thr  Phe  Arg  Ser  Gly  Ser  Ser  Arg  Val
305                      310                     315                          320

Leu  Val  Thr  Thr  Asp  Leu  Val  Ala  Arg  Gly  Ile  Asp  Val  His  His  Val
               325                      330                     335

Asn  Ile  Val  Ile  Asn  Phe  Asp  Leu  Pro  Thr  Asn  Lys  Glu  Asn  Tyr  Leu
               340                      345                     350

His  Arg  Ile  Gly  Arg  Gly  Gly  Arg  Tyr  Gly  Val  Lys  Gly  Val  Ala  Ile
               355                      360                     365

Asn  Phe  Val  Thr  Glu  Lys  Asp  Val  Glu  Leu  Leu  His  Glu  Ile  Glu  Gly
     370                      375                     380

His  Tyr  His  Thr  Gln  Ile  Asp  Glu  Leu  Pro  Val  Asp  Phe  Ala  Ala  Tyr
385                      390                     395                          400

Leu  Gly  Glu
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i x ) FEATURE:
        ( A ) NAME/KEY: Modified-site
        ( B ) LOCATION: 6
        ( D ) OTHER INFORMATION: /note= "Where Xaa is either a Leu
            or Lys Residue"

( x i ) SEQUENCE DESCRIPTION: SEQ ID NO:11:

```
Xaa  Gln  Xaa  Pro  Gln  Xaa  Val  Phe  Asp  Glu  Xaa  Xaa
1                   5                        10
```

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i x ) FEATURE:
        ( A ) NAME/KEY: -
        ( B ) LOCATION: 11

(D) OTHER INFORMATION: /note= "Where n is inosine"

(ix) FEATURE:
    (A) NAME/KEY: -
    (B) LOCATION: 17
    (D) OTHER INFORMATION: /note= "Where n is inosine"

(ix) FEATURE:
    (A) NAME/KEY: -
    (B) LOCATION: 20
    (D) OTHER INFORMATION: /note= "Where n is inosine"

(xi) SEQUENCE DESCRIPTION: SEQ ID NO:12:

```
GGAATTCCCC NCAGCTNGTN TTCGAC                                    26
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:13:

```
Lys  Val  Phe  Asp  Glu
1                    5
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

```
GGATCCATGG TCAAGTCCCA CTACATCTGC                                30
```

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:15:

```
GAATTCAGAC CGGATAGAAA TAAGCCAATG AAA                            33
```

(2) INFORMATION FOR SEQ ID NO:16:

(i) SEQUENCE CHARACTERISTICS:
        (A) LENGTH: 701 amino acids
        (B) TYPE: amino acid
        (C) STRANDEDNESS:
        (D) TOPOLOGY: linear (xi) SEQUENCE DESCRIPTION: SEQ ID NO:16:

```
Met  Thr  Glu  Thr  Phe  Ala  Phe  Gln  Ala  Glu  Ile  Asn  Gln  Leu  Met  Ser
1                   5                        10                      15

Leu  Ile  Ile  Asn  Thr  Phe  Tyr  Ser  Asn  Lys  Glu  Ile  Phe  Leu  Arg  Asp
               20                      25                      30

Val  Ile  Ser  Asn  Ala  Ser  Asp  Ala  Cys  Asp  Lys  Ile  Arg  Tyr  Gln  Ser
          35                      40                      45

Leu  Thr  Asp  Pro  Ala  Val  Leu  Gly  Asp  Ala  Thr  Arg  Leu  Cys  Val  Arg
     50                      55                      60

Val  Val  Pro  Asp  Lys  Glu  Asn  Lys  Thr  Leu  Thr  Val  Glu  Asp  Asn  Gly
```

| | | | | 65 | | | | 70 | | | | 75 | | | | 80 |
|---|---|---|---|---|---|---|---|---|---|---|---|---|---|---|---|---|
| Ile | Gly | Met | Thr | Lys | Ala | Asp | Leu | Val | Asn | Asn | Leu | Gly | Thr | Ile | Ala |
| | | | | 85 | | | | 90 | | | | | | 95 | |
| Arg | Ser | Gly | Thr | Lys | Ala | Phe | Met | Glu | Ala | Leu | Glu | Ala | Gly | Ala | Asp |
| | | | | 100 | | | | 105 | | | | | | 110 | |
| Met | Ser | Met | Ile | Gly | Gln | Phe | Gly | Val | Gly | Phe | Tyr | Ser | Ala | Tyr | Leu |
| | | | | 115 | | | | 120 | | | | | | 125 | |
| Val | Ala | Asp | Arg | Val | Thr | Val | Thr | Ser | Lys | Asn | Asn | Ser | Asp | Glu | Val |
| | | | | 130 | | | | 135 | | | | | | 140 | |
| Tyr | Val | Trp | Glu | Ser | Ser | Ala | Gly | Gly | Thr | Phe | Thr | Ile | Thr | Ser | Ala |
| 145 | | | | | | 150 | | | | | 155 | | | | 160 |
| Pro | Glu | Ser | Asp | Met | Lys | Leu | Pro | Ala | Arg | Ile | Thr | Leu | His | Leu | Lys |
| | | | | 165 | | | | | | 170 | | | | 175 | |
| Glu | Asp | Gln | Leu | Glu | Tyr | Leu | Glu | Ala | Arg | Arg | Leu | Lys | Glu | Leu | Ile |
| | | | | 180 | | | | 185 | | | | | | 190 | |
| Lys | Lys | His | Ser | Glu | Phe | Ile | Gly | Tyr | Asp | Ile | Glu | Leu | Met | Val | Glu |
| | | | 195 | | | | | 200 | | | | | 205 | | |
| Lys | Thr | Thr | Glu | Lys | Glu | Val | Thr | Asp | Glu | Asp | Glu | Glu | Ala | Lys | |
| | 210 | | | | | 215 | | | | | 220 | | | | |
| Lys | Ala | Asp | Glu | Asp | Gly | Glu | Glu | Pro | Lys | Val | Glu | Glu | Val | Thr | Glu |
| 225 | | | | | 230 | | | | | 235 | | | | | 240 |
| Gly | Glu | Glu | Asp | Lys | Lys | Lys | Thr | Lys | Lys | Val | Lys | Glu | Val | Thr | |
| | | | | 245 | | | | | 250 | | | | | 255 | |
| Lys | Glu | Tyr | Glu | Val | Gln | Asn | Lys | His | Lys | Pro | Leu | Trp | Thr | Arg | Asp |
| | | | 260 | | | | | 265 | | | | | 270 | | |
| Pro | Lys | Asp | Val | Thr | Lys | Glu | Glu | Tyr | Ala | Ala | Phe | Tyr | Lys | Ala | Ile |
| | | 275 | | | | | 280 | | | | | 285 | | | |
| Ser | Asn | Asp | Trp | Glu | Asp | Pro | Pro | Ala | Thr | Lys | His | Phe | Ser | Val | Glu |
| | 290 | | | | | 295 | | | | | 300 | | | | |
| Gly | Gln | Leu | Glu | Phe | Arg | Ala | Ile | Met | Phe | Val | Pro | Lys | Arg | Ala | Pro |
| 305 | | | | | 310 | | | | | 315 | | | | | 320 |
| Phe | Asp | Met | Leu | Glu | Pro | Asn | Lys | Lys | Arg | Asn | Asn | Ile | Lys | Leu | Tyr |
| | | | | 325 | | | | | 330 | | | | | 335 | |
| Val | Arg | Arg | Val | Phe | Ile | Met | Asp | Asn | Cys | Glu | Asp | Leu | Cys | Pro | Asp |
| | | | 340 | | | | | 345 | | | | | 350 | | |
| Trp | Leu | Gly | Phe | Val | Lys | Gly | Val | Val | Asp | Ser | Glu | Asp | Leu | Pro | Leu |
| | | | 355 | | | | | 360 | | | | | 365 | | |
| Asn | Ile | Ser | Arg | Glu | Asn | Leu | Gln | Gln | Asn | Lys | Ile | Leu | Lys | Val | Ile |
| | 370 | | | | | 375 | | | | | 380 | | | | |
| Arg | Lys | Asn | Ile | Val | Lys | Lys | Cys | Leu | Glu | Met | Phe | Glu | Glu | Val | Ala |
| 385 | | | | | 390 | | | | | 395 | | | | | 400 |
| Glu | Asn | Lys | Glu | Asp | Tyr | Lys | Gln | Phe | Tyr | Glu | Gln | Phe | Gly | Lys | Asn |
| | | | | 405 | | | | 410 | | | | | | 415 | |
| Ile | Lys | Leu | Gly | Ile | His | Glu | Asp | Thr | Ala | Asn | Arg | Lys | Lys | Leu | Met |
| | | | 420 | | | | | 425 | | | | | 430 | | |
| Glu | Leu | Leu | Arg | Phe | Tyr | Ser | Thr | Glu | Ser | Gly | Glu | Val | Met | Thr | Thr |
| | | | 435 | | | | | 440 | | | | | 445 | | |
| Leu | Lys | Asp | Tyr | Val | Thr | Arg | Met | Lys | Ala | Glu | Gln | Asn | Ser | Ile | Tyr |
| | | 450 | | | | | 455 | | | | | 460 | | | |
| Tyr | Ile | Thr | Gly | Asp | Ser | Lys | Lys | Lys | Leu | Glu | Ser | Ser | Pro | Phe | Ile |
| 465 | | | | | 470 | | | | | 475 | | | | | 480 |
| Glu | Gln | Ala | Lys | Arg | Arg | Gly | Phe | Glu | Val | Leu | Phe | Met | Thr | Glu | Pro |
| | | | | 485 | | | | 490 | | | | | | 495 | |

```
Tyr  Asp  Glu  Tyr  Val  Met  Gln  Gln  Val  Lys  Asp  Phe  Glu  Asp  Lys  Lys
               500                      505                     510

Phe  Ala  Cys  Leu  Thr  Lys  Glu  Gly  Val  His  Phe  Glu  Glu  Ser  Glu  Glu
               515                      520                     525

Glu  Lys  Lys  Gln  Arg  Glu  Glu  Lys  Ala  Thr  Cys  Glu  Lys  Leu  Cys
     530                      535                     540

Lys  Thr  Met  Lys  Glu  Val  Leu  Gly  Asp  Lys  Val  Glu  Lys  Val  Thr  Val
545                      550                     555                          560

Ser  Glu  Arg  Leu  Ser  Thr  Ser  Pro  Cys  Ile  Leu  Val  Thr  Ser  Glu  Phe
               565                      570                     575

Gly  Trp  Ser  Ala  His  Met  Glu  Gln  Met  Met  Arg  Asn  Gln  Ala  Leu  Arg
               580                      585                     590

Asp  Ser  Ser  Met  Ala  Gln  Tyr  Met  Met  Ser  Lys  Lys  Thr  Met  Glu  Leu
          595                      600                     605

Asn  Pro  Lys  His  Pro  Ile  Ile  Lys  Glu  Leu  Arg  Arg  Arg  Val  Glu  Ala
     610                      615                     620

Asp  Glu  Asn  Asp  Lys  Ala  Val  Lys  Asp  Leu  Val  Phe  Leu  Leu  Phe  Asp
625                      630                     635                          640

Thr  Ser  Leu  Leu  Thr  Ser  Gly  Phe  Gln  Leu  Glu  Asp  Pro  Thr  Tyr  Ala
               645                      650                     655

Glu  Arg  Ile  Asn  Arg  Met  Ile  Lys  Leu  Gly  Leu  Ser  Leu  Asp  Glu  Glu
               660                      665                     670

Glu  Glu  Glu  Glu  Ala  Val  Glu  Ala  Ala  Val  Ala  Glu  Thr  Ala  Pro  Ala
          675                      680                     685

Glu  Val  Thr  Ala  Gly  Thr  Ser  Ser  Met  Glu  Leu  Val  Asp
     690                      695                     700
```

( 2 ) INFORMATION FOR SEQ ID NO:17:

( i ) SEQUENCE CHARACTERISTICS:
        ( A ) LENGTH: 704 amino acids
        ( B ) TYPE: amino acid
        ( C ) STRANDEDNESS:
        ( D ) TOPOLOGY: linear ( x i ) SEQUENCE DESCRIPTION: SEQ ID NO:17:

```
Met  Thr  Glu  Thr  Phe  Ala  Phe  Gln  Ala  Glu  Ile  Asn  Gln  Leu  Met  Ser
1                        5                      10                          15

Leu  Ile  Ile  Asn  Thr  Phe  Tyr  Ser  Asn  Lys  Glu  Ile  Phe  Leu  Arg  Glu
               20                       25                     30

Leu  Ile  Ser  Asn  Ala  Ser  Asp  Ala  Cys  Asp  Lys  Ile  Arg  Tyr  Gln  Ser
          35                       40                      45

Leu  Thr  Asn  Gln  Ala  Val  Leu  Gly  Asp  Glu  Ser  His  Leu  Arg  Ile  Arg
     50                       55                      60

Val  Val  Pro  Asp  Lys  Ala  Asn  Lys  Thr  Leu  Thr  Val  Glu  Asp  Thr  Gly
65                       70                      75                          80

Ile  Gly  Met  Thr  Lys  Ala  Glu  Leu  Val  Asn  Asn  Leu  Gly  Thr  Ile  Ala
               85                       90                     95

Arg  Ser  Gly  Thr  Lys  Ala  Phe  Met  Glu  Ala  Leu  Glu  Ala  Gly  Gly  Asp
               100                      105                    110

Met  Ser  Met  Ile  Gly  Gln  Phe  Gly  Val  Gly  Phe  Tyr  Ser  Ala  Tyr  Leu
          115                      120                     125

Val  Ala  Asp  Arg  Val  Thr  Val  Val  Ser  Lys  Asn  Asn  Asp  Asp  Glu  Ala
     130                      135                     140

Tyr  Thr  Trp  Glu  Ser  Ser  Ala  Gly  Gly  Thr  Phe  Thr  Val  Thr  Pro  Thr
145                      150                     155                         160
```

```
Pro Asp Cys Asp Leu Lys Arg Gly Thr Arg Ile Val Leu His Leu Lys
            165                 170                 175

Glu Asp Gln Gln Glu Tyr Leu Glu Arg Arg Leu Lys Asp Leu Ile
        180                 185                 190

Lys Lys His Ser Glu Phe Ile Gly Tyr Asp Ile Glu Leu Met Val Glu
            195                 200                 205

Lys Ala Thr Glu Lys Glu Val Thr Asp Glu Asp Glu Asp Glu Ala Ala
210                 215                 220

Ala Thr Lys Asn Glu Glu Gly Glu Glu Pro Lys Val Glu Glu Val Lys
225                 230                 235                 240

Asp Asp Ala Glu Glu Gly Glu Lys Lys Lys Thr Lys Lys Val Lys
                245                 250                 255

Glu Val Thr Gln Glu Phe Val Val Gln Asn Lys His Lys Pro Leu Trp
            260                 265                 270

Thr Arg Asp Pro Lys Asp Val Thr Lys Glu Glu Tyr Ala Ala Phe Tyr
        275                 280                 285

Lys Ala Ile Ser Asn Asp Trp Glu Glu Pro Leu Ser Thr Lys His Phe
    290                 295                 300

Ser Val Glu Gly Gln Leu Glu Phe Arg Ala Ile Leu Phe Val Pro Lys
305                 310                 315                 320

Arg Ala Pro Phe Asp Met Phe Glu Pro Ser Lys Lys Arg Asn Asn Ile
                325                 330                 335

Lys Leu Tyr Val Arg Arg Val Phe Ile Met Asp Asn Cys Glu Asp Leu
            340                 345                 350

Cys Pro Glu Trp Leu Ala Phe Val Arg Gly Val Val Asp Ser Glu Asp
        355                 360                 365

Leu Pro Leu Asn Ile Ser Arg Glu Asn Leu Gln Gln Asn Lys Ile Leu
    370                 375                 380

Lys Val Ile Arg Lys Asn Ile Val Lys Lys Ala Leu Glu Leu Phe Glu
385                 390                 395                 400

Glu Ile Ala Glu Asn Lys Glu Asp Tyr Lys Lys Phe Tyr Glu Gln Phe
                405                 410                 415

Gly Lys Asn Val Lys Leu Gly Ile His Glu Asp Ser Ala Asn Arg Lys
            420                 425                 430

Lys Leu Met Glu Leu Leu Arg Phe His Ser Ser Glu Ser Gly Glu Asp
        435                 440                 445

Met Thr Thr Leu Lys Asp Tyr Val Thr Arg Met Lys Glu Gly Gln Lys
    450                 455                 460

Cys Ile Tyr Tyr Val Thr Gly Asp Ser Lys Lys Lys Leu Glu Thr Ser
465                 470                 475                 480

Pro Phe Ile Glu Gln Ala Arg Arg Arg Gly Phe Glu Val Leu Phe Met
                485                 490                 495

Thr Glu Pro Ile Asp Glu Tyr Val Met Gln Gln Val Lys Asp Phe Glu
            500                 505                 510

Asp Lys Lys Phe Ala Cys Leu Thr Lys Glu Gly Val His Phe Glu Glu
        515                 520                 525

Thr Glu Glu Glu Lys Lys Gln Arg Glu Glu Glu Lys Thr Ala Tyr Glu
    530                 535                 540

Arg Leu Cys Lys Ala Met Lys Asp Val Leu Gly Asp Lys Val Glu Lys
545                 550                 555                 560

Val Val Val Ser Glu Arg Leu Ala Thr Ser Pro Cys Ile Leu Val Thr
                565                 570                 575

Ser Glu Phe Gly Trp Ser Ala His Met Glu Gln Ile Met Arg Asn Gln
            580                 585                 590
```

|   |   |   |   |   |   |   |   |   |   |   |   |   |   |   |
|---|---|---|---|---|---|---|---|---|---|---|---|---|---|---|
| Ala | Leu | Arg<br>595 | Asp | Ser | Ser | Met | Ser<br>600 | Ala | Tyr | Met | Met | Ser<br>605 | Lys | Lys | Thr |
| Met | Glu<br>610 | Ile | Asn | Pro | Ala | His<br>615 | Pro | Ile | Val | Lys | Glu<br>620 | Leu | Lys | Arg | Arg |
| Val<br>625 | Glu | Ala | Asp | Glu | Asn<br>630 | Asp | Lys | Ala | Val | Lys<br>635 | Asp | Leu | Val | Tyr | Leu<br>640 |
| Leu | Phe | Asp | Thr | Ala<br>645 | Leu | Leu | Thr | Ser | Gly<br>650 | Phe | Thr | Leu | Asp | Asp<br>655 | Pro |
| Thr | Ser | Tyr | Ala<br>660 | Glu | Arg | Ile | His | Arg<br>665 | Met | Ile | Lys | Leu<br>670 | Gly | Leu | Ser |
| Leu | Asp | Asp<br>675 | Glu | Asp | Asn | Gly | Asn<br>680 | Glu | Glu | Ala | Glu | Pro<br>685 | Ala | Ala | Ala |
| Val | Pro<br>690 | Ala | Glu | Pro | Val | Ala<br>695 | Gly | Thr | Ser | Ser | Met<br>700 | Glu | Gln | Val | Asp |

( 2 ) INFORMATION FOR SEQ ID NO:18:

( i ) SEQUENCE CHARACTERISTICS:
     ( A ) LENGTH: 732 amino acids
     ( B ) TYPE: amino acid
     ( C ) STRANDEDNESS:
     ( D ) TOPOLOGY: linear ( x i ) SEQUENCE DESCRIPTION: SEQ ID NO:18:

|   |   |   |   |   |   |   |   |   |   |   |   |   |   |   |   |
|---|---|---|---|---|---|---|---|---|---|---|---|---|---|---|---|
| Met<br>1 | Pro | Glu | Glu | Thr<br>5 | Gln | Thr | Gln | Asp | Gln<br>10 | Pro | Met | Glu | Glu | Glu<br>15 |
| Val | Glu | Thr | Phe<br>20 | Ala | Phe | Gln | Ala<br>25 | Glu | Ile | Ala | Gln | Leu<br>30 | Met | Ser | Leu |
| Ile | Ile | Asn<br>35 | Thr | Phe | Tyr | Ser | Asn<br>40 | Lys | Glu | Ile | Phe | Leu<br>45 | Arg | Glu | Leu |
| Ile | Ser<br>50 | Asn | Ser | Ser | Asp | Ala<br>55 | Leu | Asp | Lys | Ile | Arg<br>60 | Tyr | Glu | Ser | Leu |
| Thr<br>65 | Asp | Pro | Ser | Lys | Leu<br>70 | Asp | Ser | Gly | Lys | Glu<br>75 | Leu | His | Ile | Asn | Leu<br>80 |
| Ile | Pro | Asn | Lys | Gln<br>85 | Asp | Arg | Ala | Leu | Thr<br>90 | Ile | Val | Asp | Thr | Gly<br>95 | Ile |
| Gly | Met | Thr | Lys<br>100 | Ala | Asp | Leu | Ile | Asn<br>105 | Asn | Leu | Gly | Thr | Ile<br>110 | Ala | Lys |
| Ser | Gly | Thr<br>115 | Lys | Ala | Phe | Met | Glu<br>120 | Ala | Leu | Gln | Ala | Gly<br>125 | Ala | Asp | Ile |
| Ser | Met<br>130 | Ile | Gly | Gln | Phe | Gly<br>135 | Val | Gly | Phe | Tyr | Ser<br>140 | Ala | Tyr | Leu | Val |
| Ala<br>145 | Glu | Lys | Val | Thr | Val<br>150 | Ile | Thr | Lys | His | Asn<br>155 | Asp | Asp | Glu | Gln | Tyr<br>160 |
| Ala | Trp | Glu | Ser | Ser<br>165 | Ala | Gly | Gly | Ser | Phe<br>170 | Thr | Val | Arg | Thr | Asp<br>175 | Thr |
| Gly | Glu | Pro | Met<br>180 | Gly | Arg | Gly | Thr | Lys<br>185 | Val | Ile | Leu | His | Leu<br>190 | Lys | Glu |
| Asp | Gln | Thr<br>195 | Glu | Tyr | Leu | Glu | Glu<br>200 | Arg | Arg | Ile | Lys | Glu<br>205 | Ile | Val | Lys |
| Lys | His<br>210 | Ser | Gln | Phe | Ile | Gly<br>215 | Tyr | Pro | Ile | Thr | Leu<br>220 | Phe | Val | Glu | Lys |
| Glu<br>225 | Arg | Asp | Lys | Glu | Val<br>230 | Ser | Asp | Asp | Glu | Ala<br>235 | Glu | Glu | Lys | Glu | Asp<br>240 |
| Lys | Glu | Glu | Glu | Lys<br>245 | Glu | Lys | Glu | Glu | Lys<br>250 | Glu | Ser | Glu | Asp | Lys<br>255 | Pro |

```
Glu  Ile  Glu  Asp  Val  Gly  Ser  Asp  Glu  Asp  Glu  Lys  Lys  Asp  Gly
          260                 265                      270

Asp  Lys  Lys  Lys  Lys  Lys  Ile  Lys  Glu  Lys  Tyr  Ile  Asp  Lys  Glu
               275                 280                 285

Glu  Leu  Asn  Lys  Thr  Lys  Pro  Ile  Trp  Thr  Arg  Asn  Pro  Asp  Asp  Ile
          290                 295                      300

Thr  Asn  Glu  Glu  Tyr  Gly  Glu  Phe  Tyr  Lys  Ser  Leu  Thr  Asn  Asp  Trp
305                      310                 315                           320

Glu  Asp  His  Leu  Ala  Val  Lys  His  Phe  Ser  Val  Glu  Gly  Gln  Leu  Glu
                    325                      330                      335

Phe  Arg  Ala  Leu  Leu  Phe  Val  Pro  Arg  Arg  Ala  Pro  Phe  Asp  Leu  Phe
               340                 345                      350

Glu  Asn  Arg  Lys  Lys  Lys  Asn  Asn  Ile  Lys  Leu  Tyr  Val  Arg  Arg  Val
               355                 360                      365

Phe  Ile  Met  Asp  Asn  Cys  Glu  Glu  Leu  Ile  Pro  Glu  Tyr  Leu  Asn  Phe
          370                 375                      380

Ile  Arg  Gly  Val  Val  Asp  Ser  Glu  Asp  Leu  Pro  Leu  Asn  Ile  Ser  Arg
385                      390                 395                           400

Glu  Met  Leu  Gln  Gln  Ser  Lys  Ile  Leu  Lys  Val  Ile  Arg  Lys  Asn  Leu
                    405                      410                      415

Val  Lys  Lys  Cys  Leu  Glu  Leu  Phe  Thr  Glu  Leu  Ala  Glu  Asp  Lys  Glu
               420                 425                      430

Asn  Tyr  Lys  Lys  Phe  Tyr  Glu  Gln  Phe  Ser  Lys  Asn  Ile  Lys  Leu  Gly
               435                 440                      445

Ile  His  Glu  Asp  Ser  Gln  Asn  Arg  Lys  Lys  Leu  Ser  Glu  Leu  Leu  Arg
          450                 455                      460

Tyr  Tyr  Thr  Ser  Ala  Ser  Gly  Asp  Glu  Met  Val  Ser  Leu  Lys  Asp  Tyr
465                      470                 475                           480

Cys  Thr  Arg  Met  Lys  Glu  Asn  Gln  Lys  His  Ile  Tyr  Tyr  Ile  Thr  Gly
               485                 490                      495

Glu  Thr  Lys  Asp  Gln  Val  Ala  Asn  Ser  Ala  Phe  Val  Glu  Arg  Leu  Arg
          500                 505                      510

Lys  His  Gly  Leu  Glu  Val  Ile  Tyr  Met  Ile  Glu  Pro  Ile  Asp  Glu  Tyr
          515                 520                      525

Cys  Val  Gln  Gln  Leu  Lys  Glu  Phe  Glu  Gly  Lys  Thr  Leu  Val  Ser  Val
     530                 535                      540

Thr  Lys  Glu  Gly  Leu  Glu  Leu  Pro  Glu  Asp  Glu  Glu  Glu  Lys  Lys  Lys
545                      550                 555                           560

Gln  Glu  Glu  Lys  Lys  Thr  Lys  Phe  Glu  Asn  Leu  Cys  Lys  Ile  Met  Lys
                    565                      570                      575

Asp  Ile  Leu  Glu  Lys  Lys  Val  Glu  Lys  Val  Val  Val  Ser  Asn  Arg  Leu
               580                 585                      590

Val  Thr  Ser  Pro  Cys  Cys  Leu  Val  Thr  Ser  Thr  Tyr  Gly  Trp  Thr  Ala
          595                 600                      605

Asn  Met  Glu  Arg  Ile  Met  Lys  Ala  Gln  Ala  Leu  Arg  Asp  Asn  Ser  Thr
          610                 615                      620

Met  Gly  Tyr  Met  Ala  Ala  Lys  Lys  His  Leu  Glu  Ile  Asn  Pro  Asp  His
625                      630                 635                           640

Ser  Ile  Ile  Glu  Thr  Leu  Arg  Gln  Lys  Ala  Glu  Ala  Asp  Lys  Asn  Asp
                    645                      650                      655

Lys  Ser  Val  Lys  Asp  Leu  Val  Ile  Leu  Leu  Tyr  Glu  Thr  Ala  Leu  Leu
               660                 665                      670

Ser  Ser  Gly  Phe  Ser  Leu  Glu  Asp  Pro  Gln  Thr  His  Ala  Asn  Arg  Ile
```

-continued

|   |   | 675 |   |   |   |   | 680 |   |   |   | 685 |   |   |   |
|---|---|---|---|---|---|---|---|---|---|---|---|---|---|---|
| Tyr | Arg | Met | Ile | Lys | Leu | Gly | Leu | Gly | Ile | Asp | Glu | Asp | Asp | Pro | Thr |
|   | 690 |   |   |   |   | 695 |   |   |   | 700 |   |   |   |   |
| Ala | Asp | Asp | Thr | Ser | Ala | Ala | Val | Thr | Glu | Glu | Met | Pro | Pro | Leu | Glu |
| 705 |   |   |   |   | 710 |   |   |   | 715 |   |   |   |   | 720 |
| Gly | Asp | Asp | Asp | Thr | Ser | Arg | Met | Glu | Glu | Val | Asp |
|   |   |   |   | 725 |   |   |   | 730 |   |   |   |

LEISHMANIA ANTIGENS FOR USE IN THE THERAPY AND DIAGNOSIS OF LEISHMANIASIS

STATEMENT OF GOVERNMENT INTEREST

This invention may have been made with government support. The government may have certain rights in the invention.

TECHNICAL FIELD

The present invention relates generally to compositions and methods for preventing, treating and detecting leishmaniasis, and for stimulating immune responses in patients. The invention is more particularly related to polypeptides comprising an immunogenic portion of a Leishmania antigen or a variant thereof, and to vaccines and pharmaceutical compositions comprising one or more such polypeptides. The vaccines and pharmaceutical compositions may be used, for example, for the prevention and therapy of leishmaniasis, as well as for the detection of Leishmania infection in patients and blood supplies.

BACKGROUND OF THE INVENTION

Leishmania organisms are intracellular protozoan parasites of macrophages that cause a wide range of clinical diseases in humans and other animals, primarily dogs. In some infections, the parasite may lie dormant for many years. In other cases, the host may develop one of a variety of forms of leishmaniasis. For example, the disease may be asymptomatic or may be manifested as subclinical visceral leishmaniasis, which is characterized by mild symptoms of malaise, diarrhea and intermittent hepatomegaly. Patients with subclinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Accurate diagnosis of leishmaniasis is also frequently difficult to achieve. There are 20 species of Leishmania that infect humans, including *L. donovani, L. chagasi, L. infantum, L. major, L. amazonensis, L. braziliensis, L. panamensis, L. tropica,* and *L. guyanensis,* and there are no distinctive signs or symptoms that unambiguously indicate the presence of Leishmania infection. Parasite detection methods have been used, but such methods are not sensitive or practical. Current serological tests (using, for example, ELISA or immunofluorescence techniques) and skin tests typically use whole or lysed parasites. Such tests are generally insensitive, irreproducible and prone to cross-reaction with a variety of other diseases. In addition, the preparations employed in such tests are often unstable.

Accordingly, there is a need in the art for vaccines to prevent leishmaniasis in humans and dogs, and for improved therapeutic compositions for the treatment of leishmaniasis. There is also a need for improved methods of detecting Leishmania infection in patients and in blood supplies. The present invention fulfills these needs and further provides other related advantages.

SUMMARY OF THE INVENTION

Briefly stated, the present invention provides compositions and methods for preventing, treating and detecting leishmaniasis, as well as for stimulating immune responses in patients. In one aspect polypeptides are provided, comprising at least an immunogenic portion of a Leishmania antigen, or a variant of such an antigen that differs only in conservative substitutions and/or modifications. In one embodiment of this aspect, the Leishmania antigen has the amino acid sequence recited in SEQ ID NO:2. In another embodiment, the Leishmania antigen has the amino acid sequence recited in SEQ ID NO:4. DNA sequences encoding the above polypeptides, recombinant expression vectors comprising these DNA sequences and host cells transformed or transfected with such expression vectors are also provided.

In related aspects, the present invention provides pharmaceutical compositions which comprise at least an immunogenic portion of a Leishmania antigen (or a variant of such an antigen that differs only in conservative substitutions and/or modifications) as described herein and a physiologically acceptable carrier. In addition, vaccines which comprise at least an immunogenic portion of a Leishmania antigen (or a variant of such an antigen that differs only in conservative substitutions and/or modifications) as described herein and a non-specific immune response enhancer are also provided. In one embodiment of these aspects, the Leishmania antigen has the amino acid sequence recited in SEQ ID NO:2. In another embodiment, the Leishmania antigen has the amino acid sequence recited in SEQ ID NO:4.

In still further related embodiments, the pharmaceutical compositions and vaccines comprise at least two different polypeptides selected from the group consisting of: (a) a polypeptide comprising an immunogenic portion of a Leishmania antigen having the amino acid sequence recited in SEQ ID NO:2, or a variant of such an antigen that differs only in conservative substitutions and/or modifications; (b) a polypeptide comprising an immunogenic portion of a Leishmania antigen having the amino acid sequence recited in SEQ ID NO:4, or a variant of such an antigen that differs only in conservative substitutions and/or modifications; (c) a polypeptide comprising an immunogenic portion of a Leishmania antigen having the amino acid sequence recited in SEQ ID NO:6, or a variant of said antigen that differs only in conservative substitutions and/or modifications; (d) a polypeptide comprising an immunogenic portion of a Leishmania antigen having the amino acid sequence recited in SEQ ID NO:8, or a variant of said antigen that differs only in conservative substitutions and/or modifications; and (e) a polypeptide comprising an immunogenic portion of a Leishmania antigen having the amino acid sequence recited in SEQ ID NO:10, or a variant of said antigen that differs only in conservative substitutions and/or modifications.

In other related embodiments, the pharmaceutical compositions and vaccines comprise soluble Leishmania antigens.

In another aspect, the present invention provides methods for inducing protective immunity against leishmaniasis in a patient, comprising administering to a patient a pharmaceutical composition or vaccine as described above.

In further aspects, methods and diagnostic kits are provided for detecting Leishmania infection in a patient. The methods comprise: (a) contacting dermal cells of a patient with a pharmaceutical composition as described above; and (b) detecting an immune response on the patient's skin, and therefrom detecting Leishmania infection in the patient. The diagnostic kits comprise: (a) a pharmaceutical composition as described above; and (b) an apparatus sufficient to contact the pharmaceutical composition with the dermal cells of a patient.

In further aspects, the present invention provides methods for stimulating a cellular and/or humoral immune response in a patient, comprising administering to a patient a pharmaceutical composition or vaccine as described above.

In a related aspect, methods are provided for treating a patient afflicted with a disease responsive to IL-12 stimulation, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 19 presents a comparison of a Lbhsp83 sequence with homologous sequences from *L. amazonensis* (Lahsp83) SEQ ID NO:16, *T cruzi* (Tchsp83) SEQ ID NO:17 and humans (Huhsp89) SEQ ID NO:18.

DETAILED DESCRIPTION OF THE INVENTION

Figure 1:
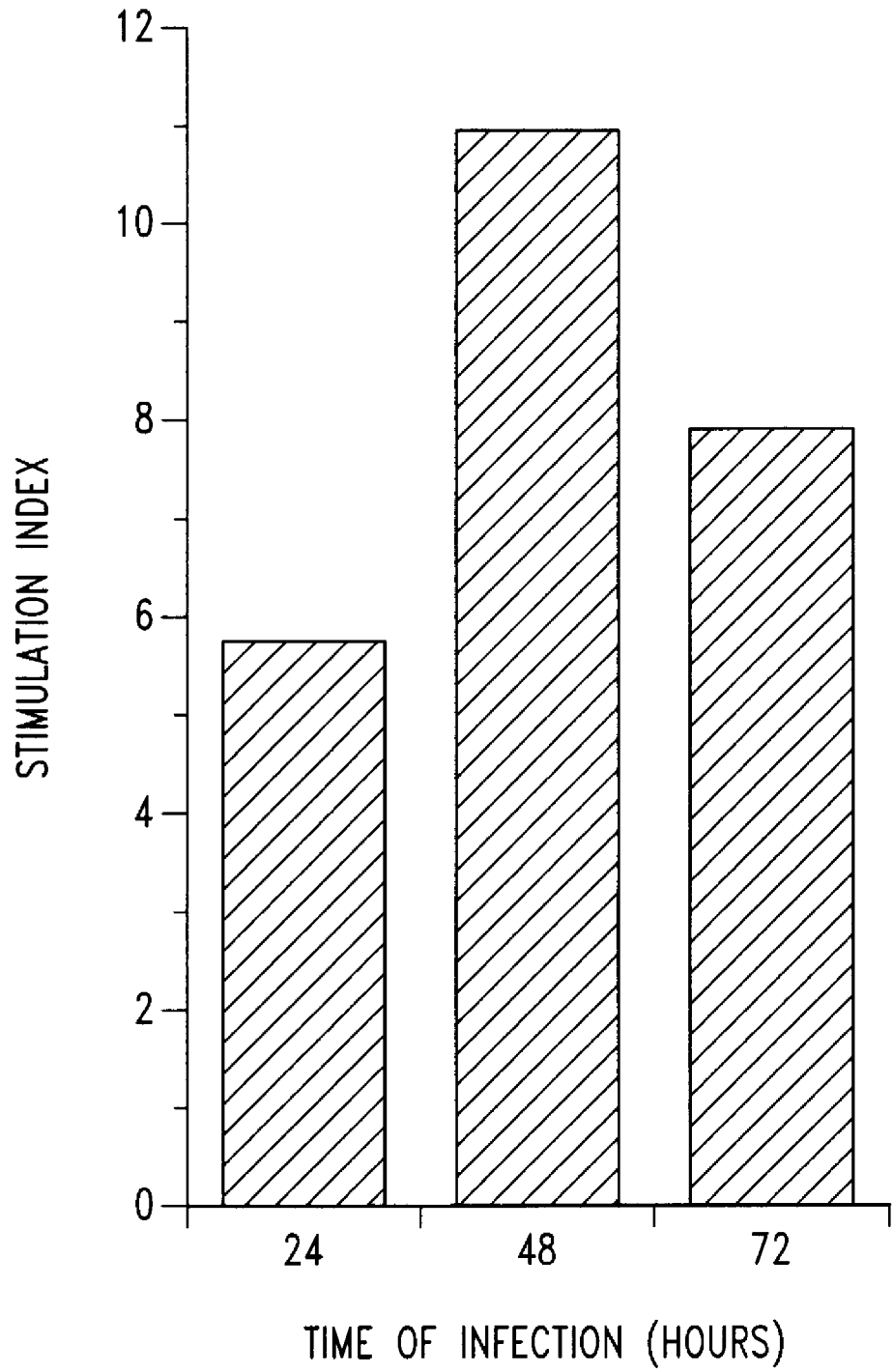
FIG. 1 shows the stimulation of proliferation of T-cells obtained from L. donovani-immunized BALB/c mice (represented by stimulation index) by L. donovani-infected macrophages after incubation for 24, 48 and 72 hours.
Figure 2A:
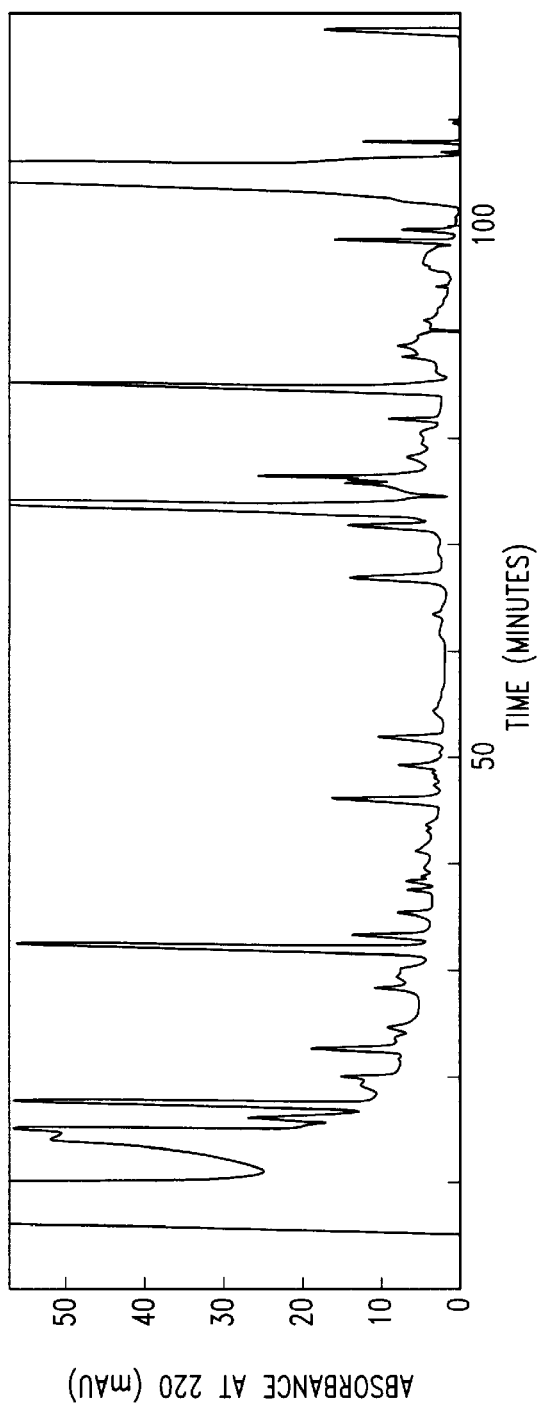
FIG. 2 illustrates representative HPLC profiles of peptides isolated from MHC class II molecules of P388D1 macrophages. Panel A shows peptides isolated from uninfected macrophages and panel B shows peptides isolated from L. donovani infected macrophages. The arrows in panel B indicate peptide peaks present only in the infected macrophage preparation.
Figure 2B:
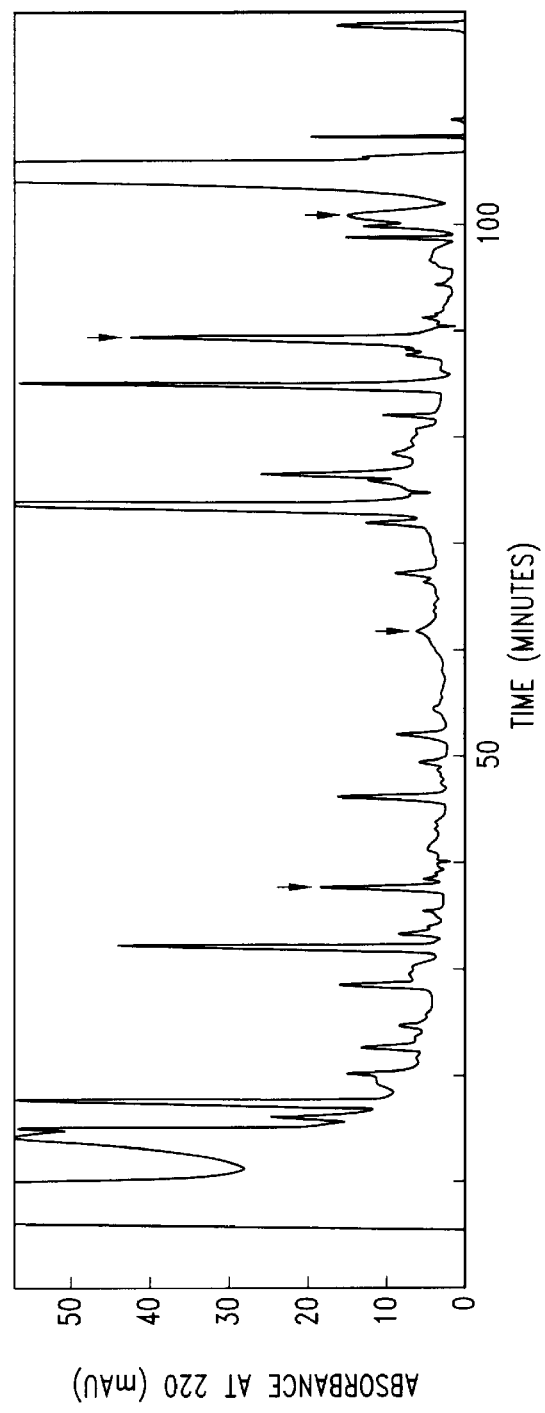

As noted above, the present invention is generally directed to compositions and methods for preventing, treating and detecting leishmaniasis, as well as for stimulating immune responses in patients. The compositions of the subject invention include polypeptides that comprise at least an immunogenic portion of a Leishmania antigen, or a variant of such an antigen that differs only in conservative substitutions and/or modifications. In one preferred embodiment, compositions of the present invention include multiple polypeptides selected so as to provide enhanced protection against a variety of Leishmania species.

Polypeptides within the scope of the present invention include, but are not limited to, polypeptides comprising immunogenic portions of Leishmania antigens having the sequences recited in SEQ ID NO:2 (referred to herein as M15), SEQ ID NO:4 (referred to herein as Ldp23), SEQ ID NO:6 (referred to herein as Lbhsp83), SEQ ID NO:8 (referred to herein as Lt-210) and SEQ ID NO:10 (referred to herein as LbeIF4A). As used herein, the term "polypeptide" encompasses amino acid chains of any length, including full length proteins (i.e., antigens), wherein the amino acid residues are linked by covalent bonds. Thus, a polypeptide comprising an immunogenic portion of one of the above antigens may consist entirely of the immunogenic portion, or may contain additional sequences. The additional sequences may be derived from the native Leishmania antigen or may be heterologous, and such sequences may (but need not) be immunogenic. An antigen "having" a particular sequence is an antigen that contains, within its full length sequence, the recited sequence. The native antigen may, or may not, contain additional amino acid sequence.

An immunogenic portion of a Leishmania antigen is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/or B cells). In particular, immunogenic portions are capable of inducing T-cell proliferation and/or a dominantly Th1-type cytokine response (e.g, IL-2, IFN-γ, and/or TNF-α production by T-cells and/or NK cells; and/or IL-12 production by monocytes, macrophages and/or B cells). Immunogenic portions of the antigens described herein may generally be identified using techniques known to those of ordinary skill in the art, such as the representative methods provided herein.

The compositions and methods of the present invention also encompass variants of the above polypeptides. A "variant," as used herein, is a polypeptide that differs from the native antigen only in conservative substitutions and/or modifications, such that the ability of the polypeptide to induce an immune response is retained. Such variants may generally be identified by modifying one of the above polypeptide sequences and evaluating the immunogenic properties of the modified polypeptide using, for example, the representative procedures described herein.

A "conservative substitution" is one in which an amino acid is substituted for another amino acid that has sinilar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, lie, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

"Polypeptides" as described herein also include combination polypeptides. A "combination polypeptide" is a polypeptide comprising at least one of the above immunogenic portions and one or more additional immunogenic Leishmania sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

In general, Leishmania antigens having immunogenic properties, and DNA sequences encoding such antigens, may be prepared using any of a variety of procedures from one or more Leishmania species including, but not limited to, *L. donovani, L. chagasi, L. infantum, L. major, L. amazonensis, L. braziliensis, L. panamensis, L. tropica*, and *L. guyanensis*. Such species are available, for example, from ATCC, Rockville, Md. For example, peptides isolated from MHC class II molecules of macrophages infected with a Leishmania species may be used to rescue the corresponding Leishmania donor antigens. MHC class II molecules are expressed mainly by cells of the immune system, including macrophages. These molecules present peptides, which are usually 13–17 amino acids long, derived from foreign antigens that are degraded in cellular vesicles. The bound peptide antigens are then recognized by CD4 T-cells. Accordingly, foreign peptides isolated from MHC class II molecules of, for example, Leishmania-infected murine macrophages may be used to identify immunogenic Leishmania proteins.

Briefly, peptides derived from Leishmania antigens may be isolated by comparing the reverse phase HPLC profile of peptides extracted from infected macrophages with the profile of peptides extracted from uninfected cells. Peptides giving rise to distinct HPLC peaks unique to infected macrophages may then be sequenced using, for example, Edman chemistry as described in Edman and Berg, *Eur J. Biochem*, 80:116–132 (1967). A DNA fragment corresponding to a portion of a Leishmania gene encodin(g the peptide may then be amplified from a Leishmania cDNA library using an oligonucleotide sense primer derived from the peptide sequence and an oligo dT antisense primer. The resulting DNA fragment may then be used as a probe to screen a Leishmania library for a full length cDNA or genomic clone that encodes the Leishmania antigen. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y. (1989).

This approach may be used to identify a 23 kD *Leishmania donovani* antigen (referred to herein as Ldp23). The sequence of a DNA molecule encoding Ldp23 is provided in SEQ ID NO:3 and the amino acid sequence of Ldp23 is provided in SEQ ID NO:4. Using the methods described herein, Ldp23 has been shown to induce a Th1 immune response in T-cells prepared from Leishmania-infected mice.

Alternatively, a Leishmania cDNA or genomic expression library may be screened with serum from a Leishmania-infected individual, using techniques well known to those of ordinary skill in the art. DNA molecules encoding reactive antigens may then be used to express the recombinant antigen for purification. The immunogenic properties of the purified Leishmania antigens may then be evaluated using, for example the representative methods described herein.

For example, sera from Leishmania-infected mice may be used to screen a cDNA library prepared from Leishmania amastigotes. Reactive clones may then be expressed and recombinant proteins assayed for the ability to stimulate T-cells or NK cells derived from Leishmania-immune individuals (i.e., individuals having evidence of infection, as documented by positive serological reactivity with Leishmania-specific antibodies and/or a Leishmania-specific DTH response, without clinical symptoms of leishmaniasis). This procedure may be used to obtain a recombinant DNA molecule encoding the Leishmania antigen designated M15. The sequence of such a DNA molecule is provided in SEQ ID NO:1, and the amino acid sequence of the encoded protein is provided in SEQ ID NO:2.

A similar approach may be used to isolate a genomic DNA molecule encoding an immunogenic *Leishmania braziliensis* antigen, referred to herein as Lbhsp83. More specifically, a genomic clone encoding Lbhsp83 may be isolated by screening a *L. braziliensis* expression library with sera from a Leishmania-infected individual. The DNA encoding Lbhsp83 is homologous to the gene encoding the eukaryotic 83 kD heat shock protein. The sequence of a DNA molecule encoding nearly all of Lbhsp83 is presented in SEQ ID NO:5, and the encoded amino acid sequence is provided in SEQ ID NO:6. Using the methods described below, Lbhsp83 has been found to stimulate proliferation, and a mixed Th1 and Th2 cytokine profile, in PBMC isolated from *L. braziliensis*-infected patients. Accordingly, Lbhsp83 is an immunogenic Leishmania antigen. Regions of Lbhsp83 that are not conserved with the mammalian gene have been found to be particularly potent for T-cell stimulation and antibody binding. Such regions may be identified, for example, by visual inspection of the sequence comparison provided in FIG. 19.

This approach may also be used to isolate a DNA molecule encoding a 210 kD immunogenic *L. tropica* antigen, referred to herein as Lt-210. The preparation and characterization of Lt-210, and immunogenic portions thereof (such as Lt-1 and immunogenic repeat and non-repeat sequences), is described in detail in U.S. patent application Ser. No. 08/511,872, filed Aug. 4, 1995. The sequence of a DNA molecule encoding Lt-1 is provided in SEQ ID NO:7 and the encoded amino acid sequence is presented in SEQ ID NO:8.

The above approach may further be used to isolate a DNA molecule encoding a *L. braziliensis* antigen referred to herein as LbeIF4A. Briefly, such a clone may be isolated by screening a *L. braziliensis* expression library with sera obtained from a patient afflicted with mucosal leishmaniasis, and analyzing the reactive antigens for the ability to stimulate proliferative responses and preferential Th1 cytokine production in PBMC isolated from Leishmania-infected patients, as described below. The preparation and characterization of LbeIF4A is described in detail in U.S. patent application Ser. Nos. 08/454,036 and 08/488,386, which are continuations-in-part of U.S. patent application Ser. No. 08/232,534, filed Apr. 22, 1994. The sequence of a DNA molecule encoding LbeIF4A is provided in SEQ ID NO:9 and the encoded amino acid sequence is presented in SEQ ID NO:10. Homologs of LbeIF4A, such as that found in *L. major*, may also be isolated using this approach, and are within the scope of the present invention.

Compositions of the present invention may also, or alternatively, contain soluble Leishmania antigens. As used herein, "soluble Leishmania antigens" refers to a mixture of at least 8 different Leishmania antigens that may be isolated from the supernatant of Leishmania promastigotes of any species grown for 8–12 hours in protein-free medium. Briefly, the organisms are grown to late log phase in complex medium with serum until they reach a density of $2–3\times10^7$ viable organisms per mL of medium. The organisms are thoroughly washed to remove medium components and resuspended at $2–3\times10^7$ viable organisms per mL of defined serum-free medium consisting of equal parts RPMI 1640 and medium 199, both from Gibco BRL, Gaithersburg, M.D. After 8–12 hours, the supernatant containing soluble Leishmania antigens is removed, concentrated 10 fold and dialyzed against phosphate-buffered saline for 24 hours. The presence of at least eight different antigens within the mixture of Leishmania antigens may be confirmed using SDS-PAGE (i.e., through the observation of at least 8 different bands). The immunogenic properties of the soluble Leishmania antigens may be confirmed by evaluating the ability of the preparation to elicit an immune response in cultures of lymph node cells and/or peripheral blood mononuclear cells (PBMC) isolated from presently or previously Leishmania-infected individuals. Such an evaluation may be performed as described below.

Regardless of the method of preparation, the antigens described herein are immunogenic. In other words, the antigens (and immunogenic portions thereof) are capable of eliciting an immune response in cultures of lymph node cells and/or peripheral blood mononuclear cells (PBMC) isolated from presently or previously Leishmania-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously Leishmania-infected individuals. A Leishmania-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with at least one of the following: isolation of parasite from lesions, a positive skin test with Leishmania lysate or a positive serological test. Asymptomatic individuals are infected individuals who have no signs or symptoms of the disease, but such individuals can be identified based on a positive serological test and/or skin test with Leishmania lysate.

The term "PBMC," which refers to a preparation of nucleated cells that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with Leishmania promastigotes emulsified in complete Freund's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a polypeptide (e.g., a Leishmania antigen or a portion or other variant thereof) to induce a response in PBMC or lymph node cell cultures may be evaluated by contacting the cells with the polypeptide and measuring a suitable response. In general, the amount of polypeptide that is sufficient for the evaluation of about $2 \times 10^5$ cells ranges from about 10 ng to about 100 μg, and preferably is about 1–10 μg. The incubation of polypeptide with cells is typically performed at 37° C. for about 1–3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the level of mRNA encoding one or more specific cytokines. In particular, the secretion of interferon-γ, interleukin-2, tumor necrosis factor-α and/or interleukin-12 is indicative of a Th1 response, which is responsible for the protective effect against Leishmania. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3 \times 10^5$ cells, the production of 30 pg/nL of IL-12, IL-4, IFN-γ, TNF-α or IL-12 p40, or 10 pg/mL of IL-12 p70, is considered able to stimulate production of a cytokine.

Immunogenic portions of the antigens described herein may be prepared and identified using well known techniques, such as those summarized in Paul, Fundamental Immunology, 3rd ed., 243–247 (Raven Press, 1993) and references cited therein. Such techniques include screening polypeptides derived from the native antigen for immunogenic properties using, for example, the representative techniques described herein. An immunogenic portion of a polypeptide is a portion that, within such representative assays, generates an immune response (e.g., proliferation and/or cytokine production) that is substantially similar to that generated by the full length antigen. In other words, an immunogenic portion of an antigen may generate at least about 25%, and preferably at least about 50%, of the response generated by the full length antigen in the model assays described herein.

Portions and other variants of immunogenic Leishmania antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions.

Recombinant polypeptides containing portions and/or variants of a native antigen may be readily prepared from a DNA sequence encoding the antigen. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

In general, any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof. For example, variants of a native antigen may generally be prepared using standard mutagenesis techniques, such as oligonucleotide-directed site-specific mutagenesis, and sections of the DNA sequence may be removed to permit preparation of truncated polypeptides.

In certain aspects of the present invention, described in detail below, the polypeptides and/or soluble Leishmania antigens may be incorporated into pharmaceutical compositions or vaccines. Pharmaceutical compositions comprise one or more polypeptides, each of which may contain one or more of the above sequences (or variants thereof), and a physiologically acceptable carrier. Vaccines comprise one or more of the above polypeptides and a non-specific immune response enhancer, such as an adjuvant (e.g., LbeIF4A, interleukin- 12 or other cytokines) or a liposome (into which the polypeptide is incorporated). Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other Leishmania antigens, either incorporated into a combination polypeptide or present within one or more separate polypeptides.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordella pertussis* or *Mycobacterium tuberculosis*. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Preferred adjuvants include LbeIF4A, IL-12 and other cytokines such as IFN-γ or granulocyte-macrophage colony stimulating factor (GM-CSF). By virtue of its ability to induce an exclusive Th1 immune response, the use of LbeIF4A, and variants thereof, as an adjuvant in the vaccines of the present invention is particularly preferred.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by individual polypeptides may be additive, (2) stimulation of proliferation and/or cytokine production by individual polypeptides may be synergistic, (3) individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M 15, Ldp23, Lbhsp83, Lt-1 and LbeIF4A. Alternatively, or in addition, the combination may comprise soluble Leishmania antigens.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical compositions and vaccines described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-γ, as well as tumor necrosis factor-α). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of LbeIF4A (or a variant thereof), M15, soluble Leishmania antigens and/or Ldp23 (or a variant thereof). Polypeptides comprising an immunogenic portion of Lbhsp83 and/or Lt-1 may also be used, in combination with a polypeptide that contains at least an immunogenic portion of LbeIF4A. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1 and LbeIF4A. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of M15, Ldp23, Lbhsp83, Lt-1 and LbeIF4A. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (i.e., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1–2 years. In general, the amount of polypeptide present in a dose (or produced in situ by the DNA in a dose) ranges from about 100 ng to about 1 mg per kg of host, typically from about 10 µg to about 100 µg. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 µg to 100 µg, preferably from about 10 µg to 50 µg in a volume of 0.1 mL. Preferably, the carrier employed in such pharmaceutical compositions is a saline solution with appropriate preservatives, such as phenol and/or Tween 80™.

The following Examples are offered by way of illustration and not by way of limitation.

EXAMPLES

Example 1

Preparation of M15

This Example illustrates the preparation of a Leishmania antigen M15, having the sequence provided in SEQ ID NO:2.

An *L. major* (Friedlan strain) amastigote cDNA expression library prepared in the λZAP II vector (Stratagene, La Jolla, Calif.) was screened according to manufacturer's instructions using sera obtained from *L. major* infected BALB/c mice (8 weeks post inoculation). Approximately 40,000 plaques were screened and four clones expressing reactive antigens were purified to homogeneity by two subsequent rounds of low density screening. Bluescript phagemid inserts were excised from positive clones for further analysis. An EcoRI/SstII restriction fragment from the 5' end of one partial cDNA insert isolated during first round screening (pLma1-1) was subsequently used as a probe to rescreen for clones containing full length cDNA inserts. The probe was labeled to high specific activity (~$10^9$ cpm/µg) with [α-$^{32}$P]dCTP using the random primer method and was used to screen ~10,000 plaques of the *L. major* expression library described above. Positive clones were compared by restriction enzyme digestion and the clone with the largest insert (pfl1-1) was chosen for subsequent analysis.

DNA sequence analyses were performed on an Applied Biosystems automated sequencer using Taq polymerase and dye coupled ddNTP terminators or dye-labeled sequencing primers. The complete sequence of the 2685 bp insert was determined using a combination of primer-directed sequencing and by sequencing a series of overlapping Exonuclease III deletion subclones generated using the Erase-a-base system (Promega, Madison, Wis.). The sequence of this insert is provided in SEQ ID NO:1, and the deduced amino acid sequence is provided in SEQ ID NO:2.

The complete insert of clone pfl-1 was excised by digestion with BamHI/KpnI and was subcloned in frame into BamHI/KpnI digested pQE31 (QUIAGEN) to generate the construct pM151A. *E. coli* containing this construct inducibly expressed high levels of the *L. major* antigen encoded by pfl1-1 (designated as M15) with the addition of a 6-histidine tag at the amino terminus. Large volume cultures (500 ml) of *E. coli* host cells containing the pM151A construct were induced to express recombinant protein by the addition of 2 mM IPTG at mid-log phase of growth. Growth was continued for 4 to 5 hours and bacteria were then pelleted and washed once with cold PBS. Bacteria were resuspended in 20 ml of lysis buffer (50 mM $Na_2HPO_4$, pH 8.0, 300 mM NaCl, 10 mM β-mercaptoethanol) containing 20 mg of lysozyme and were lysed by a 1 hour incubation at 4° C. followed by brief sonication. Insoluble material was removed by centrifugation at 10,000×g for 10 minutes and although the recombinant protein was found to be evenly distributed between the soluble and insoluble fractions the insoluble material was discarded at this point. Recombinant protein containing the amino terminal histidine tag was affinity purified using Ni-NTA resin (QIAGEN) according to the manufacturer's recommendations. Briefly, 8 ml of Ni-NTA resin resuspended in lysis buffer was added to the soluble lysate fraction and binding was conducted with constant mixing for 1 hour at 4° C. The mixture was then loaded into a gravity flow column and the non-binding material was allowed to flow through. The Ni-NTA matrix was washed 3 times with 25 ml of wash buffer (50 mM $Na_2HPO_4$, pH 6.0, 300 mM NaCl, 10 mM β-mercaptoethanol) and bound material was eluted in 25 ml of elution buffer (50 mM $Na_2HPO_4$, pH 5.0, 300 mM NaCl, 10 mM β-mercaptoethanol). The eluted material was then dialyzed against 3 changes of PBS, sterile filtered and stored at −20° C. The purified recombinant protein was shown by SDS-PAGE analysis to be free of any significant amount of *E. coli* protein. A small number of bands of lower molecular weight were assumed to be proteolytic products of the *L. major* antigen based on their reactivity by western blot analysis. A high titre polyclonal antisera against M15 was generated in rabbits by repeated subcutaneous injection of recombinant protein. Western blot analysis of lysates from *L. major* promastigotes and amastigotes using this antisera indicated that the protein is constitutively expressed throughout the parasite lifecycle.

Example 2

Preparation of Ldp23

This Example illustrates the preparation of a Leishmania antigen Ldp23, having the sequence provided in SEQ ID NO:4.

A. Purification of MHC Class II-associated Peptides from P388D1 Macrophages Infected with *L. donovani*

To ascertain that in vitro infection of macrophages would load their MHC class II molecules with parasite peptides, initial experiments were carried out to test the ability of *L. donovani*-infected macrophage cell line P388D1 to present parasite antigens to *L. donovani* specific T-cells. This macrophage cell line was chosen because it has the same H-2 haplotype as the BALB/c mouse, which is a strain of mouse moderately susceptible to *L. donovani* infection and selected to conduct the in vivo experiments. Using a proportion of 3–5 parasites per cell and an initial incubation at room temperature for 4–6 hours follows by 37° C. for 24–48 hours, close to 90% of the macrophages were infected. The level of MHC class II molecule expression, as determined by FACS analysis, indicated that infection did not cause an effect on the levels of MHC class II expression when compared to non-infected control cells.

To test the ability of the *L. donovani*-infected P388D1 cells to present parasite antigens, macrophages were infected as indicated above and incubated at 26° C. for 6 hours, and then as 37° C. for either 24, 48 or 72 hours. At each of these time points the non-adherent cells and free parasites were washed out and the adherent cells were mechanically dislodged, washed and fixed with paraformaldehyde. These cells were then used as antigen presenting cells (APCs) for purified lymph node T-cells from BALB/c mice immunized with *L. donovani* promastigotes. To generate these anti-*L. donovani* specific T-cells, BALB/c mice (H-$2^d$) of both sexes (The Jackson Laboratory, Bar Harbor, Me.) were immunized at 8 to 14 weeks of age in the rear foot pad with 5–10×$10^6$ *L. donovani* promastigotes emulsified in complete Freünd's adjuvant (CFA) (Difco Laboratories, Madison, Mich.) as described in Rodrigues et al., *Parasite Immunol* 14:49 (1992). The draining lymph nodes were excised 8 days after the immunization and T-cells were purified in an anti-mouse Ig column to remove the B cells, as described in Bunn-Moreno and Campos-Neto, *J. Immunol.* 127:427 (1981), followed by a passage through a Sephadex G10 column to remove the macrophages.

Stimulation index was calculated by dividing the cpm obtained for the cells cultured in the presence of infected P388D1 macrophages by the cpm obtained for the cells cultured in the presence of non-infected macrophages, but subjected to the same conditions as the infected macrophages. The results shown in FIG. 1 indicate that *L. donovani*-infected P388D1 macrophage process parasite antigens and that optimal presentation occurs after 48 hours of infection. No stimulation of the T-cells by the non-infected macrophages was observed.

To isolate the MHC class II associated *L. donovani* peptides, P388D1 macrophages were infected with *L. donovani* promastigotes for an initial incubation of 6 hours at room temperature. The cultures were then transferred to 37° C. for the remainder of the 48 hour incubation period. At a ratio of 3–5 parasites per macrophage nearly 90% of the macrophages were infected after 24 hours of incubation at 37° C.

The MHC class II molecules were then affinity-purified. Approximately 1.5×$10^{10}$ *L. donovani*-infected or an equal number of non-infected P388D1 macrophages were used for each purification. The cells were harvested, washed with PBS and incubated for 30 minutes in cold lysis buffer (PBS, 1% Nonidet P40, 25 mM iodoacetamide, 0.04% sodium azide, 1 mM aprotinin and 1 mM PMSF). The insoluble material was removed by centrifugation at 40,000 g for 1 hour and the supernatant was recycled overnight at 4° C. over a 5 ml anti-MHC class II molecules (H-$2^d$) Sepharose column (Protein G Sepharose column to which the monoclonal antibody MK-D6 has been bound). Culture supernatants of MK-D6 hybridoma cells (American Type Culture Collection, Rockville, Md.) were employed as the source for anti-MHC class II (H-$2^d$) monoclonal antibody. The column was washed with 50 ml of lysis buffer and then with 50 ml of PBS containing 0.5% octyl glucopyranoside detergent. Bound molecules were eluted from the column with 1M acetic acid in 0.2% NaCl. The MHC/peptide molecules were separated from the IgG (MK-D6 monoclonal antibody) using a Centricon 100 filter unit (Amicon Division, W. R. Grace & Co., Beverly, Mass.). The peptides were then dissociated from the class II molecules by the addition of acetic acid to 2.5M, followed by separation using a Centricon 10 filter unit. The resulting peptide preparation, present in the low molecular weight sample, was then dried using a speed vac concentrator (Savant Instrument Inc., Farmingdale, N.Y.).

The peptides were redissolved in 200 μl of 0.05% TFA and separated by reverse-phase high performance liquid chromatography (RP-HPLC) using a 2.1 mm×25 cm Vydac C-18 column at a flow rate of 0.15 ml/min employing a 1 to 30% acetonitrile gradient (60 min) followed by a 30 to 60% gradient (30 min) and then a 60 to 80% gradient (90–110 min). Non-infected P388D1 cells were similarly processed to serve as background control for endogenous MHC class II associated peptides. FIG. 2 shows a representative experiment; four distinct peaks which are present only in the material isolated from infected macrophages (panel B), and not in the material isolated from uninfected macrophages (panel A) are indicated.

Out of three independent peptide extractions, twenty five distinct HPLC peptide peaks were isolated from *L. donovani*-infected macrophages and were subjected to protein sequence analysis using automated Edman degradation on an Applied Biosystems 477 gas-phase protein sequencer. Protein sequence and amino acid analysis were perfomed by the W. M. Keck Foundation, Biotechnology Resource Laboratory, Yale University, New Haven, Conn. In practically all determinations, no assignment could be made for the first position. Also, in most cases the definition of the amino acid residues of the 10–15 positions was based on the quantitative dominance of one residue over others. Using this approach, the sequences obtained for several peptides showed the presence of 3–6 different residues in many of the 10–15 sequence cycles analyzed for each determination, reflecting a mixture of peptides. In addition, sequences could not be obtained for some peaks because the peptides were blocked. Notwithstanding, three peptides sequences were determined. Amino-acid sequences were searched for identity with proteins in the GenBank database using the GENPETP, PIR and SWISSPROT programs. The sequence data base analysis revealed that one of the peptides was highly homologous to glyceraldehyde-3-phosphate dehydrogenase of various species. Another peptide had homology with elongation factor of several species, including Leishmania. The third sequence was not clearly related to any known proteins, and is shown below:

XQXPQ(L/K)VFDEXX SEQ ID NO:11.

B. Cloning and Sequencing of the Ldp23 Gene

In order to retrieve the *L. donovani* protein that was processed into a peptide associated with the MHC class II molecules of infected macrophages, the peptide sequence of uncertain origin was chosen to guide the strategy for cloning the corresponding parasite gene. A DNA fragment was initially amplified from *L. donovani* promastigote cDNA by PCR. The sense primer was a peptide derived oligonucleotide (5'>GGAATTCCCCInCAGCTInGTInTTCGAC<3') SEQ ID NO:12 containing an EcoRI restriction endonuclease site (underlined). The bases were selected following the preferential codon usage of *L. donovani*, as described in Langford et al., *Exp. Parasitol.* 74:360 (1992). Inosine was used for the residues of positions 4, 6 and 7 because of the low codon usage assurance for the corresponding amino acids. In addition, the carboxyl-terminal L-glutamic acid was not included for the design of the primer. The antisense primer was a poly-thymidine oligonucleotide (oligo dT, downstream primer) containing a XhoI restriction endonuclease site.

The gene fragment was amplified from a *L. donovani* promastigote cDNA preparation using the following reaction conditions: one cycle of 3 min at 94° C. immediately followed by 35 cycles of 1 min at 94° C., 1 min at 45° C. and I min at 72° C. The *L. donovani* cDNA was prepared from $5 \times 10^7$ washed promastigote forms harvested at the log growth phase (3 days culture). The cDNA was obtained using an Invitrogen cDNA cycle™ kit (Invitrogen Co., San Diego, Calif.). Oligonucleotide primers were synthesized by the DNA Synthesis Laboratory, Department of Pathology, Yale University School of Medicine.

The PCR products were analyzed by gel electrophoresis. Only one band of approximately 300 bp was obtained. This fragment was cloned and its sequence confirmed the sequence of the peptide-based primer including the glutamic acid codon, deliberately not included in the primer sequence.

The PCR amplified gene fragment was ligated into the pCR™ vector using the TA cloning system (Invitrogen Co., San Diego, Calif.). Transformants were selected in LB medium containing 100 µg/ml ampicillin and the plasmid DNA was isolated using the Wizard™ Minipreps DNA purification kit (Promega Co., Madison, Wis.). Insert DNA was released with the restriction enzymes EcoRI and XhoI (New England Biolabs, Beverly, Mass.), purified from an agarose gel electrophoresis and labeled with $^{32}$P using a random priming method (Megaprime Labeling Kit, Amersham Life Science, Buckinghamshire, England).

This DNA fragment was used as probe to screen a *L. donovani* promastigote cDNA library as described in Skeiky et al., *Infect. Immun.* 62:1643 (1994). An approximately 650 bp cDNA (Ldp23) was excised from the phagemid by in vivo excision using the Stratagene protocol. DNA sequencing was performed using the Sequenase version 2 system (DNA sequencing kit) in the presence or absence of 7-deaza-GTP (United States Biochemical, Cleveland, Ohio). The sequence is provided as SEQ ID NO:3, and shows complete homology with the original 300 bp PCR fragment. A 525 bp open reading frame containing an ATG codon that follows the last 4 bases of the spliced leader sequence and 3 stop codons adjacent to the poly A tail was identified. This frame also codes the carboxyl terminal sequence (KVFDE) SEQ ID NO:13 of the purified MHC class II associated peptide. The sequence analysis of the deduced protein sequence revealed one potential glycosylation site (Asn-Cys-Ser) at positions 68–70.

Sequence analysis was performed using the University of Wisconsin Genetics Computer Group Programs and the GenBank and EMBL data bases of protein and DNA sequences. The search for homology of the Ldp23 gene with known sequences revealed no significant homology.

C. Bacterial Expression and Purification of Recombinant Protein

The recombinant *L. donovani* peptide donor protein was produced in *E. coli* transformed with the pGEX 2T expression vector in which the Ldp23 gene was subcloned in frame. PCR was used to subclone the cloned gene in frame into the expression vector pGEX 2T. Primers containing the appropriate restriction site enzymes, initiation and termination codons were: 5'>GGATCCATGGTCAAGTCCCA CTACATCTGC<3' SEQ ID NO:14 for the upstream primer and 5'>GAATTCAGACCGGATAGAAA TAAGCCAAT-GAAA<3' SEQ ID NO:15 for the downstream primer (restriction sites of BamHI and EcoRI are underlined respectively). PCR conditions were as indicated above for the amplification of the original peptide related DNA fragment. The template used was pBluescript plasmid containing the cloned gene from the cDNA library.

Overexpression of the recombinant fusion protein was accomplished by growing the transformed *E. coli* (DH5α) and inducing the tac promoter with 1 mM isopropyl-β-thiogalactopyranoside (IPTG) (Stratagene, La Jolla, Calif.). Cells were collected, centrifuged, and analyzed for the presence of the fusion protein by SDS-PAGE. A glutathione-S-transferase fusion protein of 43–44 kD was produced, indicating a leishmanial protein of approximately 18 kD, as glutathione-S-transferase (GST) has a MW of 26 kD. However, the fusion protein was very insoluble and therefore could not be purified by affinity chromatography using a glutathione column. The use of low concentrations of detergents like SDS, sarcosyl, deoxycolate, and octyl-glucopyranoside during the extraction steps was efficient to solubilize the protein but unfortunately prevented its binding to the glutathione column. Other maneuvers, such as the growth of the *E. coli* and incubation and induction of the tac promoter with IPTG at 33° C., did not improve the protein solubility. However, the purification was achieved by preparative SDS-PAGE. The band was visualized with 0.1M KCl, cut and electroeluted from the gel followed by extensive dialysis against PBS and concentration on Centricon 10 filters.

Figure 3:
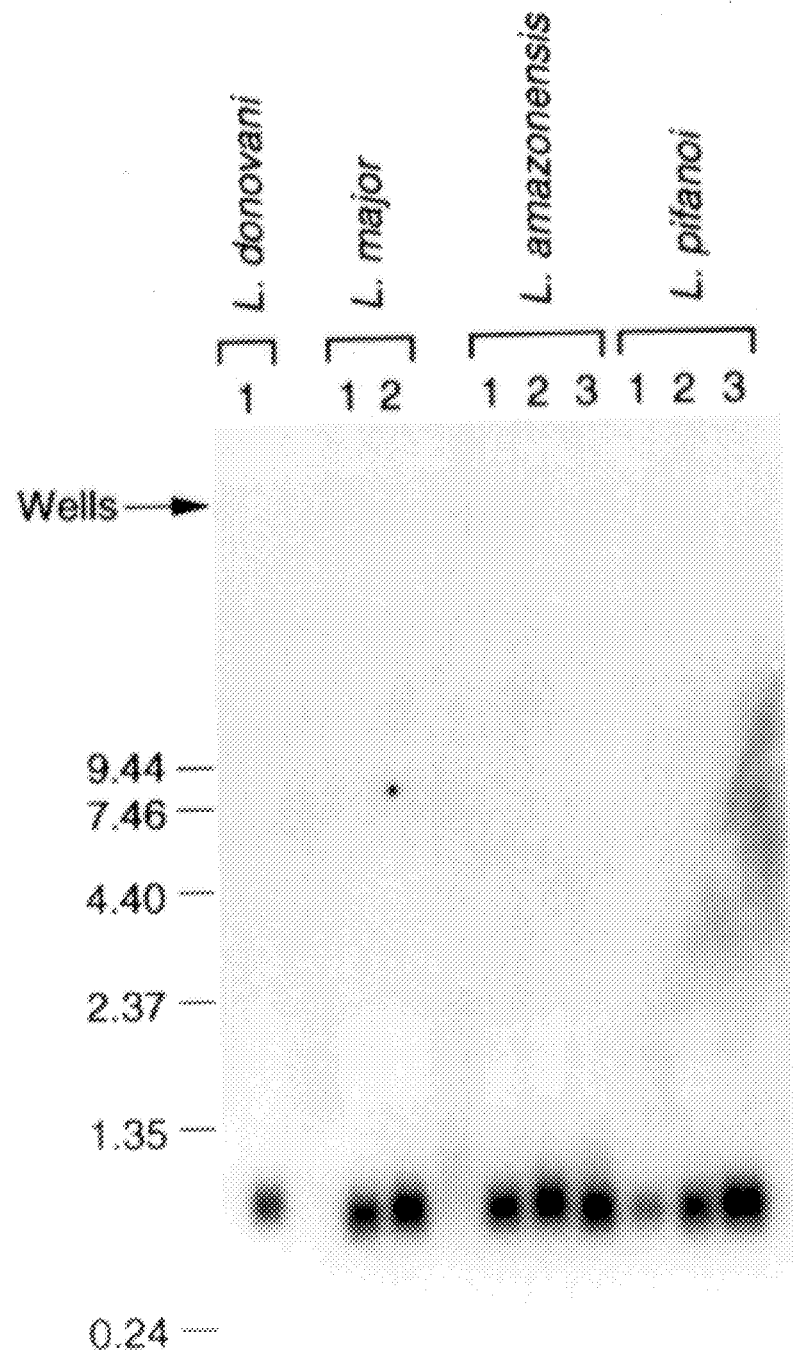
FIG. 3 illustrates the expression and purification of Ldp23 as a recombinant fusion protein. Panel A shows a Coomassie blue-stained SDS-PAGE gel of lysed E. coli without (lane 1) and with (lane 2) IPTG induction of Ldp23 expression. Arrow indicates the recombinant fusion protein. Panel B shows the fusion protein following excision from a preparative SDS-PAGE gel, electroelution, dialysis against PBS and analytical SDS-PAGE.

Approximately 500 µg of purified protein was obtained. The purified protein is shown in FIG. 3. In panel A, *E. coli* (DH5α) transformed with the expression vector pGEX 2T containing the Ldp23 gene was grown in LB medium and the tac promoter was induced with IPTG for 3 hours. The cells were pelleted, resuspended in loading buffer and submitted to SDS-PAGE (10%) under reducing condition. The gel was stained with Coomassie blue. Lane 1 shows the uninduced E. coli and land 2 shows the induced E coli. The arrow indicates the recombinant protein. Panel B shows the protein prepared as in panel A and submitted to a preparative SDS-PAGE. The band corresponding to the overexpressed recombinant fusion protein was identified by KCl, cut out, electroeluted from the gel strip, dialyzed against PBS and submitted to analytical SDS-PAGE (12%). Numbers on the left side indicate the molecular weights of the markers. Attempts to further purify the leishmanial protein by cleaving it out from the fusion protein GST with thrombin were unsuccessful.

D. Expression of Ldp23

To ascertain that the Ldp23 peptide is expressed in Leishmania organisms, a Northern blot analysis was performed using RNA prepared from different promastigote growth phases (logarithmic and stationary) and from the amastigote form of these parasites.

The RNA was prepared from $2\times10^7$ parasite cells using the Micro RNA isolation kit (Stratagene, La Jolla, Calif.) according to the company's recommended instructions. RNA was prepared from L. donovani promastigotes (logarithmic growth phase); from L. major promastigotes (logarithmic and stationary growth phases); from L. amazonesis, both promastigotes (logarithmic and stationary growth phases) and amastigotes purified from CBA/J infected mice; and from L. pifanoi, both promastigotes (logarithmic and stationary growth phases) and amastigotes (from axenic culture medium). L. donovani (1S strain), L. amazonensis (MHOM/BR/77/LTB0016), L. major (MHOM/IR/79/LRC-L251) and L. pifanoi (MHOM/VE/60/Ltrod) promastigotes were grown and maintained at 26° C. in Schneider's medium containing 20% FCS and 50 µg/ml gentamicin. The amastigote forms of L. amazonensis were obtained by differential centrifugation of a "pus-like" foot pad lesion of a CBA/J mouse infected for 6 months with this parasite. L. pifanoi amastigotes were obtained from axenic culture as previously reported by Pan et al., J. Eik. Microbiol. 40:213 (1993).

The hybridization was carried out at 45° C. in the presence of 50% formamide, 5× Denhardt's solution, 0.1% SDS, 100 µg/ml single stranded salmon sperm DNA and 5× SSPE using 0.45 µm Nytran membrane filters (Schleicher & Schuell, Keene, N.H.). The probe was the $^{32}$P labeled Ldp23 gene.

FIG. 4 shows that one single RNA band of 680 bp was observed for all growth phases and forms of all tested Leishmania. Within FIG. 4, the numbers 1, 2 and 3 refer to RNA obtained from promastigotes at the logarithmic growth phase, promastigotes at the stationary growth phase and amastigote forms, respectively, and the numbers on the left side indicate the molecular weights of the markers in base pairs. This result is consistent with the corresponding gene size (525 bp) and with the molecular weight of the expressed protein and points to the ubiquitous distribution and expression of this gene within the genus Leishmania.

E. Induction of Anti-L. donovani Antibody Response in Mice and Rabbits by Purified Recombinant Protein In order to evaluate the immunogenicity of the recombinant leishmanial protein, and to investigate its expression in the parasites, mice and rabbits were immunized with the GST-fusion protein in CFA. BALB/c mice were immunized in the rear foot pad with 5–10 µg of protein emulsified in CFA. Protein concentration was determined using the Bio-Rad Protein Assay reagent (Bio-Rad Laboratories, Richmond, Calif.). The mice were boosted 7 days later with 5–10 µg of protein emulsified in incomplete Freund's adjuvant (IFA) inoculated into the peritoneal cavity. The mice were bled 7 days after the second immunization. New Zealand white rabbits (Millbrook Farm, Amherst, Mass.) were immunized according to the following protocol: one intra-muscular (IM) injection of 25–30 µg of purified recombinant protein emulsified in CFA into each thigh on day one; one IM injection of 25–30 µg of purified protein emulsified in IFA into each shoulder on day 7; on day 15, 25–30 µg of the purified protein in PBS was injected into the subcutaneous tissue. The rabbit was bled 7 days after the last immunization.

Sera were prepared and the anti-Leishmania antibody response was measured by Western blot analysis and by FACScan. In both cases L. donovani promastigotes were used as antigen. Approximately $2\times10^6$ L. donovani promastigotes were grown in Schneider's medium for 3 days (log phase), were washed with PBS, lysed with SDS-PAGE loading buffer and submitted to electrophoresis under reducing conditions using a 15% polyacrylamide gel. The proteins were transferred onto 0.45 µp Immobilon-P transfer membrane (Millipore Co., Bedford, Mass.) using a wet-type electroblotter (Mini Trans-Blot Electrophoretic Transfer Cell, Bio Rad Life Science Division, Richmond, Calif.) for 2 hours at 50 V. The membranes were blocked overnight at room temperature with PBS containing 3% normal goat serum (NGS), 0.2% Tween-20 and 0.05% sodium azide, followed by 3 washes with PBS. The blots were then incubated for 3–4 hours at 4° C. with a 1/200 dilution of pre-immune rabbit serum (lane A, FIG. 5) or with the same dilution of anti-fusion protein rabbit antiserum (lane B, FIG. 5). The sera was previously absorbed 2× with non-viable desiccated Mycobacterium tuberculosis H-37 RA (Difco Laboratories, Detroit, Mich.) and were diluted in PBS containing 1% NGS and 5% powdered non-fat bovine milk (Carnation, Nestlé Food Company, Glendale, Calif.). The membranes were then washed with PBS, incubated for 1 hour at room temperature with goat anti-rabbit IgG antibody conjugated with alkaline phosphatase (Promega, Madison, Wis.), washed once with PBS and 2× with veronal buffer pH 9.4. The reaction was visualized using the substrate mixture 5-bromo-4-chloro-3-indoyl-phosphate and nitroblue tetrazolium (Kirkegaard & Perry Laboratories Inc., Gaithersburg, Md.) according to the manufacturer's instructions.

Figure 5:
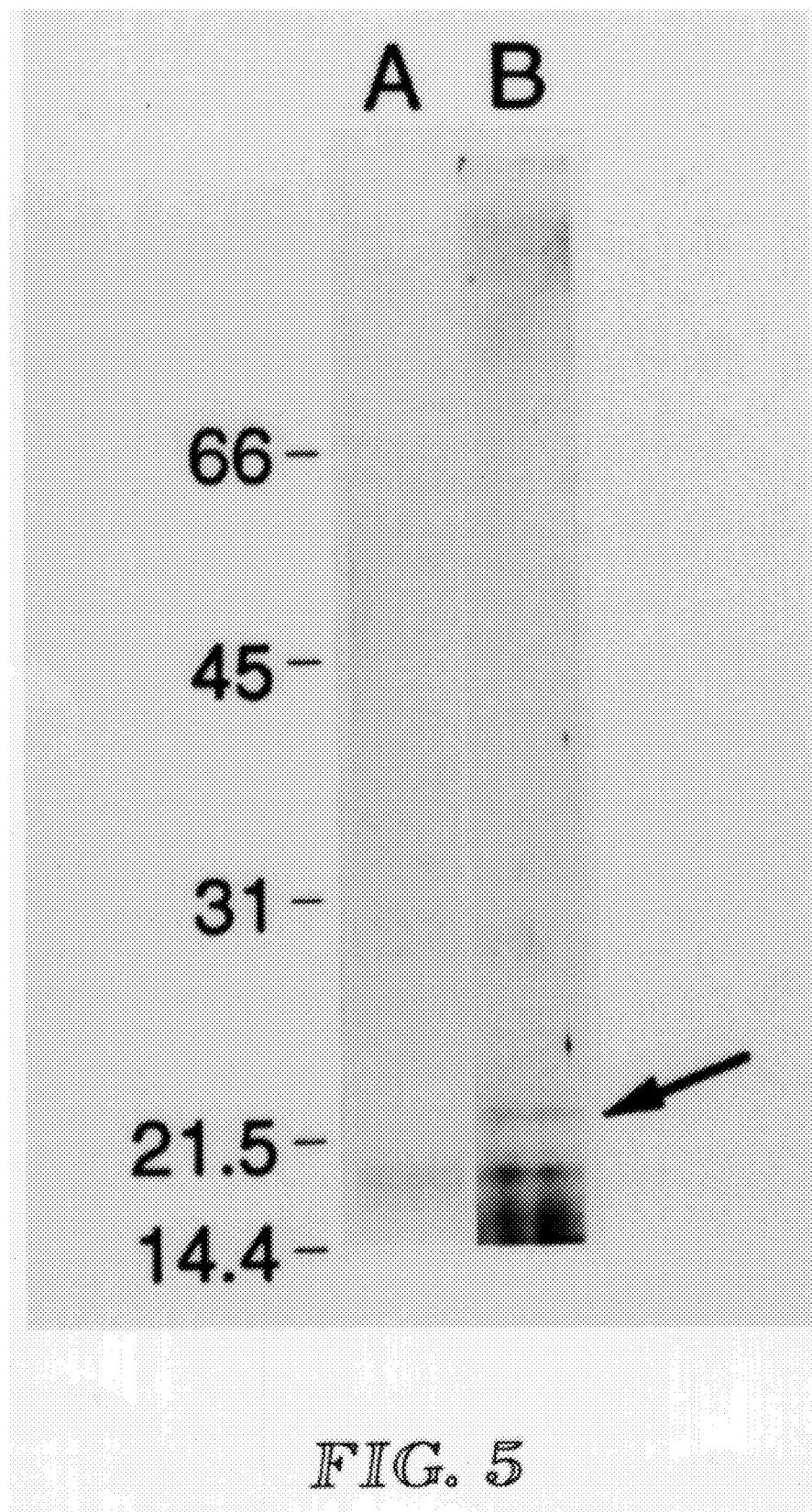
FIG. 5 shows a Western blot analysis of L. donovani promastigote antigens incubated with pre-immune rabbit serum (lane A) or with anti-Ldp23 rabbit antiserum (lane B).
Figure 6:
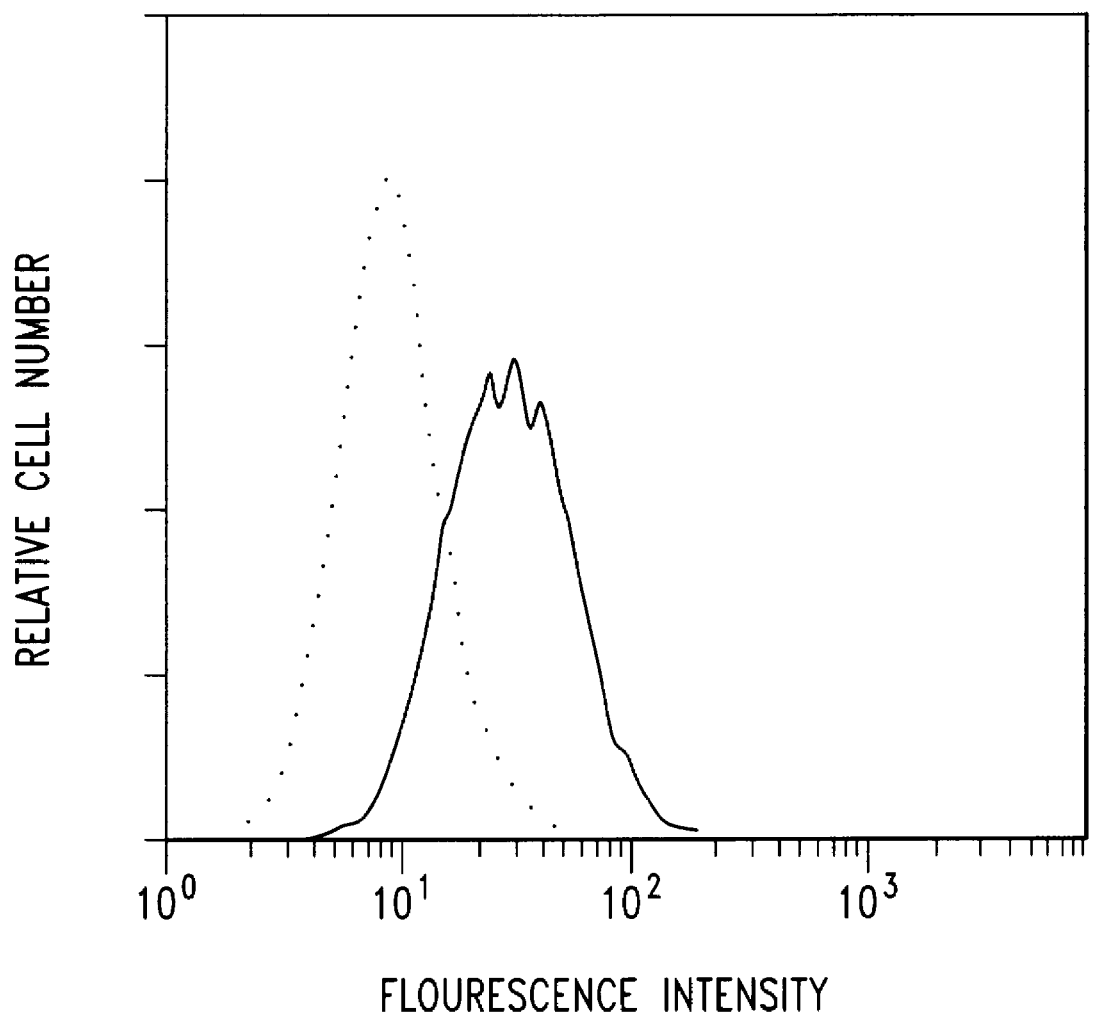
FIG. 6 illustrates the surface expression of Ldp23 on live L. donovani promastigotes. The dotted line shows the indirect immunofluorescence performed using pre-immune mouse serum and the solid line shows the result obtained with mouse anti-GST-Ldp23 antiserum. Fluorescence intensity was analyzed by FACScan.

FIG. 5 shows that the rabbit anti-recombinant protein antiserum detects a single protein of 23 kDa (Ldp23) in the Leishmania crude extract antigen preparation. No bands were observed when an anti-GST antiserum was used (not shown). Moreover, the FACScan analysis (FIG. 6) shows that the antibody induced by the recombinant Ldp23 reacts with intact live L. donovani promastigotes, thus pointing to a cell surface expression of this molecule on these organisms. The dotted line in FIG. 6 shows the indirect immunofluorescence performed using pre-immune mouse serum and the solid line in FIG. 6 shows the result obtained with mouse anti-GST-Ldp23 antiserum. Both sera were diluted at 1/100. Parasites were washed with staining buffer and incubated with FITC conjugated goat anti-mouse immunoglobulin antibody. Fluorescence intensity was analyzed by FACScan.

F. Recognition of Recombinant Ldp23 by Leishmania-Specific Lymph Node T-cells

Figure 7:
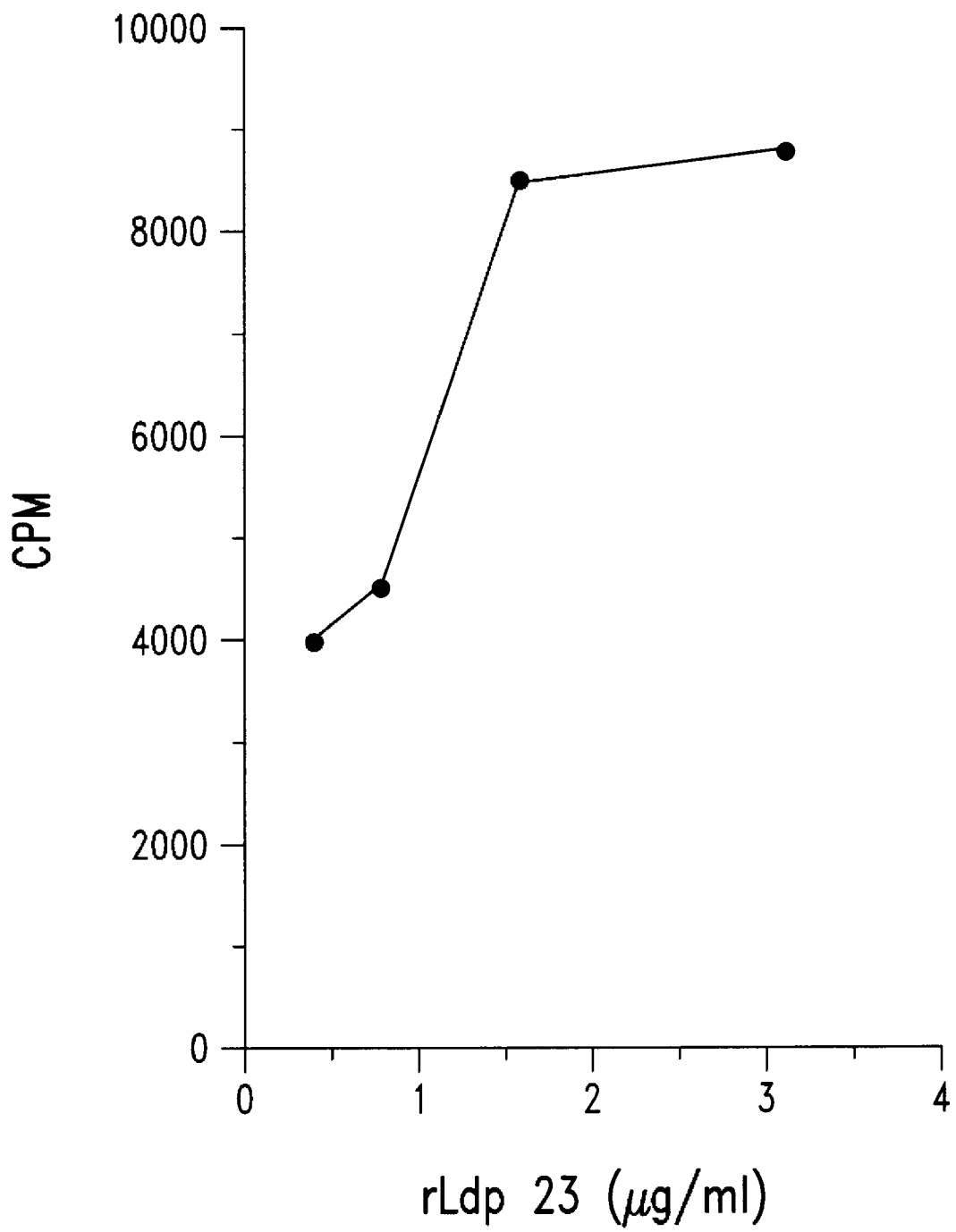
FIG. 7 shows the stimulation of Leishmania-specific T-cell proliferation by Ldp23. The results are presented as relative cell number as a function of fluorescence intensity. T-cells ($10^5$/well) were purified from lymph nodes of BALB/c mice immunized in the foot pad with L. donovani promastigotes in CFA and were cultured with various concentrations of the purified recombinant Ldp23 in the presence of $2\times10^5$ Mitomycin C-treated normal BALB/c spleen mononuclear cells. Proliferation of T-cells was measured at 27 hours of culture. Values are expressed as cpm and represent the mean of [$^3$H]TdR incorporation of triplicate cultures.

To test the responsiveness of T-cells to the Ldp23 protein, two sets of experiments were performed. In the first experiment, lymph node T-cells ($10^5$/well) from BALB/c mice immunized with L. donovani promastigotes (as described above) were stimulated to proliferate with $2\times10^5$ Mitomycin C-treated normal mononuclear spleen cells (APC) and pulsed with the purified recombinant fusion protein. Proliferation of T-cells was measured at 72 hours of culture. Values are expressed in FIG. 7 as cpm and represent the mean of [³H]TdR incorporation of triplicate cultures. Background cpm of cells (T cells+APC) cultured in the presence of medium alone was 1291. FIG. 7 shows that Leishmania specific T-cells proliferate well and in a dose response manner to recombinant Ldp23. No response was observed when purified GST was added instead of the recombinant fusion protein nor when lymph node T-cells from mice immunized with CFA alone were stimulated to proliferate in the presence of the Leishmanial fusion protein (not shown).

The recognition of the recombinant Ldp23 protein by Leishmania-specific T-cells was also tested using two murine models of leishmaniasis, the L. major highly susceptible BALB/c mice and the L. anazonensis susceptible CBA/J mice as described in Champsi and McMahon-Pratt, Infect. Immun. 56:3272 (1988). These models were selected to investigate the cytokine pattern induced by Ldp23. In the mouse model of leishmaniasis, resistance is associated with Th 1 cytokines while susceptibility is linked to Th 2 responses.

Lymph node cells were obtained 3 weeks after the initiation of infection of BALB/c mice with L. major and the ability of these cells to recognize the recombinant Ldp23 was measured by proliferation and by the production of the cytokines IFN-γ and IL-4. $2 \times 10^6$ cells obtained from the draining popliteal lymph node of infected mice were cultured for 72 hours in the presence of recombinant Ldp23 or Leishmania lysate. The levels of IFN-γ and IL-4 in culture supernatants were measured by ELISA as previously described (Chatelain et al., J. Immunol. 148:1172 (1992), Curry et al., J. Immunol. Meth. 104:137 (1987), and Mossman and Fong, J. Immunol. Meth. 116:151 (1989)) using specific anti IFN-γ and IL-4 monoclonal antibodies (PharMingen, San Diego, Calif.).

Figure 8B:
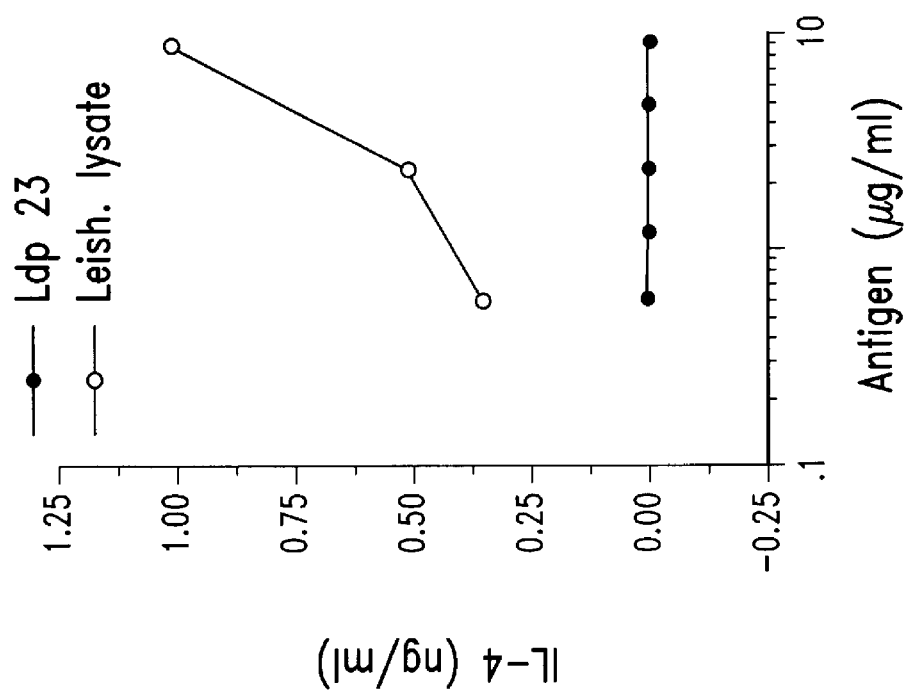
FIG. 8 illustrates the Ldp23-induced cytokine production by lymph node cells of BALB/c mice. Cultures were incubated with varying amounts of Ldp23 or Leishmania lysate, presented as μg/mL, and were assayed by ELISA for the production of interferon-γ (panel A) or interleukin-4 (panel B), both of which are shown as ng/mL.
Figure 8A:
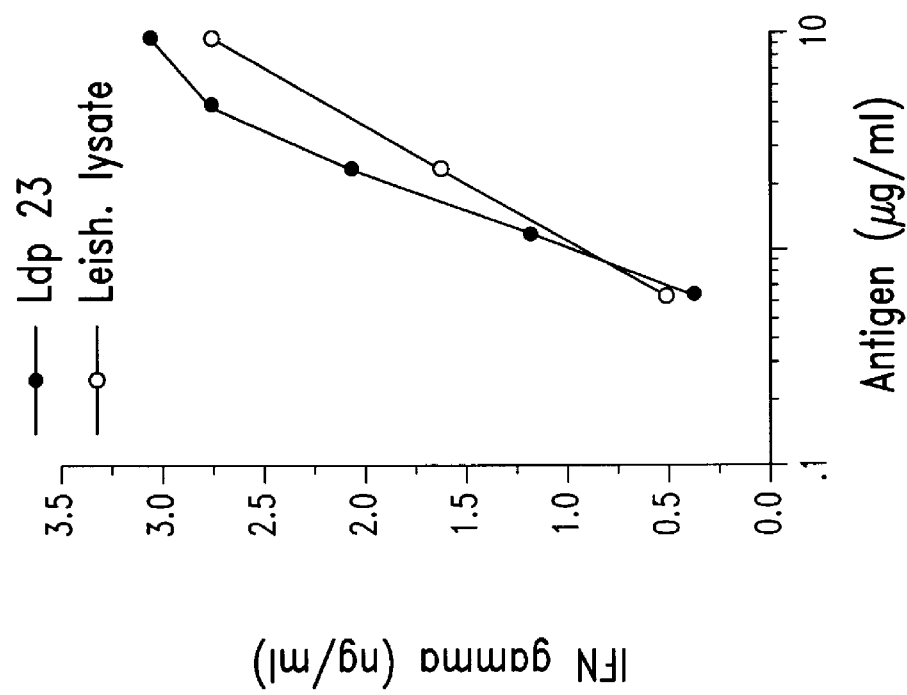

Ldp23 did stimulate these cells to proliferate (not shown) and induced a typical Th 1 type of cytokine response as indicated by the production of high levels of IFN-γ (panel A of FIG. 8) and no IL-4 (panel B of FIG. 8). Stimulation of these cells with a Leishmania crude lysate yielded a mixed Th cytokine profile. Exactly the same pattern of cytokine production was obtained from the CBA/J mice infected with L. amazonensis (not shown). These results clearly indicate that Ldp23 is a powerful and selective activator of the Th 1 cytokines response in mouse cells.

Example 3

Preparation of Hsp83

This Example illustrates the preparation of a Leishmania antigen Hsp83, having the sequence provided in SEQ ID NO:6.

A genomic expression library was constructed with sheared DNA from L. braziliesis (MHOM/BR/75/M2903) in bacteriophage λZAP II (Stratagene, La Jolla, Calif.). The expression library was screened with Escherichia coil preadsorbed serum from an L. braziliesis-infected individual with ML. Immunoreactive plaques were purified, and the pBSK (−) phagemid was excised by protocols suggested by the manufacturer. Nested deletions were performed with exonuclease III to generate overlapping deletions for single-stranded template preparations and sequencing. Single-stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems automated sequencer model 373A.

Recombinant antigens produced by these clones were purified from 500 ml of isopropyl-β-D-thiogalactopyranoside (IPTG)-induced cultures as described in Skeiky et al., J. Exp. Med. 176:201–211 (1992). These antigens were then assayed for the ability to stimulate PBMC from Leishmania-infected individuals to proliferate and secrete cytokine. Peripheral blood was obtained from individuals living in an area (Corte de Pedra, Bahia, Brazil) where L. braziliensis is endemic and where epidemiological, clinical, and immunological studies have been performed for over a decade, and PBMC were isolated from whole blood by density centrifugation through Ficoll (Winthrop Laboratories, New York, N.Y.). For in vitro proliferation assays, $2 \times 10^5$ to $4 \times 10^5$ cells per well were cultured in complete medium (RPMI 1640 supplemented with gentainicin, 2-mercaptoethanol, L-glutamine, and 10% screened pooled A+ human serum; Trimar, Hollywood, Calif.) in 96-well flat-bottom plates with or without 10 μg of the indicated antigens per ml or 5 μg of phytohemagglutinin per ml (Sigma Immunochemicals, St. Louis, Mo.) for 5 days. The cells were then pulsed with 1 μCi of [³H]thymidine for the final 18 h of culture. For determination of cytokine production 0.5 to 1 ml of PBMC was cultured at $1 \times 10^6$ to $2 \times 10^6$ cells per ml with or without the Leishmania antigens for 48 and 72 h.

The supernatants and cells were harvested and analyzed for secreted cytokine or cytokine mRNAs. Aliquots of the supernatants were assayed for gamma interferon (IFN-γ), tumor necrosis factor alpha (TNF-α), interleukin-4 (IL-4), and IL-10 as described in Skeiky et al., J. Exp. Med. 181:1527–1537 (1995). For cytokine mRNA PCR analysis, total RNA was isolated from PBMC and cDNA was synthesized by using poly(dT) (Pharmacia, Piscataway, N.J.) and avian mycloblastosis virus reverse transcriptase. Following normalization to β-actin, diluted cDNA was amplified by PCR using Taq polymerase (Perkin-Elmer Cetus, Foster City, Calif.) with 0.2 μM concentrations of the respective 5' and 3' external primers in a reaction volume of 50 μl. The nucleotide sequences of the primary pairs and the PCR conditions used were as described in Skeiky et al., J. Exp. Med. 181:1527–1537 (1995). We verified that our PCR conditions were within the semiquantitative range by initially performing serial dilutions of the cDNAs and varying the number of cycles used for PCR. Plasmids containing the human sequences for IL-2, IFN-γ, IL-4, IL-10, and β-actin were digested, and the DNA inserts were purified after separation on 1% agarose gels. Radiolabeled ³²P probes were prepared by the random priming method. PCR products were analyzed by electrophoresis on 1.5% agarose gels, transferred to nylon membranes, and probed with the appropriate ³²P-labeled DNA insert.

A recombinant clone was identified in the above assays which, following sequence comparison of its predicted amino acid sequence with sequences of other proteins, was identified as a Leishmania braziliensishomolog of the eukaryotic 83 kD heat shock protein (Lbhsp83). The sequence of the clone is provided in SEQ ID NO:5 and the deduced protein sequence is provided in SEQ ID NO:6. On the basis of the homology, this clone, designated Lbhsp83a, appears to lack the first 47 residues of the full length 703 amino acid residues. Lbhsp83 has an overall homology of 94% (91% identity and 3% conservative substitution), 91% (84% identity and 7% conservative substitution) and 77% (61% identity and 16% conservative substitution) with L. amazonensis hsp83, T. cruzi hsp83 and human hsp89, respectively. A second clone (designated Lbhsp83b), which contained the 43 kD C-terminal portion of hsp83 (residues 331 to 703) was also isolated. FIG. 19 presents a comparison of the Lbhsp83 sequence with *L. amazonensis* hsp83 (Lahsp83), *T. cruzi* hsp83 (Tchsp83) and human hsp89 (Huhsp89).

The results of proliferation assays using Lbhsp83a are shown in Table 1. Cells from all mucosal leishmaniasis (ML) patients proliferated strongly in response to Lbhsp83a, with stimulation indices (SIs) ranging from 19 to 558 (as compared to 20 to 1,634 for parasite lysate). Proliferation of PBMC from cutaneous leishmaniasis (CL) patients was variable and except for levels in two patients (IV and VII), levels were significantly lower than those of ML patients. By comparison, the proliferative responses of individuals with self-healing CL to Lbhsp83a were similar to those of individuals with ML. However, the responses of all six self-healing individuals to Lbhsp83 were consistently higher than those to Lbhsp83b. This suggests that PBMC from self-healing CL patients preferentially recognize one or more T-cell epitopes located within the amino portion of Lbhsp83.

TABLE 1

In vitro Proliferation of PMBC from *L. braziliensis*-infected Individuals in Response to Lbhsp83

| Group and Patient | Mean [$^3$H]thymidine incorporation [$10^3$ cpm (SD)], SI with: | | |
|---|---|---|---|
| | Lysate | Lbhsp83a | Lbhsp83b |
| ML | | | |
| I | 41.3, (1.3), 294 | 32.5, (6.6), 221 | 46.7, (1.4), 318 |
| II | 44.2, (0.5), 104 | 20, (3.7), 47 | 36.7, (0.76), 86 |
| III | 27.4, (1.5), 150 | 8.1, (1.7), 44 | 9.9, (0.32), 54 |
| IV | 52.7, (3.3), 138 | 54.1, (6.2), 142 | 32.0, (1.3), 84 |
| V | 140.6, (7.6), 308 | 151.8, (57), 333 | 150.4, (7.9), 331 |
| VI | 15.8, (1.8), 20 | 21.3, (4.4), 28 | 14.4, (1.3), 19 |
| VII | 300.1, (9.4), 1634 | 102.1, (7.6), 558 | 41.7, (4.9), 228 |
| CL | | | |
| I | 0.26, (0.0), 1.5 | 0.57, (0.3), 3.3 | 0.43, (0.17), 3.3 |
| II | 55.63, (8.6), 218 | 0.42, (0.0), 1.6 | 0.8, (0.14), 3.2 |
| III | 0.39, (0.5), 4.0 | 3.4, (0.5), 9 | 2.6, (0.9), 6.6 |
| IV | 19.14, (1.3), 87 | 7.17, (0.6), 32 | 5.9, (0.9), 27 |
| V | 0.32, (0.2), 3.0 | 1.47, (0.5), 14 | 0.3, (0.1), 3.0 |
| VI | 0.77, (0.1), 4.7 | 1.44, (0.2), 9 | 1.3, (0.6), 8.0 |
| VII | 4.01, (1.0), 2.0 | 60.3, (8.5), 15 | 66.7, (3.9), 16.6 |
| Self-healing CL | | | |
| I | 19.7, (4.4), 94 | 61.3, (4.6), 293 | 5.0, (2.0), 24 |
| II | 0.6, (0.1), 6.5 | 7.0, (2.0), 79 | 1.2, (0.8), 13 |
| III | 59.6, (7.1), 519 | 49.4, (3.1), 429 | 21.4, (3.7), 186 |
| IV | 0.2, (0.1), 1.6 | 13.1, (1.7), 108 | 0.6, (0.1), 5 |
| V | 27.1, (2.0), 225 | 6.3, (2.6), 52 | 3.0, (1.5), 25 |
| VI | 130.3, (14), 340 | 28.2, (2.9), 74 | 7.7, (3.8), 20 |
| Control (uninfected) | | | |
| I | 0.19, (0.0), 1.4 | 0.18, (0.0), 1.3 | 0.40, (0.16), 2.8 |
| II | 0.31, (0.1), 1.7 | 0.19, (0.0), 1.0 | 0.27, (0.0), 1.5 |
| III | 0.44, (0.2), 4.1 | 0.48, (0.1), 5.0 | 0.51, (0.2), 5.2 |
| IV | 0.4, (0.1), 3.2 | 0.52, (0.2), 5.1 | 0.50, (0.1), 5.0 |

Figures 4A, 4B:
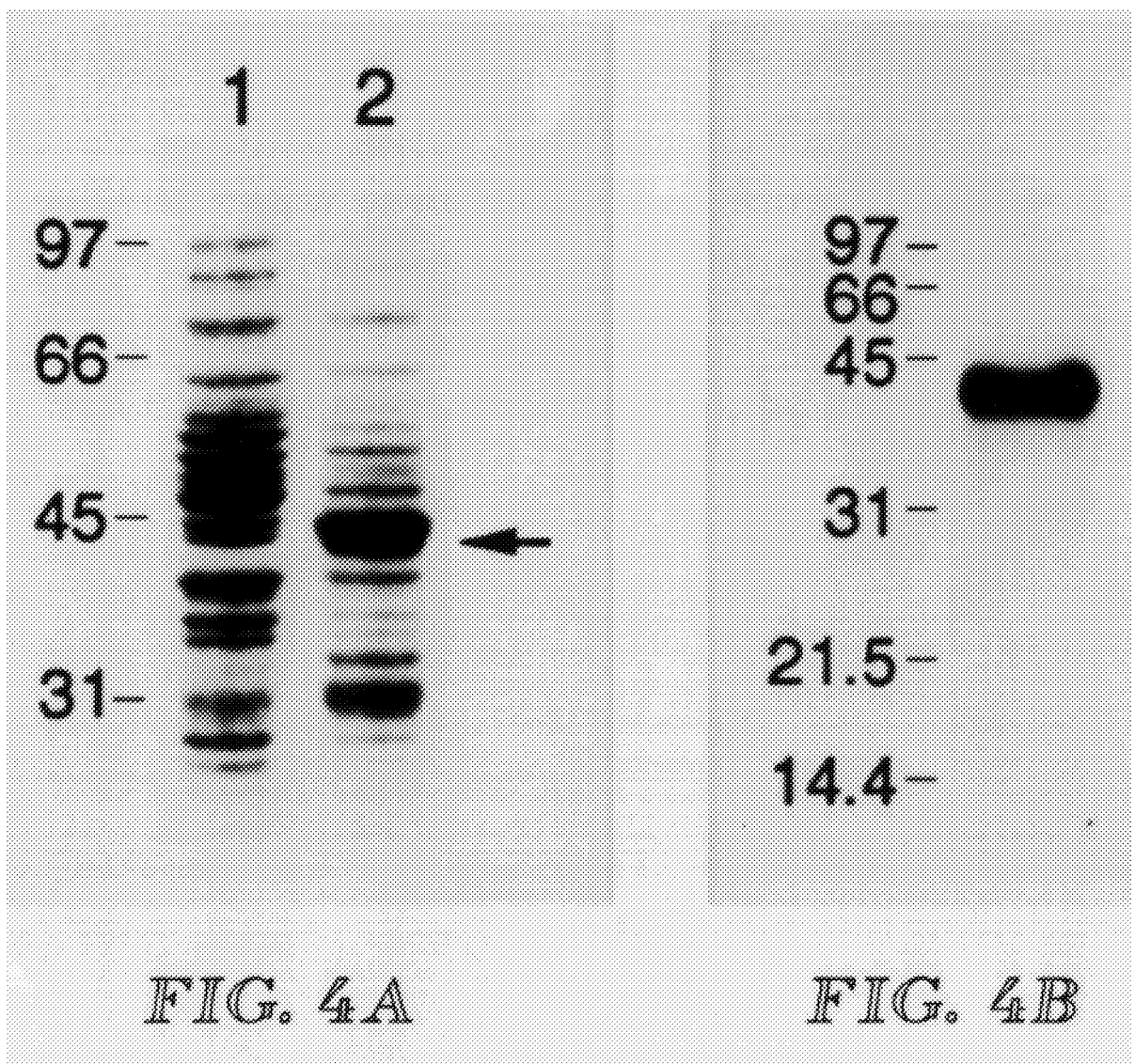
FIG. 4 presents a Northern blot analysis of total RNA prepared from L. donovani, L. major, L. amazonensis and L. pifanoi with a $^{32}p$ labeled Ldp23 gene. 1, 2 and 3 refer to RNA obtained from promastigotes at the logarithmic growth phase, promastigotes at the stationary growth phase and amastigote forms, respectively.
Figure 9A:
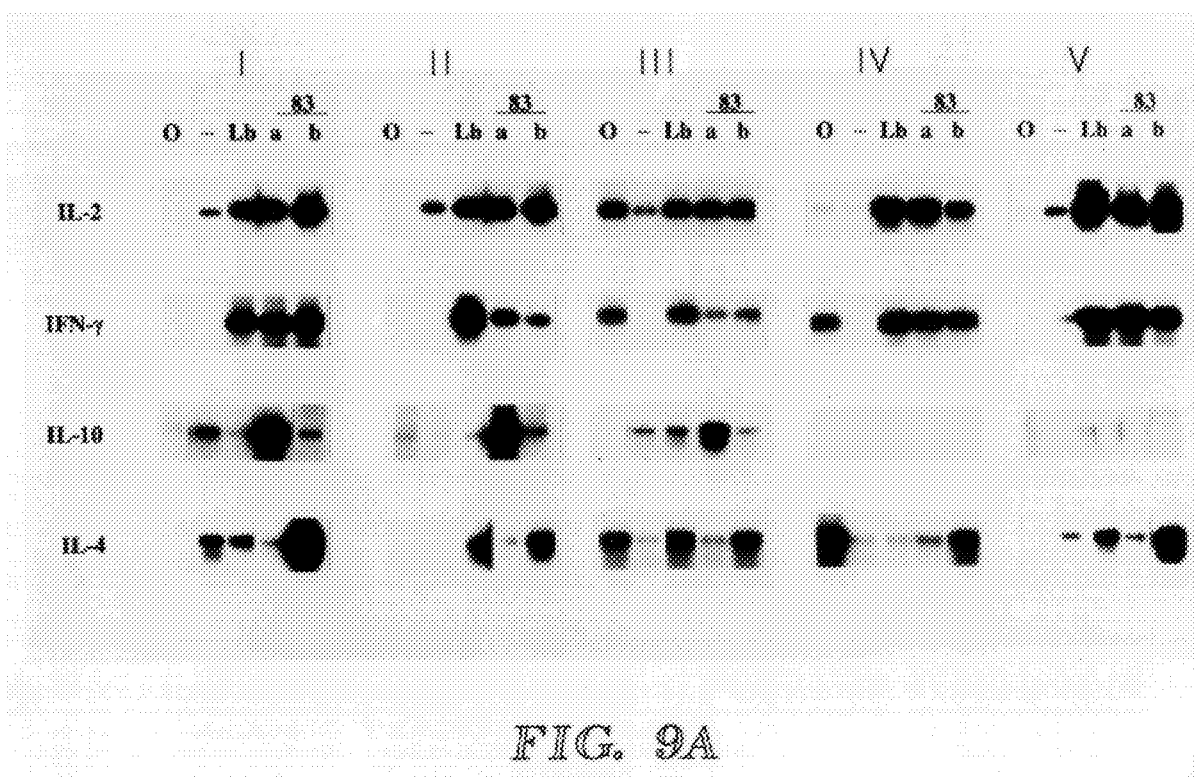
FIG. 9 shows the PCR amplification of cytokine mRNAs isolated from ML (Panel A) and CL (panel B) patient PBMC before and after stimulation with representative polypeptides of the present invention. Lanes O and—indicate the level of PCR products at the initiation of culture and after 72 hours of culture, respectively, in the absence of added polypeptide; lanes Lb, 83a and 83b indicate the level of PCR products following culturing of PBMC with L. braziliensis lysate, Lbhsp83a and Lbhsp83b, respectively.
Figure 9B:
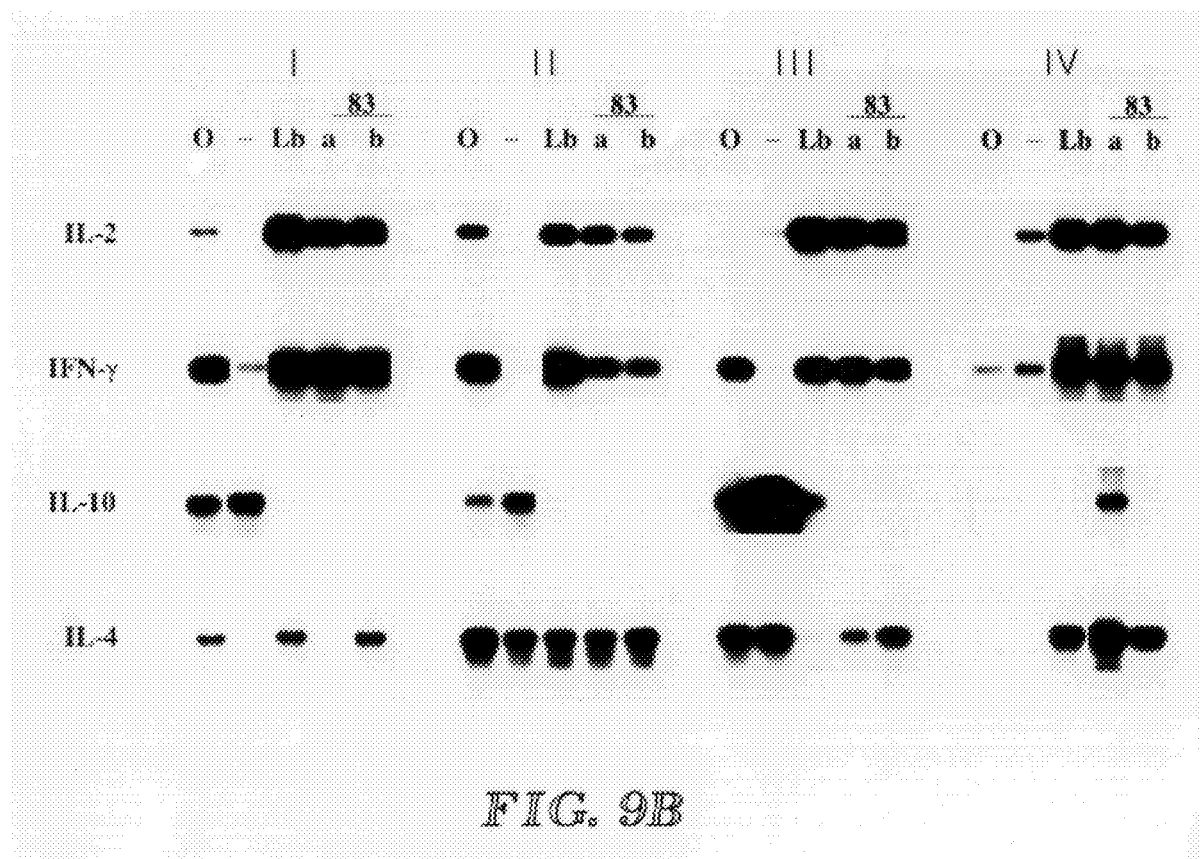

A more detailed analysis of cytokine patterns of PBMC from ML patients was performed by reverse transcriptase PCR. Cytokine mRNAs were evaluated in cells prior to culturing (FIG. 9, lanes O) or following culturing in the absence (lanes–) or presence of the indicated antigen for 48 and 72 h. FIG. 4A shows the results for five of the six ML patients whose PBMC were analyzed. In about half of the ML patients, noncultured (resting) PBMC had detectable levels of mRNA for IFN-γ, IL-2, and IL-4 but not IL-10. CL patient PBMC, however, had IL-10 mRNA in the resting state in addition to mRNAs for the other cytokines tested (FIG. 4B). Following in vitro culture without antigen, the levels of mRNA for IFN-γ, IL-2, and IL-4 in resting cells from ML patients decreased to background levels while IL-10 mRNA levels increased. In contrast, PBMC of most CL patients had stable or increased IL-10 mRNA, while the mRNAs for IL-2, IFN-γ, and IL-4 were reduced to barely detectable levels in the absence of antigen stimulation.

In PBMC of three ML patients, stimulation with lysate resulted in increased expression of mRNA for IFN-γ, IL-2, and IL-4 but not IL-10. By comparison, both Lbhsp83 polypeptides elicited the production of mRNA for IFN-γ and IL-2 from all ML patient PBMC tested. In contrast, profiles of mRNA for IL-10 and IL-4 differed for the two hsp83 polypeptides. Lbhsp83a stimulated the production of IL-10 but not IL-4 mRNA (patients I, II, III, and IV), while Lbhsp83b stimulated the production of IL-4 but not IL-10 mRNA in all six patients.

All CL patients tested responded to both Lbhsp83 polypeptides as well as to the parasite lysate by upregulating the synthesis of mRNAs for IL-2 and IFN-γ, and in two of four patients (I and IV), the level of IL-4 mRNA also increased, indicating stimulation of both Th1 and Th2 cytokines. Interestingly and as in the case of ML patient uncultured PBMC which did not have detectable levels of IL-10 mRNA, Lbhsp83a and not Lbhsp83b stimulated PBMC from one CL patient (IV) to synthesize IL-10 mRNA. However, in the other three patients (I, II, and III) with resting levels of IL-10 mRNA, both rLbhsp83 polypeptides as well as the parasite lysate downregulated the expression of IL-10 mRNA.

Figure 10A:
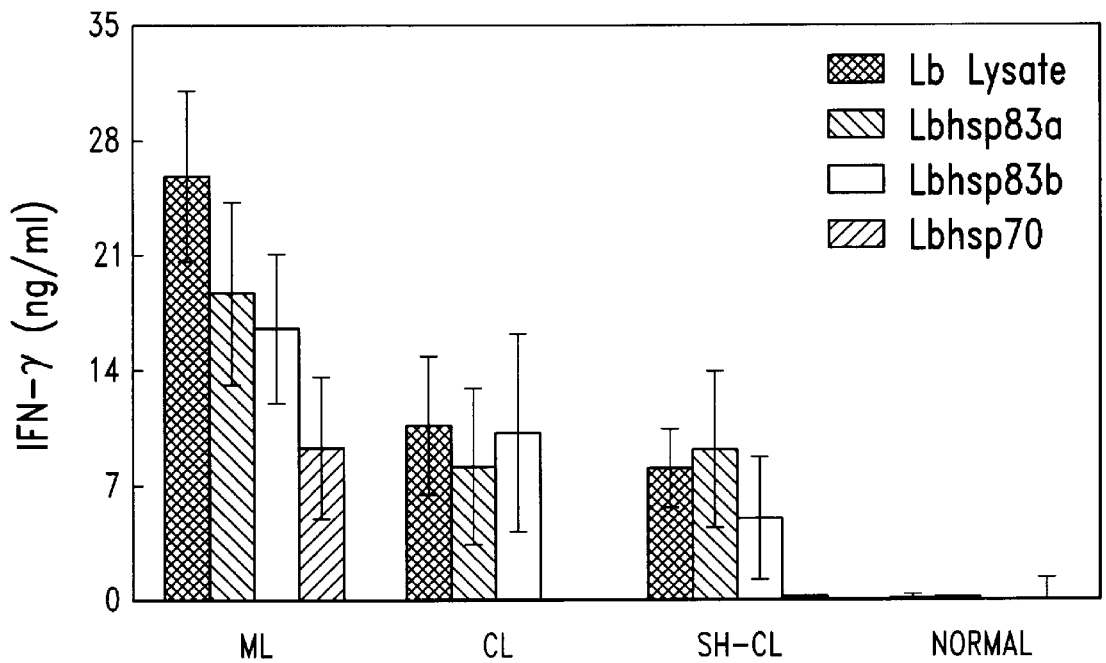
FIG. 10 presents a comparison of the levels of interferon-γ (panel A) and TNF-α (panel B) in the supernatants of 72 hour PBMC cultures from Leishmania-infected and control individuals in response to stimulation with parasite lysate or the indicated polypeptides.

PBMC supernatants were also assayed for the presence of secreted IFN-γ, TNF-α, IL-4, and IL-10. Cells from all ML and self-healing CL patients (seven and six patients, respectively) and from four of seven CL patients were analyzed for secreted IFN-γ following stimulation with both rLbhsp83 polypeptides, parasite lysate and Lbhsp70, an *L. braziliensis* protein homologous to the eukaryotic 70 kD heat shock protein (FIG. 10A). In general, rLbhsp83a stimulated patient PBMC to secrete higher levels of IFN-γ than did rLbhsp83b (0.2 to 36 and 0.13 to 28 ng/ml, respectively). The presence of secreted IFN-γ correlated well with the corresponding mRNA detected by PCR.

Figure 10B:
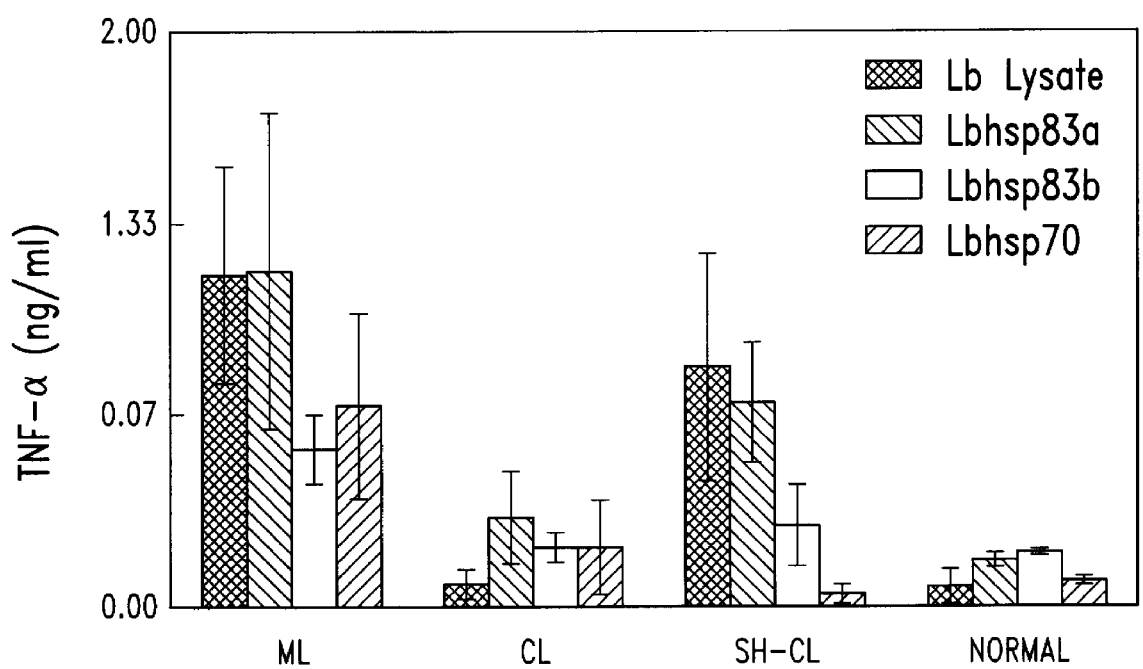

PBMC from four of five ML patients (I, II, V, and VII) had supernatant TNF-α levels (0.8 to 2.2 ng/ml) higher than those detected in cultures of PBMC from uninfected controls following stimulation with parasite lysate (FIG. 10B). Similarly, the same PBMC were stimulated by rLbhsp83 to produce levels of TNF-α in supernatant ranging from 0.61 to 2.9 ng/ml. Compared with those of uninfected controls, PBMC from three (I, V, and VI), five (I, II, IV, V, and VI), and two (II and V) of six individuals analyzed produced higher levels of TNF-α in response to parasite lysate, rLbhsp83a, and rLbhsp83b, respectively. The levels of TNF-α produced by PBMC from CL patients in response to parasite lysate were comparable to those produced by uninfected controls. However, rLbhsp83 stimulated TNF-α production in the PBMC of two of these patients. rLbhsp83a stimulated higher levels of TNF-α production than did rLbhsp83b. In the absence of antigen stimulation, only PBMC from ML patients (five of six) produced detectable levels of supernatant TNF-α (60 to 190 pg/ml).

Figure 11:
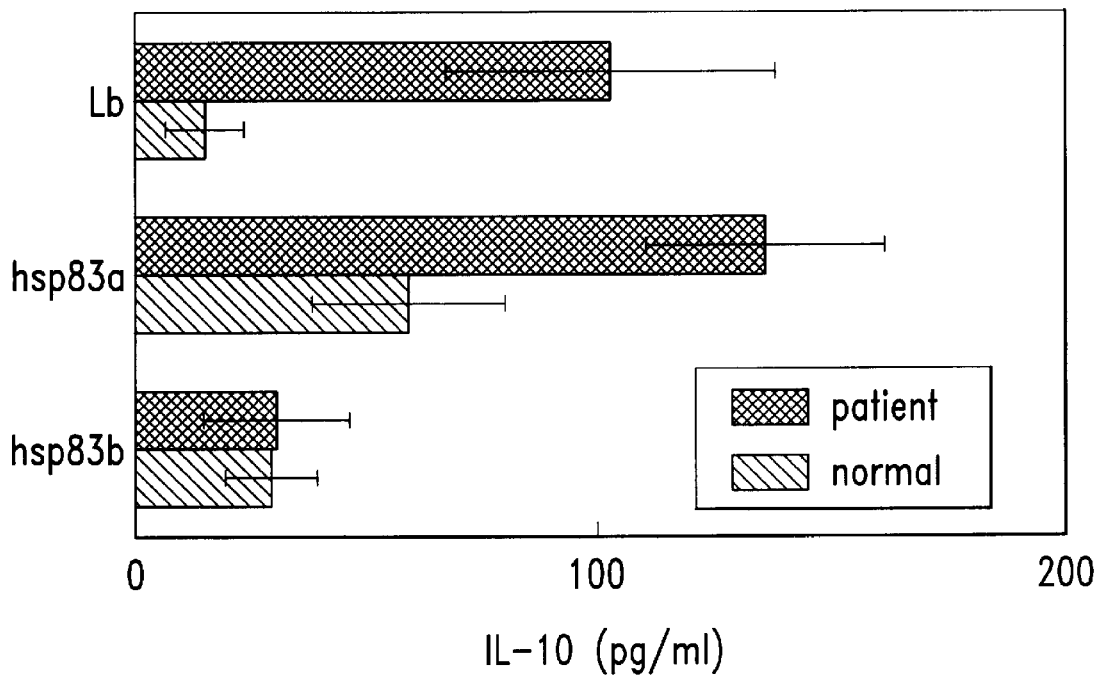
FIG. 11 illustrates the levels of IL-10 p40 (in pg/mL) in the supernatant of PBMC cultures from L. brazilienisis-infected individuals and uninfected controls 72 hours following stimulation with parasite promastigote lysate (Lb), Lbhsp83a or Lbhsp83b.

In agreement with the IL-10 mRNA, IL-10 was detected by ELISA in the antigen-stimulated PMBC culture supernatants from ML and CL patients. The levels (49 to 190 pg)

were significantly higher (up to 10-fold) following stimulation with rLbhsp83a compared with those after parallel stimulation of the same cells with rLbhsp83b (FIG. 11). Parasite lysate also stimulated PMBC from some of the patients to produce IL-10. Although rLbhsp83 stimulated PMBC from uninfected individuals to produce IL-10, with one exception, the levels were lower than those observed with patient PMBC. IL-4 was not detected in any of the supernatants analyzed. Therefore, the level of any secreted IL-4 is below the detection limit of the ELISA employed (50 pg/ml). Taken together, the results demonstrate that a predominant Th1-type cytokine profile is associated with PMBC from L. brazilieisis-infected individuals following stimulation with rLbhsp83 polypeptides.

Figure 12:
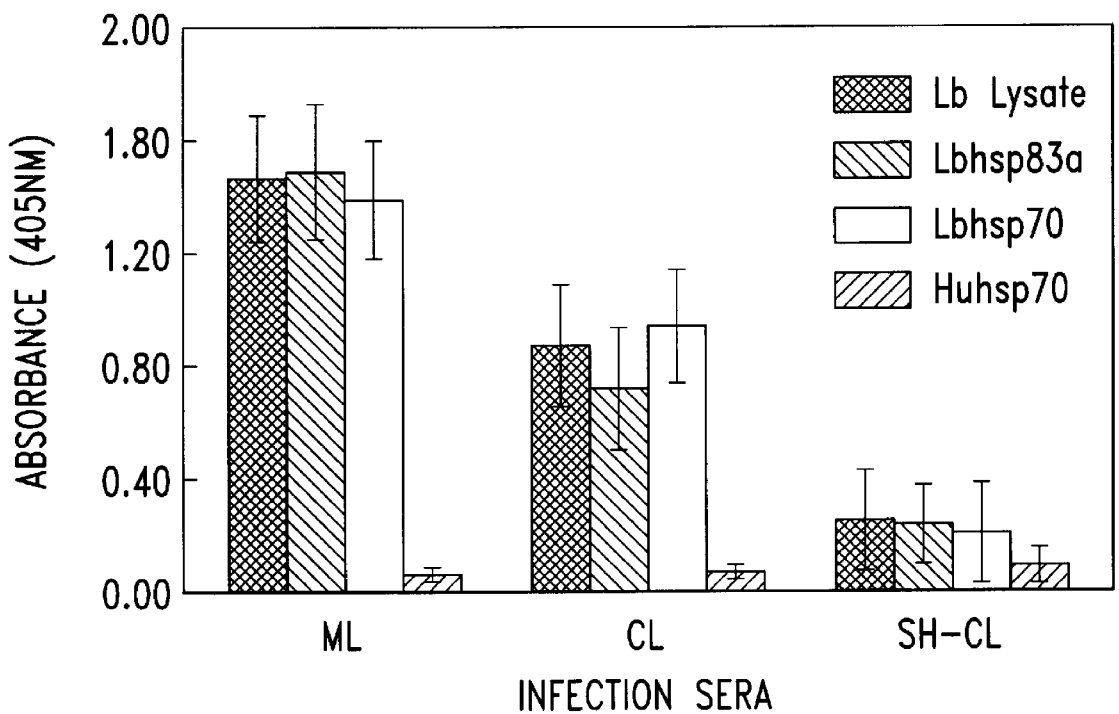
FIG. 12 presents the reactivities of L. braailiensis infection sera from patients with representative polypeptides of the present invention in a standard ELISA. Values are expressed as absorbance at 405 nm.

To determine the correlation between the observed T-cell responses and antibody production to Lbhsp83, we compared the antibody (immunoglobulin G) reactivities to Lbhsp83 in sera from the three patient groups (FIG. 12). The ELISA reactivities of ML patient sera with rLbhsp83a were comparable to those observed with parasite lysate, and in general, there was a direct correlation between ML patient anti-Lbhsp83 antibody titer and T-cell proliferation. Of 23 serum samples from ML patients analyzed, 22 were positive (~96%) with absorbance values of 0.20 to >3.0. Eleven of the ML patient serum samples had optical density values that were >1. In general, CL patients had significantly lower anti-Lbhsp83 antibody titers ($\bar{x}$=0.74; standard error of the mean [SEM]=0.1) compared to those of ML patients. Therefore, ML and CL patient anti-rhsp83 antibody titers correlated with their respective T-cell proliferative responses. Anti-rLbhsp83 antibody titers were significantly higher in patients with ML ($\bar{x}$=1.5; SEM=0.2) than in self-healing CL patients ($\bar{x}$=0.35; SEM=0.056), although their T-cell proliferative responses were similar. In fact, anti-Lbhsp83 antibody titers in serum from self-healing CL patients were comparable to those from uninfected controls ($\bar{x}$=0.24; SEM=0,028). By using 2 standard deviations greater than the mean absorbance value of uninfected control (0.484) as a criterion for positive reactivity to Lbhsp83, eight of nine of the self-healing patient serum samples tested were negative.

Example 4

Preparation of Clones Encoding Lt-210

This Example illustrates the preparation of clones encoding portions of the Leishmania antigen Lt-210, and which has the sequence provided in SEQ ID NO:8.

An expression library was constructed from L. tropica (MHOM/SA/91/WR1063C) genomic DNA. The DNA was isolated by solubilizing L. tropica promastigotes in 1 mM Tris-HCl, pH 8.3, 50 mM EDTA, 1% SDS and treating with 100 µg/ml RNaseA and 100 µg/ml proteinase K. The sample was then sequentially extracted with an equal volume of phenol, phenol: chloroform (1:1), and Chloroform. DNA was precipitated by adding 0.1 volume of 3M sodium acetate (pH 5.2) and 2.5 volume 95% ethanol. The precipitate was resuspended in 10 µM Tris, 1 mM EDTA. DNA was sheared by passage through a 30-gauge needle to a size range of 2–6 kilobase, and was repaired by incubation with DNA poll in the presence of 100 µM each dATP, dCTP, dGTP, and dTTP. EcoRi adapters were ligated to the DNA fragments. After removal of unligated adapters by passage over a G-25 Sephadex™ column, the fragments were inserted in Ec,oRI cut Lambda Zapll (Stratagene, La Jolla, Calif).

Approximately 43,000 pfu were plated and screened with sera isolated from viscerotropic leishmaniasis (VTL) patients. Sera from VTL patients were received from Drs. M. Grogl and A. Magill. The VTL patient group included eight individuals from whom parasites were isolated and cultured, seven of which had confirmed infection with L. tropica. Four other patients were culture negative, but were still considered to be infected based on either PCR analysis or a positive monoclonal antibody smear (Dr. Max Grogl, personal communication). Serum samples from the 11 infected patients were pooled and anti-E. coli reactivity removed by affinity chromatography (Sambrook et al., supra, p. 12.27–12.28). Lambda phage expressing reactive proteins were detected after antibody binding by protein A-horseradish peroxidase and ABTS substrate.

Three clones, Lt-1, Lt-2, and Lt-3, containing a portion of the Lt-210 gene were identified and purified. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, Gene 28:351–359, 1984). Single strand template was prepared and the sequence determined with Applied Biosystems Automated Sequencer model 373A or by Sanger dideoxy sequencing. The sequence on both strands of the coding portion of Lt-1 clone was determined. The partial sequence of one strand of Lt-2 clone was determined.

SEQ ID NO:7 presents the DNA sequence of Lt-1, and SEQ ID NO:8 provides the predicted amino acid sequence of the open reading frame. The DNA sequence of the coding portion of the Lt-1 clone includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies. The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely α-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same gene, Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Schleicher & Schuell, Keene, N.H.). Inserts from rLt-1 and rLt-2 were labeled with $^{32}$P-CTP by reverse transcriptase from random oligonucleotide primers and used as probes after separation from unincorporated nucleotides on a Sephadex G-50 column. Hybridizations using the rLt-1 or the rLt-2 probe are performed in 0.2M NaH$_2$PO$_4$/3.6M NaCl at 65° C., whereas hybridization using the rLt-1r probe is performed in 0.2M NaH$_2$PO$_4$/3.6M NaCl/0.2M EDTA at 60° C. overnight. Filters are washed in 0.075M NaCl/0.0075M sodium citrate pH 7.0 (0.15M NaCl/0.0150M sodium citrate for the Lt-1r probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy number. A similar, overlapping pattern was observed using either the Lt-1 or Lt-2 insert as a probe, consistent with the premise that these two clones contain sequences near or overlapping one another. In addition, sequences hybridizing with these clones are present in other Leishmania species.

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert described below was labeled and used as a probe. The seven different *L. tropica* isolates yielded similar intensities and restriction patterns, with only a single restriction fragment length polymorphism among the isolates. These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript SK⁻ phagemid from Lambda Zap II was performed according to the manufacturer's protocol. Phagemid virus particles were used to infect *E coli* XL-1 Blue. Production of protein was induced by the addition of IPTG. Protein was recovered by first lysing, pellets of induced bacteria in buffer (LB, 50 mM Tris-HCl, pH 8.0, 100 mM NaCl, 10 mM EDTA) using a combination of lysozyme (750 μg/mL) and sonication. rLt-1, rLt-2, and rLt-1r, were recovered from the inclusion bodies after solubilization in 8M urea (rLt-1 and rLt-2) or 4M urea (rLt-1r). Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

Example 5

Preparation of LbeIF4A

This example illustrates the molecular cloning of a DNA sequence encoding the *L. braziliensis ribosomal* antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E. coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T-cell assays for their ability to stimulate a proliferative and cytokine production, as described in Examples 7 and 8 below.

A recombinant clone was identified in the above assays which, following sequence comparison of its predicted amino acid sequence with sequences of other proteins, was identified as a Leishmania braziliensishomolog of the eukaryotic initiation factor 4A (eIF4A). The isolated clone (pLeIF. 1) lacked the first 48 amino acid residues (144 nucleotides) of the full length protein sequence. The pLeIF. 1 insert was subsequently used to isolate the full length genomic sequence.

SEQ ID NO:7 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 6

Preparation of Soluble Leishmania Antigens

This Example illustrates the preparation of soluble Leishmania antigens from an *L. major* culture supernatant. *L. major* promastigotes are grown to late log phase in complex medium with serum until the reach a density of 2–3×10$^7$ viable organisms per mL of medium. The organisms are thoroughly washed to remove medium components and resuspended at 2–3×10$^7$ viable organisms per mL of defined serum-free medium consisting of equal parts RPMI 1640 and medium 199, both from Gibco BRL, Gaithersburg, M.D. After 8–12 hours, the supernatant is removed, concentrated 10 fold and dialyzed against phosphate-buffered saline for 24 hours. Protein concentration is then determined and the presence of at least eight different antigens confirmed by SDS-PAGE. This mixture is referred to herein as "soluble Leishmania antigens."

Example 7

Comparison of Interleukin-4 and Interferon-γ Production Stimulated by Leishmania Antigens This Example illustrates the immunogenic properties of the antigens prepared according to Examples 1, 2, 5 and 6, as determined by their ability to stimulate IL-4 and IFN-γ in lymph node cultures from infected mice and in human PBMC preparations. Lymph node cultures for use in these studies were prepared from *L. major*-infected BALB/c mice 10 days after infection, as described in Example 2. PBMC were prepared using peripheral blood obtained from individuals with cured *L. donovani* infections who were immunologically responsive to Leishmania. Diagnosis of the patients was made by clinical findings associated with at least one of the following: isolation of parasite from lesions, a positive skin test with Leishmania lysate or a positive serological test. Uninfected individuals were identified based on a lack of clinical signs or symptoms, a lack of history of exposure or travel to endemic areas, and the absence of a serological or cellular response to Leishmania antigens. Peripheral blood was collected and PBMC isolated by density centrifugation through Ficoll™ (Winthrop Laboratories, New York).

Culture supernatants were assayed for the levels of secreted IL-4 and IFN-γ. IFN-γ was quantitated by a double sandwich ELISA using mouse anti-human IFN-γ mAb (Chemicon, Temucula, Calif.) and polyclonal rabbit anti-human IFN-γ serum. Human rIFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml.

Figure 13A:
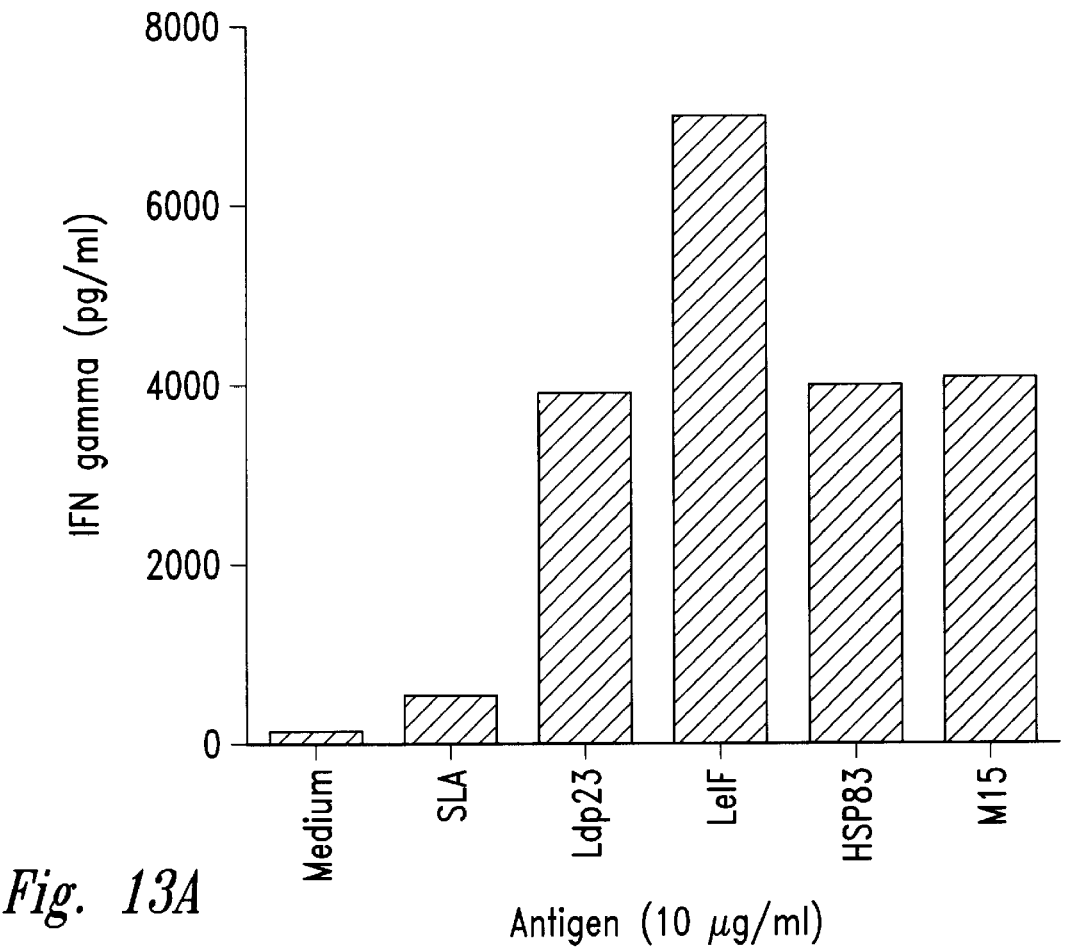
FIGS. 13A and 13B, illustrates the level of secreted IL-4 and IFN-γ (in pg/mL) stimulated in mouse lymph node cultures by the addition of representative polypeptides of the present invention.
Figure 13B:
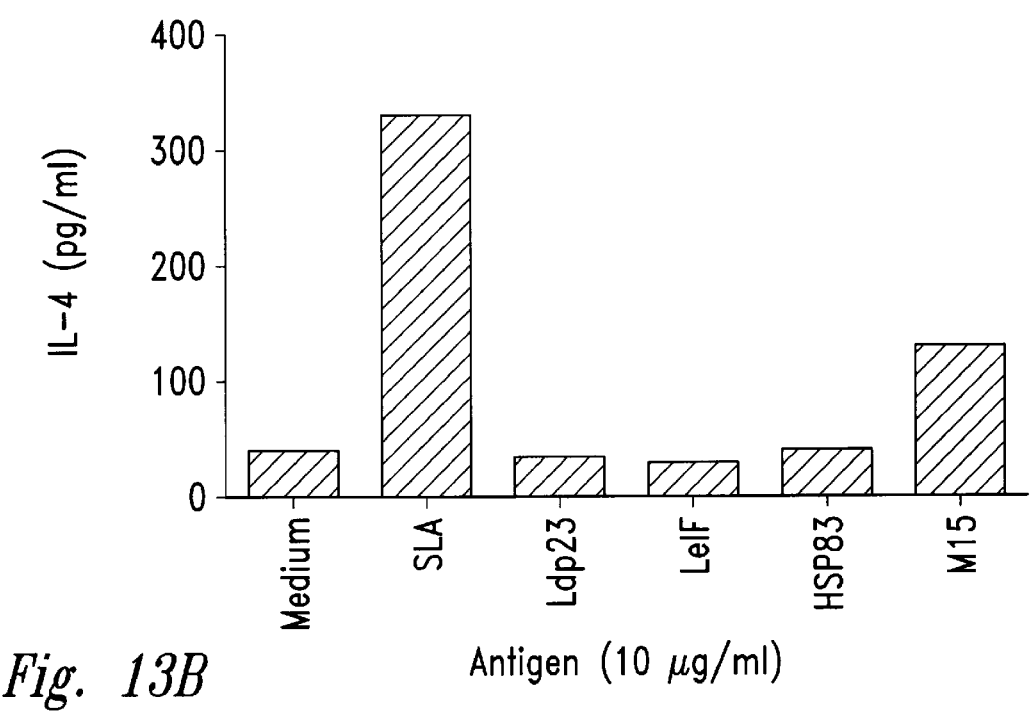

FIGS. 13A and 13B, illustrate the mean level of secreted IL-4 and IFN-γ, respectively, 72 hours after addition of 10 μg/mL of each of the following antigens to a lymph node culture prepared as described above: soluble Leishmania antigen (i.e., an extract prepared from ruptured promastigotes which contains membrane and internal antigens (SLA)), Ldp23, LbeIF4A (LeIF), Lbhsp83, M15 and LmeIF (the *L. major* homolog of LbeIF4A). The levels of secreted IL-4 and IFN-γ in medium alone (i.e., unstimulated) are also shown. While SLA elicits a predominantly Th2 response from lymph node cells of Leishmania-infected mice, Ldp23, LbeIF4A, Lbhsp83 and M15 elicited relatively little IL-4 and large amounts of IFN-γ, consistent with a Th1 response profile.

Figure 14:
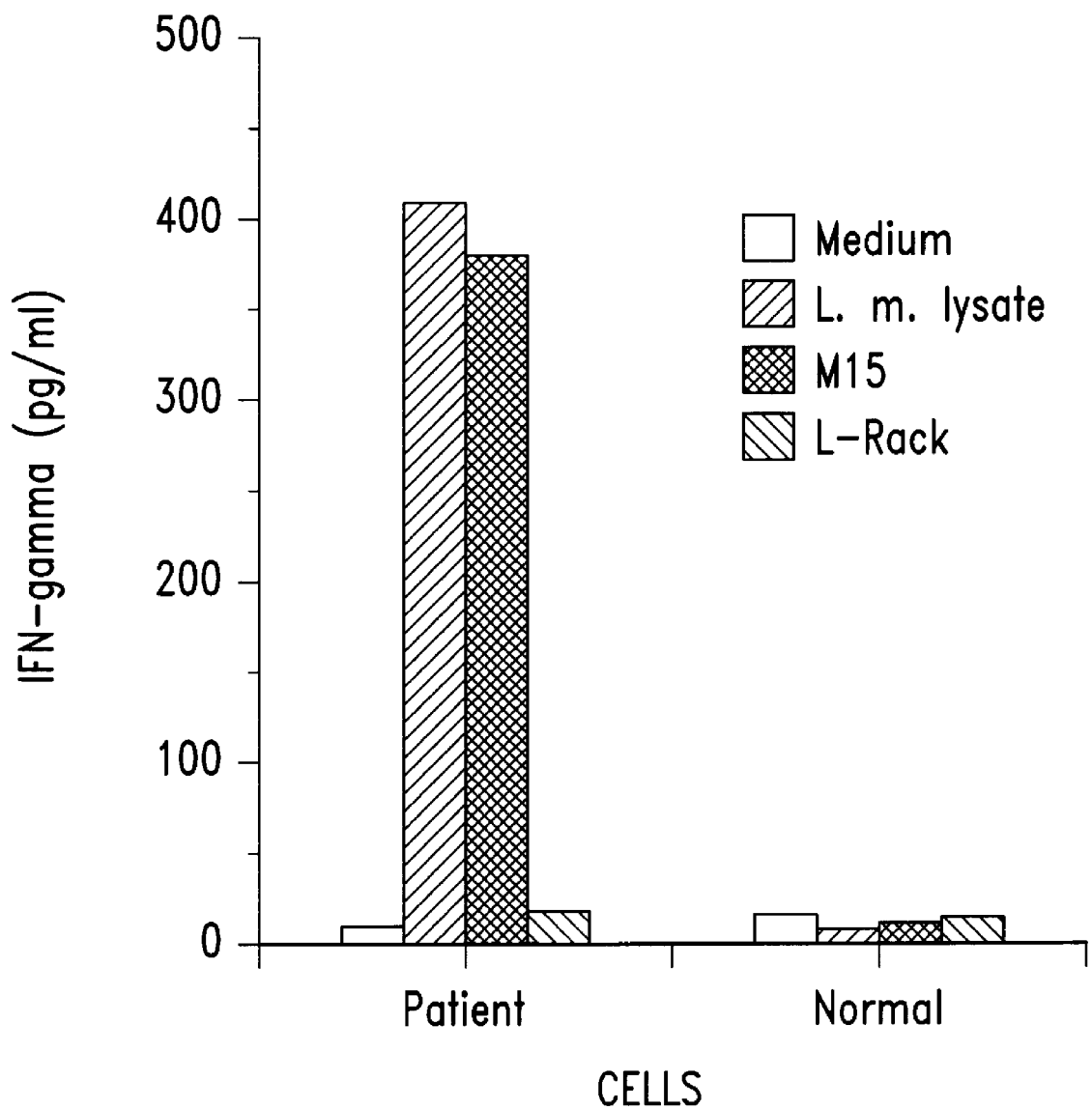
FIG. 14 shows the level of IFN-γ (in pg/mL) secreted by Leishmania-infected and uninfected human PBMC stimulated by M15, as compared to the levels stimulated by L. major lysate and L-Rack, an antigen that does not appear to be recognized by Leishmania-infected humans.
Figure 15:
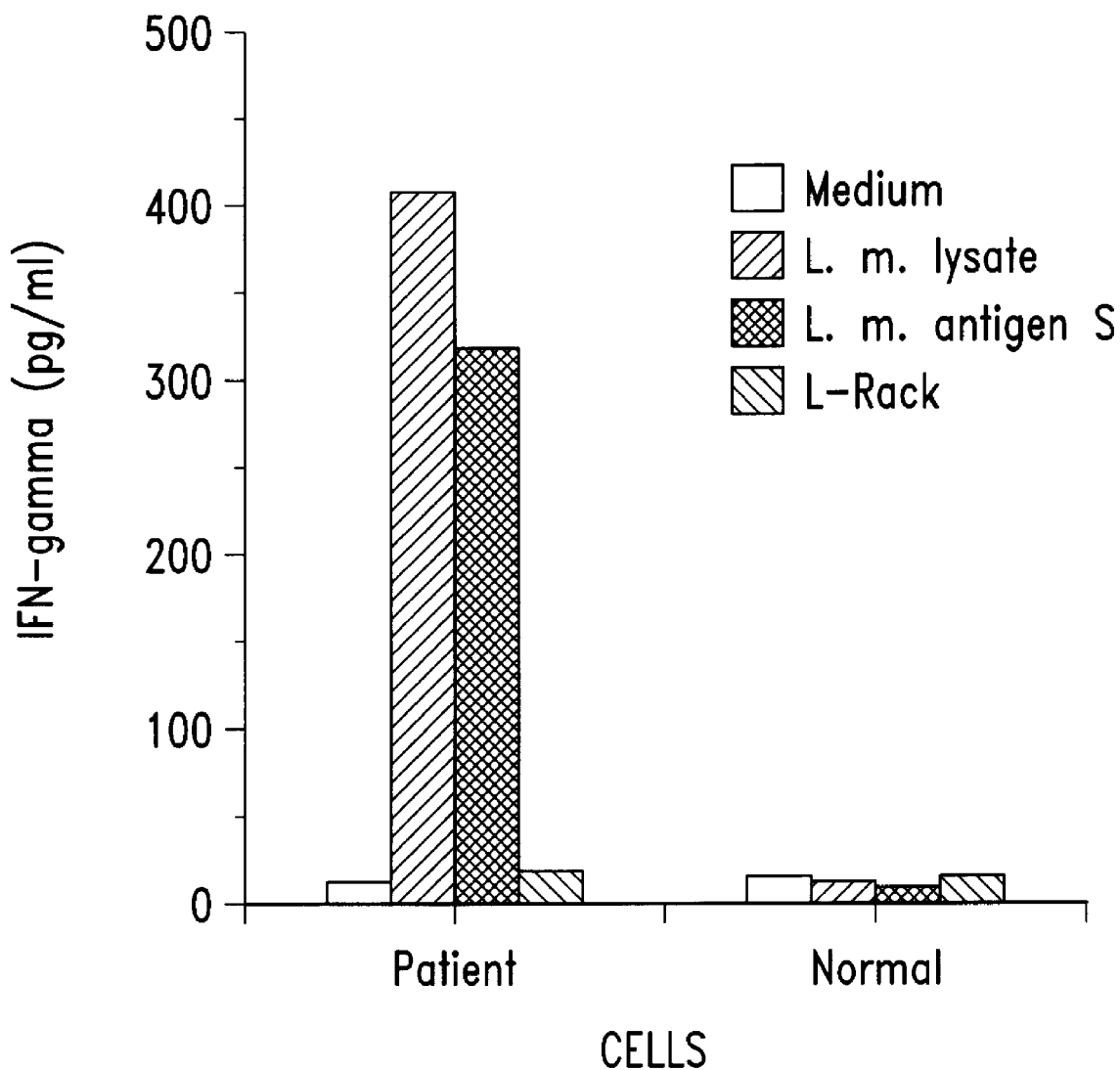
FIG. 15 shows the level of IFN-γ (in pg/mL) secreted by infected and uninfected human PBMC stimulated by soluble Leishmania antigens (S antigens), as compared to the levels stimulated by L. major lysate and L-Rack.

FIG. 14 shows the level of secreted IFN-γ in culture filtrate from infected and uninfected human PBMC preparations 72 hours after addition of 10 μg/mL *L. major* lysate, M15 or L-Rack, an immunodominant leishmanial antigen in murine leishmaniasis. Similarly, FIG. 15 illustrates the level of secreted IFN-γ in culture filtrate from infected and uninfected human PBMC preparations 72 hours after addition of 10μg/mL *L. major* lysate, soluble Leishmania antigens (prepared as described in Example 6) or L-Rack. These results indicate that M15 and soluble Leishmania antigens, but not L-Rack, are potent stimulators of IFN-γ production in patient PBMC, but not in PBMC obtained from uninfected individuals. Thus, M15 and soluble Leishmania antigens elicit a dominant Th1 cytokine profile in both mice and humans infected with Leishmania.

Example 8

Comparison of Proliferation Stimulated by Leishmania Antigens

This Example illustrates the immunogenic properties of the antigens prepared according to Examples 1, 2, 5 and 6, as determined by their ability to stimulate proliferation in lymph node cultures from infected mice and in human PBMC preparations.

For in vitro proliferation assays, $2-4 \times 10^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of [$^3$H] thymidine for the final 18 hours of culture.

Figure 16:
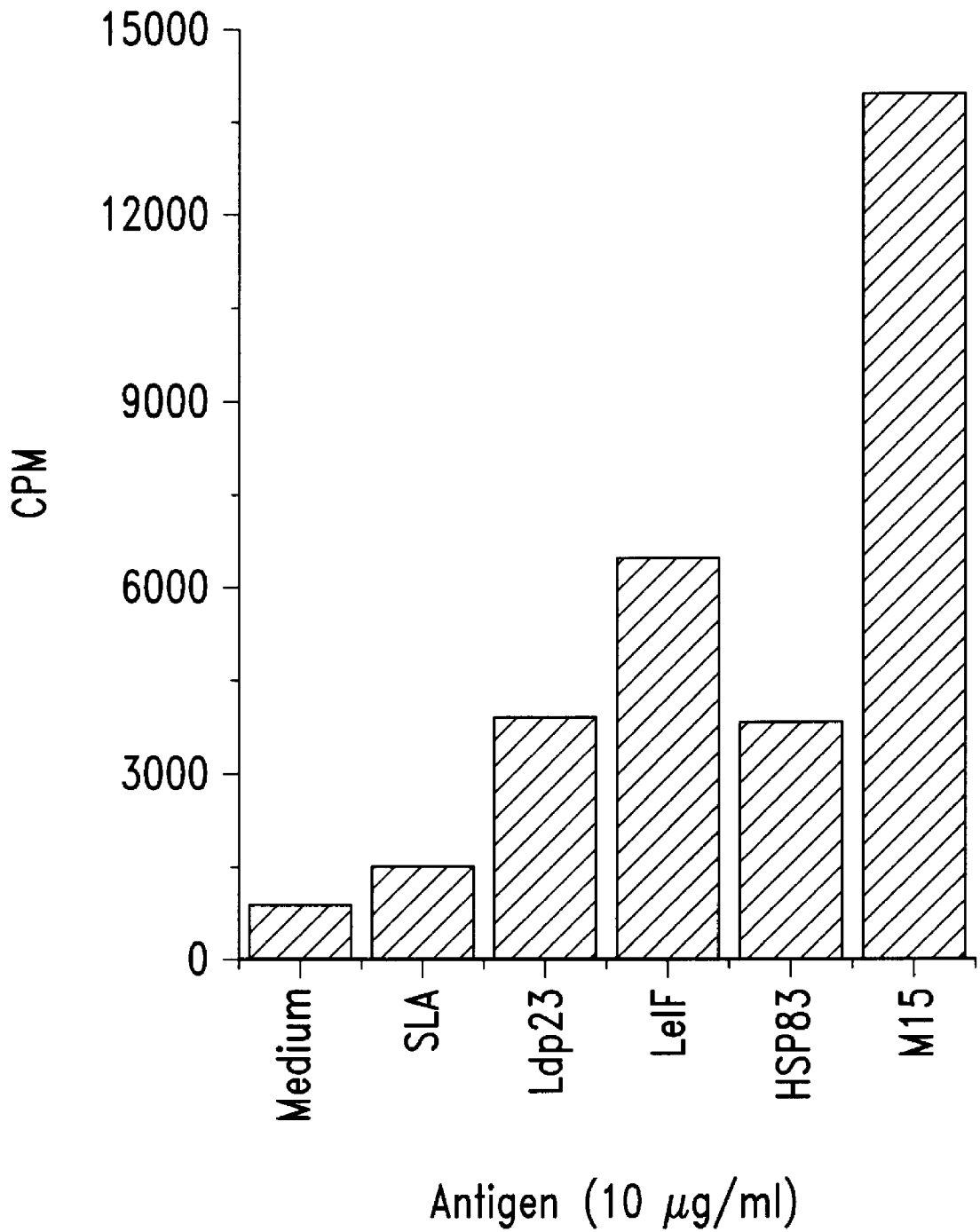
FIG. 16 illustrates the proliferation of murine lymph node cultures stimulated by the addition of representative polypeptides of the present invention. Values are expressed as cpm.

FIG. 16 illustrates the proliferation observed after addition of 10 μg/mL or 20 μg/mL of each of the following antigens to a lymph node culture prepared as described in Example 7: SLA, Ldp23, LbeIF4A, Lbhsp83, and M15. The level of proliferation without the addition of antigen is also shown. Data are represented as mean cpm. These results demonstrate that a variety of leishmanial antigens are capable of stimulatory lymph node cell proliferation from Leishmania-infected mice.

Figure 17:
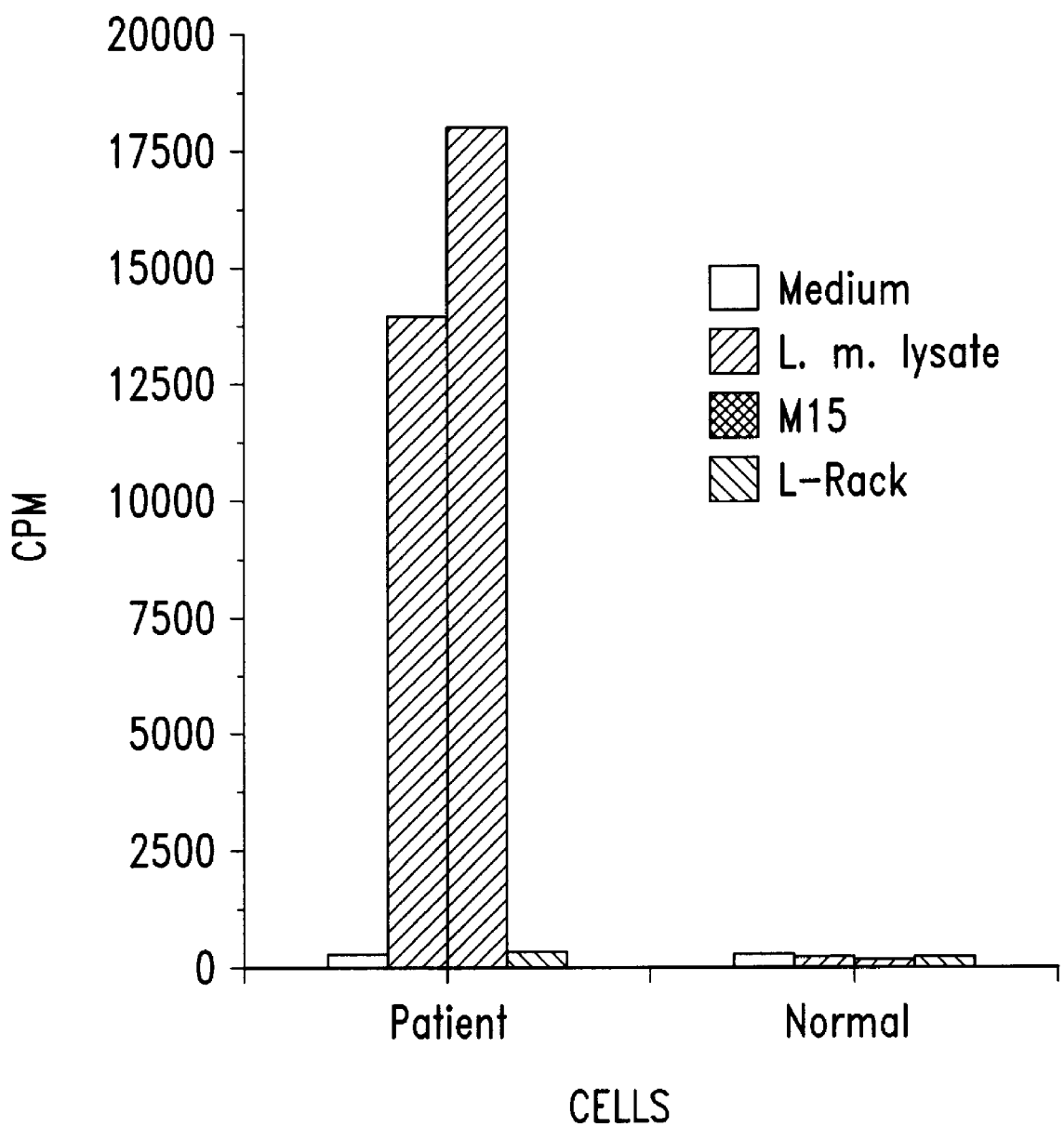
FIG. 17 shows the proliferation of human PBMC, prepared from Leishmania-immune and uninfected individuals, stimulated by M15 as compared to the proliferation stimulated by L. major lysate and L-Rack. Values are expressed as cpm.
Figure 18:
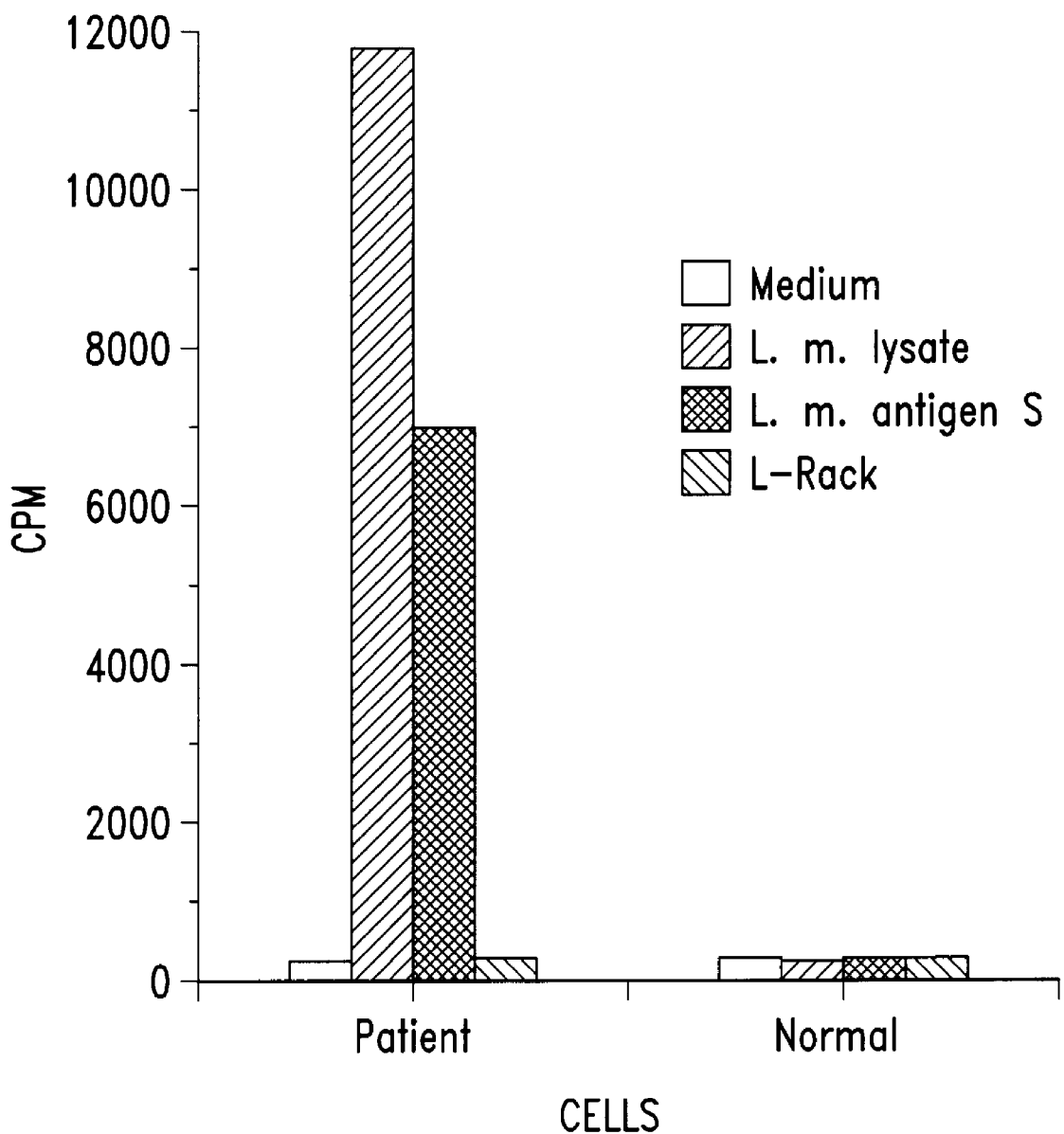
FIG. 18 illustrates the proliferation of human PBMC, prepared from infected and uninfected individuals, stimulated by soluble Leishmania antigens as compared to the proliferation stimulated by culture medium, L. major lysate and L-Rack. Values are expressed as cpm.

FIGS. 17 and 18 illustrate the proliferation observed in human PBMC preparations from Leishmania-immune and uninfected individuals following the addition of 10 μg/mL M15 and soluble Leishmania antigens, respectively. These values are compared to the proliferation observed following the addition of culture medium, *L. major* lysate or L-Rack. The results show that M15 and soluble Leishmania antigens stimulate proliferation in Leishmania-immune PBMC, but not in PBMC obtained from uninfected individuals, demonstrating that M15 and soluble antigens (but not L-Rack) are recognized by PBMC from individuals immune to Leishmania due to a previous infection.

From the foregoing, it will be appreciated that, although specific embodiments of the invention have been described herein for the purpose of illustration, various modifications may be made without deviating from the spirit and scope of the invention.

We claim:

1. An isolated polypeptide comprising an immunogenic portion of a Leishmania antigen having the amino acid sequence recited in SEQ ID NO: 4, or a variant of said antigen that differs only in conservative substitutions, modifications or combinations thereof.

2. The polypeptide of claim 1, comprising amino acids 1–175 of SEQ ID NO:4.

* * * * *